(12) United States Patent
Heiser et al.

(10) Patent No.: US 8,541,596 B2
(45) Date of Patent: Sep. 24, 2013

(54) INHIBITORS

(75) Inventors: Ulrich Heiser, Halle/Saale (DE); Daniel Ramsbeck, Halle/Saale (DE); Torsten Hoffmann, Halle/Saale (DE); Livia Boehme, Halle/Saale (DE)

(73) Assignee: Probiodrug AG, Halle/Saale (DE)

( * ) Notice: Subject to any disclaimer, the term of this patent is extended or adjusted under 35 U.S.C. 154(b) by 0 days.

(21) Appl. No.: 13/091,276

(22) Filed: Apr. 21, 2011

(65) Prior Publication Data

US 2011/0262388 A1    Oct. 27, 2011

Related U.S. Application Data

(60) Provisional application No. 61/326,401, filed on Apr. 21, 2010.

(51) Int. Cl.
*A61K 31/4184* (2006.01)
*C07D 235/08* (2006.01)

(52) U.S. Cl.
USPC ........ 548/304.4; 546/176; 548/126; 548/156; 514/314; 514/362; 514/367; 514/394

(58) Field of Classification Search
USPC .................................................... 548/304.4
See application file for complete search history.

(56) References Cited

U.S. PATENT DOCUMENTS 5,106,862 A * 4/1992 Briving et al. ................ 514/394
6,582,351 B1 * 6/2003 Sawada et al. ................ 546/118

FOREIGN PATENT DOCUMENTS

| JP | 62-024244 | | 2/1987 |
|---|---|---|---|
| JP | 62/055644 | A * | 3/1987 |
| JP | 63-250385 | | 10/1988 |
| WO | WO00/42022 | A1 | 7/2000 |
| WO | WO01/05770 | A1 | 1/2001 |
| WO | WO03/077914 | A1 | 9/2003 |
| WO | WO-2007/002092 | A1 * | 1/2007 |
| WO | WO2007/053131 | A2 | 5/2007 |
| WO | WO2007/053131 | A3 | 5/2007 |
| WO | WO2008/055950 | A1 | 5/2008 |
| WO | WO2008/128985 | A1 | 10/2008 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Abuzar et al., Synthesis of N-Aryl- & N-Heteroaryl-benzimidazoles as Potential Anthelmintics, Indian Journal of Chemistry, 1980, pp. 599-600, vol. 19B.
Brauniger et al., Darstellung von Desazaanalogen des Kinetins, Archiv der Pharmazie, 1966, pp. 13 and 194-196, vol. 299. No. 3, in German.
Chemical Abstracts Service Registration No. (CAS RN) 1069857-25-5, entered Nov. 2, 2008, 1 page.
Chemical Abstracts Service Registration No. (CAS RN) 1137428-36-4, entered Apr. 21, 2009, 1 page.
Gallagher et al., Synthesis and photolysis of azido-benzo[b]thiophens, -benzothiazoles, -benzimidazoles, and -indazoles: Novel 6,7-Diamino-benzothiazoles, -benzimidazoles, and -indazoles and 6-Diethylamino-8H-thiazolo-[5,4-c] azepines, J Chem Soc Perkin I, 1980, pp. 2362-2370.
JP62-024244 published Feb. 2, 1987, English abstract, downloaded from PAJ, 1 page.
JP63-250385 published Oct. 18, 1988, English abstract, downloaded from PAJ, 1 page.
Molnar, In 4,5-Stellung ungleich substituierte o-Nitraniline, Helvectica Chemica Acta, 1963, pp. 1779-1783, vol. 63, in German.
Roy et al., Syntheses of 4,6-Dinitro-5-substituted-amino-benzimidazoles & 4,6-Dinitro-2-methyl-5-substituted-aminobenzimidazoles, Indian J Chem, 1979, pp. 164-166, vol. 17B.
Soskic et al., Sythesis of N-n-Propyl-N-(2-arylethyl)-5-(1H-benzimidazol-2-thione)-ethylamines and Related Compounds as Potential Dopaminergic Ligands, Arzneim.-Forsch./Drug Res., 1996, pp. 741-746, vol. 46.

\* cited by examiner

*Primary Examiner* — Laura L. Stockton
(74) *Attorney, Agent, or Firm* — Dentons US LLP

(57) ABSTRACT

Novel heterocyclic derivatives as inhibitors of glutaminyl cyclase (QC, EC 2.3.2.5). QC catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

18 Claims, No Drawings

INHIBITORS

CROSS-REFERENCE TO RELATED APPLICATIONS

This application claims priority to U.S. Provisional Application Ser. No. 61/326,401, filed on Apr. 21, 2010, which is incorporated herein by reference in its entirety.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The invention relates to inhibitors of glutaminyl cyclase (QC, EC 2.3.2.5). QC catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In the case of the enzyme from *C. papaya*, a role in the plant defense against pathogenic microorganisms was suggested (El Moussaoui, A. et al. 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from *C. papaya* and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed $Glu_1$-conversion is favored around pH 6.0 while $Gln_1$-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of Alzheimer's disease.

Inhibitors of QC are described in WO 2004/098625, WO 2004/098591, WO 2005/039548, WO 2005/075436, WO 2008/055945, WO 2008/055947, WO 2008/055950 and WO2008/065141.

EP 02 011 349.4 discloses polynucleotides encoding insect glutaminyl cyclase, as well as polypeptides encoded thereby and their use in methods of screening for agents that reduce glutaminyl cyclase activity. Such agents are useful as pesticides.

WO 00/42022 discloses a series of MEK inhibitors which are claimed to be useful in the treatment of proliferative diseases such as cancer. WO 03/077914 discloses a series of MEK inhibitors which are claimed to be useful in the treatment of hyperproliferative diseases such as cancer and inflammation. Roy and Bhaduri (1979) Indian J Chem 17B, 164-166 discloses the synthesis of 4,6-dinitro-5-substituted-amino-benzoimidazole compounds. Soskic et al (1996) Arzneimittel-Forschung 46(8), 741-746 discloses the synthesis of benzoimidazole ethylamine compounds which are claimed to be useful as dopaminergic ligands. Braeuniger et al (1966) Archiv der Pharmazie 299(3), 193-196 discloses a series of benzimidazole compounds which are claimed to be useful as stimulants for plant growth. WO 2007/053131 discloses a series of acrylamide derivatives which are claimed to be useful as antibiotic agents. WO 01/05770 discloses a series of benzoimidazolone derivatives which are claimed to be useful as cGMP-PDE inhibitors.

Definitions

The terms "$k_i$" or "$K_I$" and "$K_D$" are binding constants, which describe the binding of an inhibitor to and the subsequent release from an enzyme. Another measure is the "$IC_{50}$" value, which reflects the inhibitor concentration, which at a given substrate concentration results in 50% enzyme activity.

The term "DP IV-inhibitor" or "dipeptidyl peptidase IV inhibitor" is generally known to a person skilled in the art and means enzyme inhibitors, which inhibit the catalytic activity of DP IV or DP IV-like enzymes.

"DP IV-activity" is defined as the catalytic activity of dipeptidyl peptidase IV (DP IV) and DP IV-like enzymes. These enzymes are post-proline (to a lesser extent post-alanine, post-serine or post-glycine) cleaving serine proteases found in various tissues of the body of a mammal including kidney, liver, and intestine, where they remove dipeptides from the N-terminus of biologically active peptides with a high specificity when proline or alanine form the residues that are adjacent to the N-terminal amino acid in their sequence.

The term "PEP-inhibitor" or "prolyl endopeptidase inhibitor" is generally known to a person skilled in the art and means enzyme inhibitors, which inhibit the catalytic activity of prolyl endopeptidase (PEP, prolyl oligopeptidase, POP).

"PEP-activity" is defined as the catalytic activity of an endoprotease that is capable to hydrolyze post proline bonds in peptides or proteins where the proline is in amino acid position 3 or higher counted from the N-terminus of a peptide or protein substrate.

The term "QC" as used herein comprises glutaminyl cyclase (QC) and QC-like enzymes. QC and QC-like enzymes have identical or similar enzymatic activity, further defined as QC activity. In this regard, QC-like enzymes can fundamentally differ in their molecular structure from QC.

Examples of QC-like enzymes are the glutaminyl-peptide cyclotransferase-like proteins (QPCTLs) from human (GenBank NM_017659), mouse (GenBank BC058181), *Macaca fascicularis* (GenBank AB168255), *Macaca mulatta* (GenBank XM_001110995), *Canis familiaris* (GenBank XM_541552), *Rattus norvegicus* (GenBank XM_001066591), *Mus musculus* (GenBank BC058181) and *Bos taurus* (GenBank BT026254).

The term "QC activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See therefore schemes 1 and 2.

Scheme 1: Cyclization of glutamine by QC

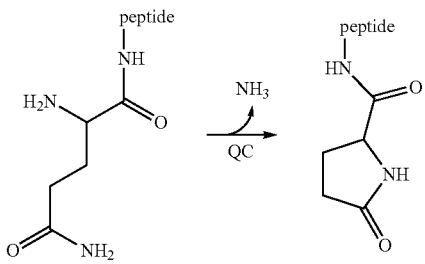

Scheme 2: Cyclization of L-homoglutamine by QC

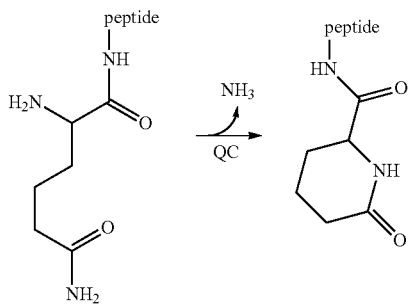

The term "EC" as used herein comprises the activity of QC and QC-like enzymes as glutamate cyclase (EC), further defined as EC activity.

The term "EC activity" as used herein is defined as intramolecular cyclization of N-terminal glutamate residues into pyroglutamic acid (pGlu*) by QC. See therefore scheme 3.

The term "QC-inhibitor" "glutaminyl cyclase inhibitor" is generally known to a person skilled in the art and means enzyme inhibitors, which inhibit the catalytic activity of glutaminyl cyclase (QC) or its glutamyl cyclase (EC) activity.

Potency of QC Inhibition

In light of the correlation with QC inhibition, in preferred embodiments, the subject method and medical use utilize an agent with an $IC_{50}$ for QC inhibition of 10 μM or less, more preferably of 1 μM or less, even more preferably of 0.1 μM or less or 0.01 μM or less, or most preferably 0.001 μM or less. Indeed, inhibitors with $K_i$ values in the lower micromolar, preferably the nanomolar and even more preferably the picomolar range are contemplated. Thus, while the active agents are described herein, for convenience, as "QC inhibitors", it will be understood that such nomenclature is not intending to limit the subject of the invention to a particular mechanism of action.

Molecular Weight of QC Inhibitors

In general, the QC inhibitors of the subject method or medical use will be small molecules, e.g., with molecular weights of 500 g/mole or less, 400 g/mole or less, preferably of 350 g/mole or less, and even more preferably of 300 g/mole or less and even of 250 g/mole or less.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: For example the term "pharmaceutically acceptable" embraces a veterinarily acceptable compound or a compound acceptable in human medicine and health care.

Throughout the description and the claims the expression "alkyl", unless specifically limited, denotes a $C_{1-12}$ alkyl group, suitably a $C_{1-8}$ alkyl group, e.g. $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hex- Scheme 3: N-terminal cyclization of unchanged glutamyl peptides by QC (EC)

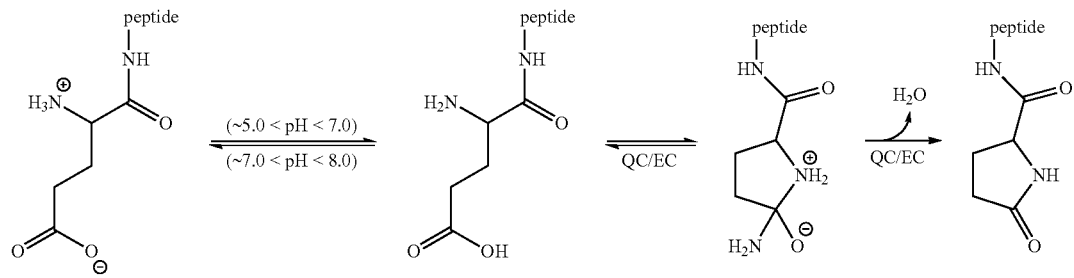

oxy (e.g. n-hexoxy), heptoxy (e.g. n-heptoxy) and octoxy (e.g. n-octoxy). Exemplary thioalkyl groups include methylthio-. Exemplary haloalkyl groups include fluoroalkyl e.g. $CF_3$.

The expression "alkenyl", unless specifically limited, denotes a $C_{2-12}$ alkenyl group, suitably a $C_{2-6}$ alkenyl group, e.g. a $C_{2-4}$ alkenyl group, which contains at least one double bond at any desired location and which does not contain any triple bonds. Alkenyl groups may be straight chain or branched. Exemplary alkenyl groups including one double bond include propenyl and butenyl. Exemplary alkenyl groups including two double bonds include pentadienyl, e.g. (1E,3E)-pentadienyl.

The expression "alkynyl", unless specifically limited, denotes a $C_{2-12}$ alkynyl group, suitably a $C_{2-6}$ alkynyl group, e.g. a $C_{2-4}$ alkynyl group, which contains at least one triple bond at any desired location and may or may not also contain one or more double bonds. Alkynyl groups may be straight chain or branched. Exemplary alkynyl groups include propynyl and butynyl.

The expression "alkylene" denotes a chain of formula —$(CH_2)_n$— wherein n is an integer e.g. 2-5, unless specifically limited.

The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six.

The expression "heterocyclyl", unless specifically limited, refers to a carbocyclyl group wherein one or more (e.g. 1, 2 or 3) ring atoms are replaced by heteroatoms selected from N, S and O. A specific example of a heterocyclyl group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O. Exemplary heterocyclyl groups containing one hetero atom include pyrrolidine, tetrahydrofuran and piperidine, and exemplary heterocyclyl groups containing two hetero atoms include morpholine, piperazine, dioxolane and dioxane. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-).

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings). An example of a typical aryl group with one aromatic ring is phenyl. An example of a typical aryl group with two aromatic rings is naphthyl.

The expression "heteroaryl", unless specifically limited, denotes an aryl residue, wherein one or more (e.g. 1, 2, 3, or 4, suitably 1, 2 or 3) ring atoms are replaced by heteroatoms selected from N, S and O, or else a 5-membered aromatic ring containing one or more (e.g. 1, 2, 3, or 4, suitably 1, 2 or 3) ring atoms selected from N, S and O. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole, oxazole, isoxazole, thiazole, isothiazole, imidazole, such as imidazol-1-yl, imidazol-2-yl imidazol-4-yl); six membered rings (e.g. pyridazine, pyrimidine, pyrazine). Exemplary monocyclic heteroaryl groups having three heteroatoms include: 1,2,3-triazole and 1,2,4-triazole. Exemplary monocyclic heteroaryl groups having four heteroatoms include tetrazole. Exemplary bicyclic heteroaryl groups include: indole (e.g. indol-6-yl), benzofuran, benzthiophene, quinoline, isoquinoline, indazole, benzimidazole, benzthiazole, quinazoline and purine.

The expression "-alkylaryl", unless specifically limited, denotes an aryl residue which is connected via an alkylene moiety e.g. a $C_{1-4}$alkylene moiety.

The expression "-alkylheteroaryl", unless specifically limited, denotes a heteroaryl residue which is connected via an alkylene moiety e.g. a $C_{1-4}$alkylene moiety.

The term "halogen" or "halo" comprises fluorine (F), chlorine (Cl) and bromine (Br).

The term "amino" refers to the group —$NH_2$.

The term "phenyl substituted by phenyl" refers to biphenyl.

The term "$\sim\!\sim\!\sim$" denotes a single bond where the stereochemistry is not defined.

When benzimidazolyl is shown as benzimidazol-5-yl, which is represented as:

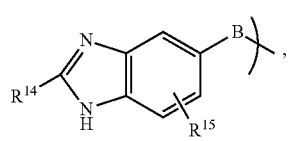

the person skilled in the art will appreciate that benzimidazol-6-yl, which is represented as:

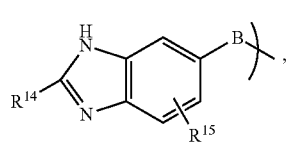

is an equivalent structure. As employed herein, the two forms of benzimidazolyl are covered by the term "benzimidazol-5-yl".

Stereoisomers:

All possible stereoisomers of the claimed compounds are included in the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base.

The compounds may also be resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts or solvates, whenever a compound is referred to in this context, a corresponding salt, solvate or polymorph is also intended, provided such is possible or appropriate under the circumstances.

Salts and solvates of the compounds of formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

Polymorph Crystal Forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

As used herein, the term "composition" is intended to encompass a product comprising the claimed compounds in the therapeutically effective amounts, as well as any product which results, directly or indirectly, from combinations of the claimed compounds.

Carriers and Additives for Galenic Formulations:

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

SUMMARY OF THE INVENTION

According to the invention there is provided a compound of formula (I):

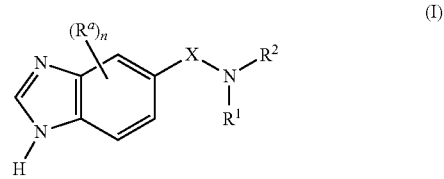

or a pharmaceutically acceptable salt, solvate or polymorph thereof, including all tautomers and stereoisomers thereof wherein:

X represents a bond or a —(CH$_2$)$_m$-group, such that when X represents —(CH$_2$)$_2$—, neither R$^1$ nor R$^2$ represent propyl;

m represents an integer selected from 1 to 3;

R$^1$ represents hydrogen, —C$_{1-6}$alkyl, -aryl, —C$_{1-6}$alkylaryl, -cycloalkyl, —C$_{1-6}$alkylcycloalkyl, —C$_{1-6}$alkyl-Het, -aryl fused to heterocyclyl, —C$_{1-6}$alkylaryl fused to heterocyclyl, -aryl substituted by heteroaryl, —C$_{1-6}$alkylaryl substituted by heteroaryl, -aryl substituted by phenyl, —C$_{1-6}$alkylaryl substituted by phenyl, -aryl substituted by phenoxy or —C$_{1-6}$alkylaryl substituted by phenoxy;

and in which any of aforesaid aryl, heterocyclyl, heteroaryl, phenyl or phenoxy groups may optionally be substituted by one or more groups selected from C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, —SO$_2$C$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl);

R$^2$ represents —C$_{1-6}$alkyl, -aryl, —C$_{1-6}$alkylaryl, -cycloalkyl, —C$_{1-6}$alkylcycloalkyl, —C$_{1-6}$alkyl-Het, -aryl fused to heterocyclyl, —C$_{1-6}$alkylaryl fused to heterocyclyl, -aryl substituted by heteroaryl, —C$_{1-6}$alkylaryl substituted by heteroaryl, -aryl substituted by phenyl, —C$_{1-6}$alkylaryl substituted by phenyl, -aryl substituted by phenoxy or —C$_{1-6}$alkylaryl substituted by phenoxy;

and in which any of aforesaid aryl, heterocyclyl, heteroaryl, phenyl or phenoxy groups may optionally be substituted by one or more groups selected from C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl);

Het represents a bicyclic heteroaryl group;

in which said bicyclic heteroaryl group may be optionally substituted by one or more groups selected from C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl);

n represents an integer selected from 0 to 3, such that when n represents 2, said R$^a$ groups do not both represent nitro; and R$^a$ represents C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, —SO$_2$C$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, C$_{1-6}$alkoxy-C$_{1-6}$alkyl-, nitro, halogen, cyano, hydroxyl, —NH$_2$, —NHC$_{1-4}$alkyl and —N(C$_{1-4}$alkyl)(C$_{1-4}$alkyl);

with the proviso that the compound of formula (I) is other than:

5-diethylamino-benzimidazolyl;
N-benzyl-1H-benzo[d]imidazol-5-amine (E2);
N-(4-methoxybenzyl)-3H-benzo[d]imidazol-5-amine (E4);
N-(4-nitrobenzyl)-3H-benzo[d]imidazol-5-amine;
(1H-benzo[d]imidazol-5-yl)-N-methylmethanamine;
4-(benzoimidazol-5-ylamino)-3-nitrobenzonitrile;
6-(benzimidazol-5-yl)amino-5-nitronicotinonitrile;
4-(1H-benzimidazol-5-ylamino)-3-nitrobenzotrifluoride;
5-amino-6-(benzimidazol-5-yl)aminonicotinonitrile; and
3-amino-4-(benzimidazol-5-ylamino)benzonitrile.

Other objects and features will be in part apparent and in part pointed out hereinafter.

DETAILED DESCRIPTION OF THE INVENTION

The first compound of the proviso, 5-diethylamino-benzimidazolyl, is a commercially available compound having no associated therapeutic indication.

The second compound of the proviso, N-benzyl-1H-benzo[d]imidazol-5-amine, is referred to in Braeuniger et al (1966) Archiv der Pharmazie 299(3), 193-196 as compound (IV).

The third compound of the proviso, N-(4-methoxybenzyl)-3H-benzo[d]imidazol-5-amine, is referred to in Braeuniger et al (1966) Archiv der Pharmazie 299(3), 193-196 as compound (VI).

The fourth compound of the proviso, N-(4-nitrobenzyl)-3H-benzo[d]imidazol-5-amine, is referred to in Braeuniger et al (1966) Archiv der Pharmazie 299(3), 193-196 as compound (VIII).

The fifth compound of the proviso, (1H-benzo[d]imidazol-5-yl)-N-methylmethanamine, is referred to as an intermediate used in the preparation of Example 76 in WO 2007/053131.

The sixth compound of the proviso, 4-(benzoimidazol-5-ylamino)-3-nitrobenzonitrile, is referred to as Preparation 12 (22) in WO 01/05770.

The seventh compound of the proviso, 6-(benzimidazol-5-yl)amino-5-nitronicotinonitrile, is referred to as Preparation 9 (8) in WO 01/05770.

The eighth compound of the proviso, 4-(1H-benzimidazol-5-ylamino)-3-nitrobenzotrifluoride, is referred to as Preparation 12 (10) in WO 01/05770.

The ninth compound of the proviso, 5-amino-6-(benzimidazol-5-yl)aminonicotinonitrile, is referred to as Preparation 15 (58) in WO 01/05770.

The tenth compound of the proviso, 3-amino-4-(benzimidazol-5-ylamino)benzonitrile, is referred to as Preparation 15 (60) in WO 01/05770.

In one particular aspect of the invention which may be mentioned, there is provided a compound of formula (I):

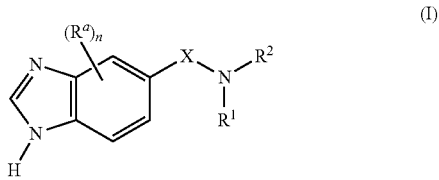

or a pharmaceutically acceptable salt, solvate or polymorph thereof, including all tautomers and stereoisomers thereof wherein:

X represents a bond or a —(CH$_2$)$_m$-group;

m represents an integer selected from 1 to 3;

$R^1$ represents hydrogen, —$C_{1-6}$alkyl, -aryl, —$C_{1-6}$alkylaryl, -cycloalkyl, —$C_{1-6}$alkylcycloalkyl, —$C_{1-6}$alkyl-Het, -aryl fused to heterocyclyl, —$C_{1-6}$alkylaryl fused to heterocyclyl, -aryl substituted by heteroaryl, —$C_{1-6}$alkylaryl substituted by heteroaryl, -aryl substituted by phenyl, —$C_{1-6}$alkylaryl substituted by phenyl, -aryl substituted by phenoxy or —$C_{1-6}$alkylaryl substituted by phenoxy;

and in which any of aforesaid aryl, heterocyclyl, heteroaryl, phenyl or phenoxy groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)$C_{1-6}$alkyl, —C(O)OC$_{1-6}$alkyl, $C_{1-6}$alkoxy-$C_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl);

$R^2$ represents —$C_{1-6}$alkyl, -aryl, —$C_{1-6}$alkylaryl, -cycloalkyl, —$C_{1-6}$alkylcycloalkyl, —$C_{1-6}$alkyl-Het, -aryl fused to heterocyclyl, —$C_{1-6}$alkylaryl fused to heterocyclyl, -aryl substituted by heteroaryl, —$C_{1-6}$alkylaryl substituted by heteroaryl, -aryl substituted by phenyl, —$C_{1-6}$alkylaryl substituted by phenyl, -aryl substituted by phenoxy or —$C_{1-6}$alkylaryl substituted by phenoxy;

and in which any of aforesaid aryl, heterocyclyl, heteroaryl, phenyl or phenoxy groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)$C_{1-6}$alkyl, —C(O)OC$_{1-6}$alkyl, $C_{1-6}$alkoxy-$C_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl);

Het represents a bicyclic heteroaryl group;

in which said bicyclic heteroaryl group may be optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)OC$_{1-6}$alkyl, $C_{1-6}$alkoxy-$C_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl);

n represents an integer selected from 0 to 3; and $R^a$ represents $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)$C_{1-6}$alkyl, —C(O)OC$_{1-6}$alkyl, $C_{1-6}$alkoxy-$C_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl); with the proviso that the compound of formula (I) is other than 5-diethylamino-benzimidazolyl.

When cycloalkyl and heterocyclyl are substituted, they are typically substituted by 1 or 2 substituents (e.g. 1 substituent). Typically the substituent is methyl. More typically carbocyclyl and heterocyclyl groups are unsubstituted.

When aryl, Het and heteroaryl are substituted, they are typically substituted by 1, 2 or 3 (e.g. 1 or 2) substituents. Substituents for aryl, Het and heteroaryl are selected from $C_{1-6}$alkyl (e.g. methyl), $C_{2-6}$alkenyl (e.g. buten-3-yl), $C_{2-6}$alkynyl (e.g. butyn-3-yl), $C_{1-6}$haloalkyl (e.g. fluoromethyl, trifluoromethyl), —$C_{1-6}$thioalkyl (e.g. —S-methyl), —SOC$_{1-4}$alkyl (e.g. —SOmethyl), —SO$_2$C$_{1-4}$alkyl (e.g. —SO$_2$-methyl), $C_{1-6}$alkoxy- (e.g. methoxy, ethoxy), —O—$C_{3-8}$cycloalkyl (e.g. —O-cyclopentyl), $C_{3-8}$cycloalkyl (e.g. cyclopropyl, cyclohexyl), —SO$_2$C$_{3-8}$cycloalkyl (e.g. —SO$_2$cyclohexyl), —SOC$_{3-6}$cycloalkyl (e.g. —SOcyclopropyl), $C_{3-6}$alkenyloxy- (e.g. —O-buten-2-yl), $C_{3-6}$alkynyloxy- (e.g. —O-buten-2-yl), —C(O)C$_{1-6}$alkyl (e.g. —C(O)ethyl), —C(O)OC$_{1-6}$alkyl (e.g. —C(O)O-methyl), $C_{1-6}$alkoxy-$C_{1-6}$alkyl- (e.g. methoxy-ethyl-), nitro, halogen (e.g. fluoro, chloro, bromo), cyano, hydroxyl, —C(O)OH, —NH$_2$, —NHC$_{1-4}$alkyl (e.g. —NHmethyl), —N(C$_{1-4}$alkyl)(C$_{1-4}$alkyl) (e.g. —N(methyl)$_2$), —C(O)N(C$_{1-4}$alkyl)(C$_{1-4}$alkyl) (e.g. —C(O)N(methyl)$_2$), —C(O)NH$_2$, —C(O)NH(C$_{1-4}$alkyl) (e.g. —C(O)NHmethyl), —C(O)NH(C$_{3-10}$cycloalkyl) (e.g. —C(O)NHcyclopropyl). More typically, substituents will be selected from $C_{1-6}$alkyl (e.g. methyl), $C_{1-6}$haloalkyl (e.g. $C_{1-6}$-fluoroalkyl, e.g. CF$_3$), $C_{1-6}$alkoxy (e.g. OMe), halogen and hydroxy.

When $R^1$ or $R^2$ represents —$C_{1-6}$alkylcycloalkyl, —$C_{1-6}$alkylaryl or —$C_{1-6}$alkyl-Het, examples wherein alkyl is branched include:

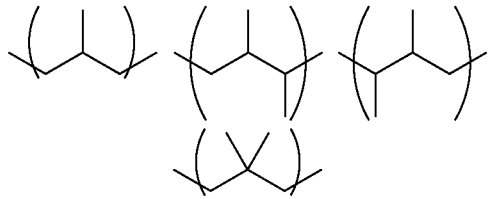

When $R^1$ or $R^2$ represents aryl or —$C_{1-6}$alkylaryl, said aryl suitably represents optionally substituted phenyl. Exemplary substituted phenyl groups for $R^1$ and $R^2$ include 2-bromophenyl, 2-bromo-4-fluorophenyl-, 2-bromo-5-fluorophenyl-, 2-chlorophenyl-, 2-fluorophenyl-, 3-chlorophenyl-, 3-bromophenyl-, 3-fluorophenyl-, 4-chlorophenyl-, 4-fluorophenyl-, 4-bromophenyl-, 4-bromo-2-fluorophenyl, 2,3-dichlorophenyl-, 2,3-difluorophenyl-, 2,3,4-trifluorophenyl, 2,4-dichlorophenyl-, 2,4-difluororophenyl-, 2,4,6-trifluorophenyl-, 2,5-dichlorophenyl-, 2,6-dichlorophenyl-, 2,6-difluorophenyl-, 3,4-dichlorophenyl-, 3,4-difluorophenyl-, 3,5-difluorophenyl-, 2,4,5-trifluorophenyl-, 3,4,5-trifluorophenyl-, 2,4-dimethylphenyl-, 3-methylphenyl-, 3,4-dimethylphenyl-, 4-methylphenyl-, 4-isopropylphenyl-, 4-tert-butylphenyl-, 2,4,6-trimethylphenyl-, 2-isopropyl-6-methylphenyl-, 2-(trifluoromethyl)phenyl-, 4-(trifluoromethyl)phenyl-, 2,4-bis(trifluoromethyl)phenyl-, 3,5-bis(trifluoromethyl)phenyl-, 2-methoxyphenyl-, 2,4-dimethoxyphenyl-, 2,6-dimethoxyphenyl-, 3-methoxyphenyl-, 4-methoxyphenyl-, 4-ethoxyphenyl-, 4-propoxyphenyl-, 4-butoxyphenyl-, 4-pentoxyphenyl-, 4-isopropyloxyphenyl-, 3-(cyclopentyloxy)-4-methoxyphenyl-, 3,4,5-trimethoxyphenyl-, 3,4-dimethoxyphenyl-, 3,5-dimethoxyphenyl-, 4-tetrafluoroethyloxyphenyl, 4-cyanophenyl-, 4-thiomethylphenyl- and 4-dimethylaminophenyl. Alternatively, $R^2$ may represent unsubstituted phenyl-. Further exemplary substituted phenyl groups include 2,3-difluoro-4-methylphenyl, 2-fluoro-5-(trifluoromethyl)phenyl-, 2-hydroxy-3-methoxyphenyl-, 2-hydroxy-5-methylphenyl-, 3-fluoro-4-(trifluoromethyl)phenyl-, 3-fluoro-5-(trifluoromethyl)phenyl-, 2-fluoro-4-(trifluoromethyl)phenyl-, 2-fluoro-3-(methyl)phenyl-, 3-fluoro-4-(methoxy)phenyl-, 3-hydroxy-4-methoxyphenyl-, 4-chloro-3-(trifluoromethyl)phenyl-, 4-chloro-3-methylphenyl-, 4-bromo-4-ethylphenyl-, 2,3,5,6-tetrafluoro-4-(methyl)phenyl-, 2,6-difluoro-4-(methoxy)phenyl- and 2-fluoro-4,5-(dimethoxy)phenyl-.

When $R^1$ or $R^2$ represents aryl or —$C_{1-6}$alkylaryl, said aryl suitably represents optionally substituted naphthyl. Examples include unsubstituted naphthyl (e.g. naphthalen-1-yl, naphthalen-2-yl, naphthalen-3-yl) as well as substituted naphthyl (e.g. 4-methyl-naphthalen-2-yl-, 5-methyl-naphthalen-3-yl-, 7-methyl-naphthalen-3-y- and 4-fluoro-naphthalen-2-yl-).

When $R^1$ or $R^2$ represents cycloalkyl or —$C_{1-6}$alkylcycloalkyl said cycloalkyl suitably represents optionally substituted cycloalkyl. Examples of cycloalkyl include cyclopropyl, cyclobutyl, cyclopentyl, cyclohexyl and cycloheptyl. Examples of substituted carbocyclyl include 2-methyl-cyclohexyl-, 3-methyl-cyclohexyl- and 4-methyl-cyclohexyl-.

When $R^1$ or $R^2$ represents —$C_{1-6}$alkyl-Het, suitable examples of Het include bicyclic rings (e.g. 9 or 10 membered rings) which may optionally be substituted. Example 9 membered rings include 1H-indolyl (e.g. 1H-indol-3-yl, 1H-indol-5-yl), benzothiophenyl (e.g. benzo[b]thiophen-3-yl, particularly 2-benzo[b]thiophen-3-yl), benzo[1,2,5]oxadiazolyl (e.g. benzo[1,2,5]oxadiazol-5-yl), benzo[d]thiazolyl (e.g. benzo[d]thiazol-2-yl), benzo[1,2,5]thiadiazolyl (e.g. benzo[1,2,5]-thiadiazol-5-yl, benzo[1,2,5]thiadiazol-6-yl). Example 10 membered rings include quinolinyl (e.g. quinolin-3-yl, quinolin-4-yl, quinolin-6-yl, quinolin-8-yl). Specific substituents that may be mentioned are one or more e.g. 1, 2 or 3 groups selected from halogen, hydroxyl, alkyl (e.g. methyl) and alkoxy- (e.g. methoxy-). Example substituted 9-membered rings include 1-methyl-1H-indol-3-yl, 2-methyl-1H-indol-3-yl, 6-methyl-1H-indol-3-yl and 5-chlorobenzo[b]thiophen-3-yl. Example substituted 10 membered rings include 2-chloro-quinolin-3-yl, 8-hydroxy-quinolin-2-yl, 2-methyl-quinolin-6-yl, oxo-chromenyl (e.g. 4-oxo-4H-chromen-3-yl) and 6-methyl-4-oxo-4H-chromen-3-yl.

When $R^1$ or $R^2$ represents aryl or —$C_{1-6}$alkylaryl substituted by phenyl or aryl or —$C_{1-6}$alkylaryl substituted by a heteroaryl group (such as a monocyclic heteroaryl), in which any of aforesaid phenyl and heteroaryl groups may optionally be substituted, typically the aryl ring connected directly to the nitrogen atom is unsubstituted and the terminal phenyl ring or the monocyclic heteroaryl ring is optionally substituted by one, two or three substitutents (e.g. one or two, e.g. one). Typically the terminal phenyl or monocyclic heteroaryl group is unsubstituted. Typically the terminal phenyl or monocyclic heteroaryl group substitutes the aryl ring (i.e. phenyl) at the 4-position.

When $R^1$ or $R^2$ represents aryl or —$C_{1-6}$alkylaryl substituted by phenyl in which any of aforesaid aryl or phenyl groups may optionally be substituted, examples include -biphenyl-4-yl and —$CH_2$-biphenyl-4-yl.

When $R^1$ or $R^2$ represents aryl or —$C_{1-6}$alkylaryl substituted by a monocyclic heteroaryl group, in which any of aforesaid aryl and heteroaryl groups may optionally be substituted, examples include (4-thiophen-2-yl)-benzyl- and (4-(oxazol-5-yl)phenyl-.

When $R^1$ or $R^2$ represents aryl or —$C_{1-6}$alkylaryl substituted by phenyloxy in which any of aforesaid aryl and phenyloxy groups may optionally be substituted, examples include 4-benzyloxy-phenyl-, 4-(3-methylbenzyloxy)phenyl- and 4-(4-methylbenzyloxy)phenyl-.

When $R^1$ or $R^2$ represents aryl or —$C_{1-6}$alkylaryl fused to heterocyclyl, examples include benzo[1,3]dioxo-4-yl-, 3,4-dihydro-benzo[1,4]dioxepin-9-yl and 2,3-dihydro-benzo[1,4]dioxin-4-yl-.

Suitably, $R^1$ represents hydrogen, $C_{1-6}$alkyl (e.g. methyl), —$C_{1-6}$alkylaryl (e.g. —$CH_2$-phenyl, —$(CH_2)_2$-phenyl, —$(CH_2)_3$-phenyl or —$CH_2$-naphthyl), —$C_{1-6}$alkyl-Het (e.g. —$CH_2$-benzothiazolyl, —$CH_2$-benzothiadiazolyl, —$CH_2$-benzothiophenyl, —$CH_2$-quinolinyl), —$C_{1-6}$alkylaryl fused to heterocyclyl (e.g. dihydrobenzodioxepinyl) or —$C_{1-6}$alkylaryl substituted by heteroaryl (e.g. —$CH_2$-phenyl substituted by thiophenyl).

Suitably, $R^2$ represents —$C_{1-6}$alkyl (e.g. butyl, pentan-2-yl or isobutyl), -aryl (e.g. phenyl), —$C_{1-6}$alkylaryl (e.g. —$CH_2$-phenyl, —$CH_2$-naphthyl, —$CH(CH_3)$-phenyl, —$(CH_2)_2$-phenyl or —$(CH_2)_3$-phenyl), —$C_{1-6}$alkylcycloalkyl (e.g. —$CH_2$-cyclohexyl), —$C_{1-6}$alkyl-Het (e.g. —$CH_2$-benzothiazolyl, —$CH_2$-benzothiadiazolyl, —$CH_2$-benzothiophenyl or —$CH_2$-quinolinyl), —$C_{1-6}$alkylaryl fused to heterocyclyl (e.g. dihydrobenzodioxepinyl) or —$C_{1-6}$alkylaryl substituted by heteroaryl (e.g. —$CH_2$-phenyl substituted by thiophenyl). In one embodiment, $R^2$ represents a group other than —$C_{1-6}$alkyl. In a further embodiment, $R^2$ represents -aryl (e.g. phenyl), —$C_{1-6}$alkylaryl (e.g. —$CH_2$-phenyl, —$CH_2$-naphthyl, —$CH(CH_3)$-phenyl, —$(CH_2)_2$-phenyl or —$(CH_2)_3$-phenyl), —$C_{1-6}$alkylcycloalkyl (e.g. —$CH_2$-cyclohexyl), —$C_{1-6}$alkyl-Het (e.g. —$CH_2$-benzothiazolyl, —$CH_2$-benzothiadiazolyl, —$CH_2$-benzothiophenyl or —$CH_2$-quinolinyl), —$C_{1-6}$alkylaryl fused to heterocyclyl (e.g. dihydrobenzodioxepinyl) or —$C_{1-6}$alkylaryl substituted by heteroaryl (e.g. —$CH_2$-phenyl substituted by thiophenyl).

In one embodiment, $R^1$ represents hydrogen and $R^2$ represents $C_{1-6}$alkyl (e.g. butyl, pentan-2-yl or isobutyl), -aryl (e.g. phenyl), —$C_{1-6}$alkylaryl (e.g. —$CH_2$-phenyl, —$CH_2$-naphthyl, —$CH(CH_3)$-phenyl or —$(CH_2)_2$-phenyl), —$C_{1-6}$alkylcycloalkyl (e.g. —$CH_2$-cyclohexyl), —$C_{1-6}$alkyl-Het (e.g. —$CH_2$-benzothiazolyl, —$CH_2$-benzothiadiazolyl, —$CH_2$-benzothiophenyl or —$CH_2$-quinolinyl), —$C_{1-6}$alkylaryl substituted by heteroaryl (e.g. —$CH_2$-phenyl substituted by thiophenyl) or —$C_{1-6}$alkylaryl fused to heterocyclyl (e.g. dihydrobenzodioxepinyl); wherein said phenyl group is optionally substituted by one or more halogen (e.g. chlorine, fluorine or bromine), $C_{1-6}$alkoxy (e.g. methoxy), $C_{1-6}$alkyl (e.g. methyl or ethyl), —$C_{1-6}$thioalkyl (e.g. thiomethyl) or —N($C_{1-4}$alkyl)($C_{1-4}$alkyl) (e.g. —$NMe_2$) groups; and wherein said Het group is optionally substituted by one or more halogen (e.g. chlorine) or $C_{1-6}$alkyl (e.g. methyl) groups.

In one embodiment, $R^1$ represents $C_{1-6}$alkyl (e.g. methyl) and $R^2$ represents -aryl (e.g. phenyl) or —$C_{1-6}$alkylaryl (e.g. —$CH_2$-phenyl); wherein said phenyl group is optionally substituted by one or more halogen (e.g. fluorine) or $C_{1-6}$alkoxy (e.g. methoxy) groups.

In one embodiment, $R^1$ represents —$C_{1-6}$alkylaryl (e.g. —$CH_2$-phenyl, —$(CH_2)_2$-phenyl, —$(CH_2)_3$-phenyl or —$CH_2$-naphthyl) and $R^2$ represents —$C_{1-6}$alkylaryl (e.g. —$CH_2$-phenyl or —$CH_2$-naphthyl), —$C_{1-6}$alkylcycloalkyl (e.g. —$CH_2$-cyclohexyl) or —$C_{1-6}$alkyl (e.g. butyl, isobutyl or pentan-2-yl); wherein said phenyl groups are optionally substituted by one or more halogen (e.g. chlorine, fluorine or bromine), cyano, $C_{1-6}$alkyl (e.g. methyl, ethyl, isopropyl, t-butyl), $C_{1-6}$alkoxy (e.g. methoxy), —$C_{1-6}$thioalkyl (e.g. thiomethyl) or —N($C_{1-4}$alkyl)($C_{1-4}$alkyl) (e.g. —$NMe_2$) groups.

In one embodiment, $R^1$ and $R^2$ both represent —$C_{1-6}$alkylaryl (e.g. —$CH_2$-phenyl, —$(CH_2)_2$-phenyl, —$(CH_2)_3$-phenyl or —$CH_2$-naphthyl); wherein said phenyl groups are optionally substituted by one or more halogen (e.g. chlorine, fluorine or bromine), cyano, $C_{1-6}$alkyl (e.g. methyl, ethyl, isopropyl, t-butyl), $C_{1-6}$alkoxy (e.g. methoxy), —$C_{1-6}$thioalkyl (e.g. thiomethyl) or —N($C_{1-4}$alkyl)($C_{1-4}$alkyl) (e.g. —$NMe_2$) groups.

In one embodiment, $R^1$ and $R^2$ both represent —$C_{1-6}$alkylaryl fused to heterocyclyl (e.g. dihydrobenzodioxepinyl).

In one embodiment, $R^1$ and $R^2$ both represent —$C_{1-6}$alkylaryl substituted by heteroaryl (e.g. —$CH_2$-phenyl substituted by thiophenyl).

In one embodiment, $R^1$ represents —$C_{1-6}$alkyl-Het (e.g. —$CH_2$-benzothiazolyl, —$CH_2$-benzothiadiazolyl, —$CH_2$-benzothiophenyl, —$CH_2$-quinolinyl) and $R^2$ represents —$C_{1-6}$alkyl-Het (e.g. —$CH_2$-benzothiazolyl, —$CH_2$-benzothiadiazolyl, —$CH_2$-benzothiophenyl, —$CH_2$-quinolinyl) or —$C_{1-6}$alkylcarbocyclyl (e.g. —$CH_2$-phenyl); wherein said Het groups are optionally substituted by one or more halogen (e.g. chlorine) or $C_{1-6}$alkyl (e.g. methyl) groups; and wherein said phenyl group is optionally substituted by one or more —$C_{1-6}$thioalkyl (e.g. thiomethyl), $C_{1-6}$alkyl (e.g. ethyl), $C_{1-6}$alkoxy (e.g. methoxy), halogen (e.g. chlorine) or —N($C_{1-4}$alkyl)($C_{1-4}$alkyl) (e.g. —$NMe_2$) groups.

In one embodiment, $R^1$ and $R^2$ both represent —$C_{1-6}$alkyl-Het (e.g. —$CH_2$-benzothiazolyl, —$CH_2$-benzothiadiazolyl, —$CH_2$-benzothiophenyl, —$CH_2$-quinolinyl); wherein said Het groups are optionally substituted by one or more halogen (e.g. chlorine) or $C_{1-6}$alkyl (e.g. methyl) groups.

In one embodiment, $R^1$ represents aryl (e.g. phenyl) and $R^2$ represents —$C_{1-6}$alkylaryl (e.g. —$CH_2$-phenyl).

Suitably, X represents a bond or a —$CH_2$-group. More suitably, X represents a bond. When X represents a —$(CH_2)_m$-group, m suitably represents an integer selected from 1 or 2, more suitably 1.

Suitably, n represents an integer from 0 to 2, more suitably 0 or 1. In one embodiment, n represents 0. When present, it will be appreciated that the $R^a$ substituent will be located on the phenyl ring of the benzimidazolyl group.

Processes

According to a further aspect of the invention there is provided a process for preparing a compound of formula (I) which comprises:

(a) preparing a compound of formula (I) wherein X represents a bond by reacting a compound of formula (II)

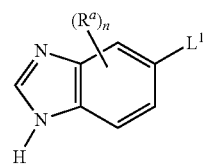

(II)

wherein $R^a$ and n are as defined above for compounds of formula (I) and $L^1$ represents a suitable leaving group, such as bromine, with a compound of formula $NHR^1R^2$, wherein $R^1$ and $R^2$ are as defined above for compounds of formula (I). Process (a) typically comprises reaction in a suitable solvent, such as THF in the presence of 2-dicyclohexylphosphino-2'-(N,N-dimethylamino)biphenyl, $Pd_2 dba_3$ and lithiumbis(trimethylsilyl)amide, followed by heating under an Argon atmosphere to 65° C. for 24 h. A non-limiting example of the methodology of process (a) is described in Method 1 herein.

(b) preparing a compound of formula (I) wherein X represents a bond, $R^1$ represents hydrogen and $R^2$ represents —$C_{1-6}$alkylaryl, —$C_{1-6}$alkyl-Het, —$C_{1-6}$alkylaryl fused to heterocyclyl, —$C_{1-6}$alkylaryl substituted by heteroaryl, —$C_{1-6}$alkylaryl substituted by phenyl or —$C_{1-6}$alkylaryl substituted by phenoxy, by alkylating a compound of formula (III):

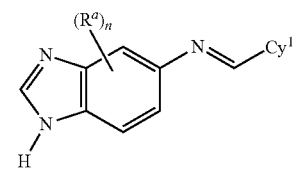

(III)

wherein $R^a$ and n are as defined above for compounds of formula (I) and $Cy^1$ represents the aryl or Het group of $R^2$. Process (b) typically comprises addition of a compound of formula (III) to a suitable reducing agent, such as sodium borohydride, in a suitable solvent, such as ethanol at room temperature. A non-limiting example of the methodology of process (b) is described in Method 2 herein.

(c) preparing a compound of formula (I) wherein X represents a bond, $R^1$ represents hydrogen and $R^2$ represents —$C_{1-6}$alkyl, —$C_{1-6}$alkylaryl, —$C_{1-6}$alkylcycloalkyl, —$C_{1-6}$alkyl-Het, —$C_{1-6}$alkylaryl fused to heterocyclyl, —$C_{1-6}$alkylaryl substituted by heteroaryl, —$C_{1-6}$alkylaryl substituted by phenyl or —$C_{1-6}$alkylaryl substituted by phenoxy, by reacting a compound of formula (IV):

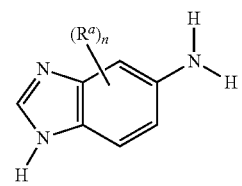

(IV)

wherein $R^a$ and n are as defined above for compounds of formula (I), with a compound of formula H—CO—$R^2$; wherein $R^2$ is as defined above for compounds of formula (I). Process (c) typically comprises reaction in a suitable solvent, such as methanol followed by addition of a suitable reducing agent, such as sodium borohydride. A non-limiting example of the methodology of process (c) is described in Method 3 herein.

(d) preparing a compound of formula (I) wherein: X represents a bond, $R^1$ represents hydrogen and $R^2$ is as defined above; or X represents a bond and $R^1$ and $R^2$ represent identical groups, by reacting a compound of formula (IV):

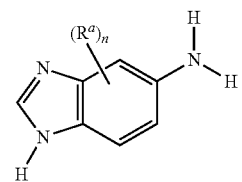

(IV)

or an optionally protecting derivative thereof, wherein $R^a$ and n are as defined above for compounds of formula (I), with a compound of formula $L^2$-$R^2$, wherein $L^2$ represents a suitable leaving group such as bromine and $R^2$ is as defined above for compounds of formula (I). Process (d) typically comprises dissolving the compound of formula (IV) in a suitable solvent, such as DMF followed by treatment with the compound of formula $L^2$-$R^2$ and potassium carbonate. A non-limiting example of the methodology of process (d) is described in Methods 4 and 5 herein.

(e) preparing a compound of formula (I) wherein X represents a —$(CH_2)_m$-group, by reacting a compound of formula (VI):

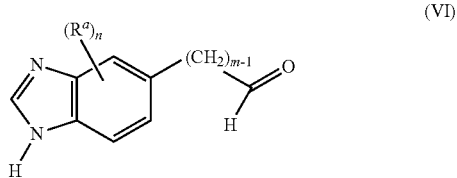

(VI)

wherein $R^1$ and n are as defined above for compounds of formula (I), with a compound of formula $HNR^1R^2$, wherein $R^1$ and $R^2$ are as defined above for compounds of formula (I). Process (f) typically comprises dissolving the compound of formula (VI) in a suitable solvent, such as tetrahydrofuran, followed by addition of the compound of formula $HNR^1R^2$, $NaBH(AcO)_3$ and ethanol. A non-limiting example of the methodology of process (f) is described in Method 7 herein.

(f) interconversion of compounds of formula (I). One such example of an interconversion reaction comprises preparing a compound of formula (I) wherein $R^1$ represents a group other than hydrogen by reacting a compound of formula (V):

(V)

wherein $R^2$, n and $R^a$ are as defined for compounds of formula (I), with a compound of formula $L^4$—$R^{1a}$, wherein $L^4$ represents a suitable leaving group such as bromine and $R^{1a}$ represents an $R^1$ group as defined for compounds of formula (I) other than hydrogen. This interconversion typically comprises dissolving the compound of formula (V) in a suitable solvent, such as DMF followed by treatment with the compound of formula $L^4$—$R^{1a}$ and potassium carbonate. A non-limiting example of the methodology of this interconversion is described in Method 6 herein.

(g) deprotecting a compound of formula (I) which is protected.

Compounds of formula (I) and intermediate compounds may also be prepared using techniques analogous to those known to a skilled person, or described herein.

Novel intermediates are claimed as an aspect of the present invention.

Therapeutic Uses

Physiological substrates of QC (EC) in mammals are, e.g. amyloid beta-peptides (3-40), (3-42), (11-40 and (11-42), ABri, ADan, Gastrin, Neurotensin, FPP, CCL 2, CCL 7, CCL 8, CCL 16, CCL 18, Fractalkine, Orexin A, [Gln$^3$]-glucagon (3-29), [Gln$^5$]-substance P(5-11) and the peptide QYNAD. For further details see table 1. The compounds and/or combinations according to the present invention and pharmaceutical compositions comprising at least one inhibitor of QC (EC) are useful for the treatment of conditions that can be treated by modulation of QC activity.

TABLE 1

Amino acid sequences of physiological active peptides with an N-terminal glutamine residue, which are prone to be cyclized to final pGlu

| Peptide | Amino acid sequence | Function |
| --- | --- | --- |
| Abeta(1-42) | Asp-Ala-Glu-Phe-Arg-His-Asp-Ser-<br>Gly-Tyr-Glu-Val-His-His-Gln-Lys-<br>Leu-Val-Phe-Phe-Ala-Glu-Asp-Val-<br>Gly-Ser-Asn-Lys-Gly-Ala-Ile-Ile-<br>Gly-Leu-Met-Val-Gly-Gly-Val-Val-<br>Ile-Ala | Plays a role in<br>neurodegeneration, e.g. in<br>Alzheimer's Disease, Familial<br>British Dementia, Familial<br>Danish Dementia, Down<br>Syndrome |
| Abeta(1-40) | Asp-Ala-Glu-Phe-Arg-His-Asp-Ser-<br>Gly-Tyr-Glu-Val-His-His-Gln-Lys-<br>Leu-Val-Phe-Phe-Ala-Glu-Asp-Val-<br>Gly-Ser-Asn-Lys-Gly-Ala-Ile-Ile-<br>Gly-Leu-Met-Val-Gly-Gly-Val-Val | Plays a role in<br>neurodegeneration, e.g. in<br>Alzheimer's Disease, Familial<br>British Dementia, Familial<br>Danish Dementia, Down<br>Syndrome |
| Abeta(3-42) | Glu-Phe-Arg-His-Asp-Ser-Gly-Tyr-<br>Glu-Val-His-His-Gln-Lys-Leu-Val-<br>Phe-Phe-Ala-Glu-Asp-Val-Gly-Ser-<br>Asn-Lys-Gly-Ala-lle-Ile-Gly-Leu-<br>Met-Val-Gly-Gly-Val-Val-Ile-Ala | Plays a role in<br>neurodegeneration, e.g. in<br>Alzheimer's Disease, Familial<br>British Dementia, Familial<br>Danish Dementia, Down<br>Syndrome |
| Abeta(3-40) | Glu-Phe-Arg-His-Asp-Ser-Gly-Tyr-<br>Glu-Val-His-His-Gln-Lys-Leu-Val-<br>Phe-Phe-Ala-Glu-Asp-Val-Gly-Ser-<br>Asn-Lys-Gly-Ala-Ile-Ile-Gly-Leu-<br>Met-Val-Gly-Gly-Val-Val | Plays a role in<br>neurodegeneration, e.g. in<br>Alzheimer's Disease, Familial<br>British Dementia, Familial<br>Danish Dementia, Down<br>Syndrome |

TABLE 1 -continued

Amino acid sequences of physiological active peptides with an N-terminal glutamine residue, which are prone to be cyclized to final pGlu

| Peptide | Amino acid sequence | Function |
| --- | --- | --- |
| Abeta(11-42) | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta(11-40) | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| ABri | EASNCFA IRHFENKFAV ETLIC SRTVKKNIIEEN | Pyroglutamated form plays a role in Familial British Dementia |
| ADan | EASNCFA IRHFENKFAV ETLIC FNLFLNSQEKHY | Pyroglutamated form plays a role in Familial Danish Dementia |
| Gastrin 17 Swiss-Prot: P01350 | QGPWL EEEEEAYGWM DF (amide) | Gastrin stimulates the stomach mucosa to produce and secrete hydrochloric acid and the pancreas to secrete its digestive enzymes. It also stimulates smooth muscle contraction and increases blood circulation and water secretion in the stomach and intestine. |
| Neurotensin Swiss-Prot: P30990 | QLYENKPRRP YIL | Neurotensin plays an endocrine or paracrine role in the regulation of fat metabolism. It causes contraction of smooth muscle. |
| FPP | QEP amide | A tripeptide related to thyrotrophin releasing hormone (TRH), is found in seminal plasma. Recent evidence obtained in vitro and in vivo showed that FPP plays an important role in regulating sperm fertility. |
| TRH Swiss-Prot: P20396 | QHP amide | TRH functions as a regulator of the biosynthesis of TSH in the anterior pituitary gland and as a neurotransmitter/neuromodulator in the central and peripheral nervous systems. |
| GnRH Swiss-Prot: P01148 | QHWSYGL RP(G) amide | Stimulates the secretion of gonadotropins; it stimulates the secretion of both luteinizing and follicle-stimulating hormones. |
| CCL16 (small inducible cytokine A16) Swiss-Prot: O15467 | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ | Shows chemotactic activity for lymphocytes and monocytes but not neutrophils. Also shows potent myelosuppressive activity, suppresses proliferation of myeloid progenitor cells. Recombinant SCYA16 shows chemotactic activity for monocytes and THP-1 monocytes, but not for resting lymphocytes and neutrophils. Induces a calcium flux in THP-1 cells that were desensitized by prior expression to RANTES. |

TABLE 1 -continued

Amino acid sequences of physiological active peptides with an N-terminal glutamine residue, which are prone to be cyclized to final pGlu

| Peptide | Amino acid sequence | Function |
| --- | --- | --- |
| CCL8 (small inducible cytokine A8) Swiss-Prot: P80075 | QPDSVSI PITCCFNVIN RKIPIQRLES YTRITNIQCP KEAVIFKTKR GKEVCADPKE RWVRDSMKHL DQIFQNLKP | Chemotactic factor that attracts monocytes, lymphocytes, basophils and eosinophils. May play a role in neoplasia and inflammatory host responses. This protein can bind heparin. |
| CCL2 (MCP-1, small inducible cytokine A2) Swiss-Prot: P13500 | QPDAINA PVTCCYNFTN RKISVQRLAS YRRITSSKCP KEAVIFKTIV AKEICADPKQ KWVQDSMDHL DKQTQTPKT | Chemotactic factor that attracts monocytes and basophils but not neutrophils or eosinophils. Augments monocyte anti-tumor activity. Has been implicated in the pathogenesis of diseases characterized by monocytic infiltrates, like psoriasis, rheumatoid arthritis or atherosclerosis. May be involved in the recruitment of monocytes into the arterial wall during the disease process of atherosclerosis. Binds to CCR2 and CCR4. |
| CCL18 (small inducible cytokine A18) Swiss-Prot: P55774 | QVGTNKELC CLVYTSWQIP QKFIVDYSET SPQCPKPGVI LLTKRGRQIC ADPNKKWVQK YISDLKLNA | Chemotactic factor that attracts lymphocytes but not monocytes or granulocytes. May be involved in B cell migration into B cell follicles in lymph nodes. Attracts naive T lymphocytes toward dendritic cells and activated macrophages in lymph nodes, has chemotactic activity for naive T cells, CD4+ and CD8+ T cells and thus may play a role in both humoral and cell-mediated immunity responses. |
| Fractalkine (neurotactin) Swiss-Prot: P78423 | QHHGVT KCNITCSKMT SKIPVALLIH YQQNQASCGK RAIILETRQH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP VGTELFRVPP VSTAATWQSS APHQPGPSLW AEAKTSEAPS TQDPSTQAST ASSPAPEENA PSEGQRVWGQ GQSPRPENSL EREEMGPVPA HTDAFQDWGP GSMAHVSVVP VSSEGTPSRE PVASGSWTPK AEEPIHATMD PQRLGVLITP VPDAQAATRR QAVGLLAFLG LLFCLGVAMF TYQSLQGCPR KMAGEMAEGL RYIPRSCGSN SYVLVPV | The soluble form is chemotactic for T cells and monocytes, but not for neutrophils. The membrane-bound form promotes adhesion of those leukocytes to endothelial cells. May play a role in regulating leukocyte adhesion and migration processes at the endothelium binds to CX3CR1. |
| CCL7 (small inducible A7) cytokine Swiss-Prot: P80098 | QPVGINT STTCCYRFIN KKIPKQRLES YRRTTSSHCP REAVIFKTKL DKEICADPTQ KWVQDFMKHL DKKTQTPKL | Chemotactic factor that attracts monocytes and eosinophils, but not neutrophils. Augments monocyte anti-tumor activity. Also induces the release of gelatinase B. This protein can bind heparin. Binds to CCR1, CCR2 and CCR3. |
| Orexin A (Hypocretin-1) Swiss-Prot O43612 | QPLPDCCRQK TCSCRLYELL HGAGNHAAGI LTL | Neuropeptide that plays a significant role in the regulation of food intake and sleep wakefulness, possibly by coordinating the complex behavioral and physiologic responses of these complementary homeostatic functions. It plays also a broader role in the |

TABLE 1 -continued

Amino acid sequences of physiological active peptides with an N-terminal
glutamine residue, which are prone to be cyclized to final pGlu

| Peptide | Amino acid sequence | Function |
|---|---|---|
| | | homeostatic regulation of energy metabolism, autonomic function, hormonal balance and the regulation of body fluids. Orexin-A binds to both OX1R and OX2R with a high affinity. |
| Substance P | RPK PQQFFGLM | Belongs to the tachykinins. Tachykinins are active peptides which excite neurons, evoke behavioral responses, are potent vasodilators and secretagogues, and contract (directly or indirectly) many smooth muscles. |
| QYNAD | Gln-Tyr-Asn-Ala-Asp | Acts on voltage-gated sodium channels. |

Glutamate is found in positions 3, 11 and 22 of the amyloid O-peptide. Among them the mutation from glutamic acid (E) to glutamine (Q) in position 22 (corresponding to amyloid precursor protein APP 693, Swissprot PO5067) has been described as the so called Dutch type cerebroarterial amyloidosis mutation.

The β-amyloid peptides with a pyroglutamic acid residue in position 3, 11 and/or 22 have been described to be more cytotoxic and hydrophobic than the amyloid O-peptides 1-40 (42/43) (Saido T. C. 2000 Medical Hypotheses 54(3): 427-429).

The multiple N-terminal variations, e.g. Abeta(3-40), Abeta(3-42), Abeta(11-40) and Abeta (11-42) can be generated by the 6-secretase enzyme 6-site amyloid precursor protein-cleaving enzyme (BACE) at different sites (Huse J. T. et al. 2002 J. Biol. Chem. 277 (18): 16278-16284), and/or by aminopeptidase or dipeptidylaminopeptidase processing from the full length peptides Abeta(1-40) and Abeta(1-42). In all cases, cyclization of the then N-terminal occurring glutamic acid residue is catalyzed by QC.

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with Helicobacter pylori, who are known to have increased risk of duodenal ulcer disease and gastric cancer (Dockray, G. J. 1999 J Physiol 15 315-324).

The peptide hormone gastrin, released from antral G cells, is known to stimulate the synthesis and release of histamine from ECL cells in the oxyntic mucosa via CCK-2 receptors. The mobilized histamine induces acid secretion by binding to the H(2) receptors located on parietal cells. Recent studies suggest that gastrin, in both its fully amidated and less processed forms (progastrin and glycine-extended gastrin), is also a growth factor for the gastrointestinal tract. It has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g. glycine-extended gastrin) appears to be the colonic mucosa (Koh, T. J. and Chen, D. 2000 Regul Pept 9337-44).

Neurotensin (NT) is a neuropeptide implicated in the pathophysiology of schizophrenia that specifically modulates neurotransmitter systems previously demonstrated to be mis-regulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 Biol Psychiatry 50 856-872).

Fertilization promoting peptide (FPP), a tripeptide related to thyrotrophin releasing hormone (TRH), is found in seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on", others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 Vitam Horm 63, 1-28).

CCL2 (MCP-1), CCL7, CCL8, CCL16, CCL18 and fractalkine play an important role in pathophysiological conditions, such as suppression of proliferation of myeloid progenitor cells, neoplasia, inflammatory host responses, cancer, psoriasis, rheumatoid arthritis, atherosclerosis, vasculitis, humoral and cell-mediated immunity responses, leukocyte adhesion and migration processes at the endothelium, inflammatory bowel disease, restenosis, pulmonary fibrosis, pulmonary hypertention, liver fibrosis, liver cirrhosis, nephrosclerosis, ventricular remodeling, heart failure, arteriopathy after organ transplantations and failure of vein grafts.

A number of studies have underlined in particular the crucial role of MCP-1 for the development of atherosclerosis (Gu, L., et al., (1998) *Mol. Cell* 2, 275-281; Gosling, J., et al., (1999) *J. Clin. Invest* 103, 773-778); rheumatoid arthritis (Gong, J. H., et al., (1997) *J. Exp. Med* 186, 131-137; Ogata, H., et al., (1997) *J Pathol.* 182, 106-114); pancreatitis (Bhatia, M., et al., (2005) *Am. J Physiol Gastrointest. Liver Physiol* 288, G1259-G1265); Alzheimer's disease (Yamamoto, M., et al., (2005) *Am. J Pathol.* 166, 1475-1485); lung fibrosis (Inoshima, I., et al., (2004) *Am. J Physiol Lung Cell Mol. Physiol* 286, L1038-L1044); renal fibrosis (Wada, T., et al., (2004) *J. Am. Soc. Nephrol.* 15, 940-948), and graft rejection (Saiura, A., et al., (2004) *Arterioscler. Thromb. Vasc. Biol.* 24, 1886-1890). Furthermore, MCP-1 might also play a role in gestosis (Katabuchi, H., et al., (2003) *Med Electron Microsc.* 36, 253-262), as a paracrine factor in tumor development (Ohta, M., et al., (2003) *Int. J Oncol.* 22, 773-778; Li, S., et al., (2005) *J. Exp. Med* 202, 617-624), neuropathic pain (White, F. A., et al., (2005) *Proc. Natl. Acad. Sci. U.S.A*) and AIDS (Park, I. W., Wang, J. F., and Groopman, J. E. (2001) *Blood* 97, 352-358; Coll, B., et al., (2006) *Cytokine* 34, 51-55).

MCP-1 levels are increased in CSF of AD patients and patients showing mild cognitive impairment (MCI) (Galimberti, D., et al., (2006) *Arch. Neurol.* 63, 538-543). Furthermore, MCP-1 shows an increased level in serum of patients with MC1 and early AD (Clerici, F., et al., (2006) *Neurobiol. Aging* 27, 1763-1768).

Several cytotoxic T lymphocyte peptide-based vaccines against hepatitis B, human immunodeficiency virus and melanoma were recently studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class I major histocompatibility complex. Consequently, in order to conserve full activity of ELA, the formation of PyrELA must be avoided (Beck A. et al. 2001, *J Pept Res* 57(6):528-38.).

Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

Recently, increased levels of the pentapeptide QYNAD were identified in the cerebrospinal fluid (CSF) of patients suffering from multiple sclerosis or Guillain-Barré syndrome compared to healthy individuals (Brinkmeier H. et al. 2000, Nature Medicine 6, 808-811). There is a big controversy in the literature about the mechanism of action of the pentapeptide Gln-Tyr-Asn-Ala-Asp (QYNAD), especially its efficacy to interact with and block sodium channels resulting in the promotion of axonal dysfunction, which are involved in inflammatory autoimmune diseases of the central nervous system. But recently, it could be demonstrated that not QYNAD, but its cyclized, pyroglutamated form, pEYNAD, is the active form, which blocks sodium channels resulting in the promotion of axonal dysfunction. Sodium channels are expressed at high density in myelinated axons and play an obligatory role in conducting action potentials along axons within the mammalian brain and spinal cord. Therefore, it is speculated that they are involved in several aspects of the pathophysiology of inflammatory autoimmune diseases, especially multiple sclerosis, the Guillain-Barré syndrome and chronic inflammatory demyelinizing polyradiculoneuropathy.

Furthermore, QYNAD is a substrate of the enzyme glutaminyl cyclase (QC, EC 2.3.2.5), which is also present in the brain of mammals, especially in human brain. Glutaminyl cyclase catalyzes effectively the formation of pEYNAD from its precursor QYNAD.

Accordingly, the present invention provides the use of the compounds of formula (I) for the preparation of a medicament for the prevention or alleviation or treatment of a disease selected from the group consisting of mild cognitive impairment, Alzheimer's disease, Familial British Dementia, Familial Danish Dementia, neurodegeneration in Down Syndrome, Huntington's disease, Kennedy's disease, ulcer disease, duodenal cancer with or w/o *Helicobacter pylori* infections, colorectal cancer, Zolliger-Ellison syndrome, gastric cancer with or without *Helicobacter pylori* infections, pathogenic psychotic conditions, schizophrenia, infertility, neoplasia, inflammatory host responses, cancer, malign metastasis, melanoma, psoriasis, rheumatoid arthritis, atherosclerosis, pancreatitis, restenosis, impaired humoral and cell-mediated immune responses, leukocyte adhesion and migration processes in the endothelium, impaired food intake, impaired sleep-wakefulness, impaired homeostatic regulation of energy metabolism, impaired autonomic function, impaired hormonal balance or impaired regulation of body fluids, multiple sclerosis, the Guillain-Barré syndrome and chronic inflammatory demyelinizing polyradiculoneuropathy.

Furthermore, by administration of a compound according to the present invention to a mammal it can be possible to stimulate the proliferation of myeloid progenitor cells.

In addition, the administration of a QC inhibitor according to the present invention can lead to suppression of male fertility.

In a preferred embodiment, the present invention provides the use of inhibitors of QC (EC) activity in combination with other agents, especially for the treatment of neuronal diseases, artherosclerosis and multiple sclerosis.

The present invention also provides a method of treatment of the aforementioned diseases comprising the administration of a therapeutically active amount of at least one compound of formula (I) to a mammal, preferably a human.

Most preferably, said method and corresponding uses are for the treatment of a disease selected from the group consisting of mild cognitive impairment, Alzheimer's disease, Familial British Dementia, Familial Danish Dementia, neurodegeneration in Down Syndrome, Parkinson's disease and Chorea Huntington, comprising the administration of a therapeutically active amount of at least one compound of formula (I) to a mammal, preferably a human.

Even preferably, the present invention provides a method of treatment and corresponding uses for the treatment of rheumatoid arthritis, atherosclerosis, pancreatitis and restenosis.

Pharmaceutical Combinations

In a preferred embodiment, the present invention provides a composition, preferably a pharmaceutical composition, comprising at least one QC inhibitor optionally in combination with at least one other agent selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

Most preferably, said QC inhibitor is a compound of formula (I) of the present invention.

More specifically, the aforementioned other agent is selected from the group consisting of beta-amyloid antibodies, cysteine protease inhibitors, PEP-inhibitors, LiCl, acetylcholinesterase (AChE) inhibitors, PIMT enhancers, inhibitors of beta secretases, inhibitors of gamma secretases, inhibitors of aminopeptidases, preferably inhibitors of dipeptidyl peptidases, most preferably DP IV inhibitors; inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents, MCP-1 antagonists or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

Furthermore, the other agent may be, for example, an anti-anxiety drug or antidepressant selected from the group consisting of
  (a) Benzodiazepines, e.g. alprazolam, chlordiazepoxide, clobazam, clonazepam, clorazepate, diazepam, fludiazepam, loflazepate, lorazepam, methaqualone, oxazepam, prazepam, tranxene,
  (b) Selective serotonin re-uptake inhibitors (SSRI's), e.g. citalopram, fluoxetine, fluvoxamine, escitalopram, sertraline, paroxetine,
  (c) Tricyclic antidepressants, e.g. amitryptiline, clomipramine, desipramine, doxepin, imipramine
  (d) Monoamine oxidase (MAO) inhibitors,
  (e) Azapirones, e.g. buspirone, tandospirone,
  (f) Serotonin-norepinephrine reuptake inhibitors (SNRI's), e.g. venlafaxine, duloxetine,
  (g) Mirtazapine,
  (h) Norepinephrine reuptake inhibitors (NRI's), e.g. reboxetine,
  (i) Bupropione,
  (j) Nefazodone,
  (k) beta-blockers,
  (l) NPY-receptor ligands: NPY agonists or antagonists.

In a further embodiment, the other agent may be, for example, an anti-multiple sclerosis drug selected from the group consisting of
  a) dihydroorotate dehydrogenase inhibitors, e.g. SC-12267, teriflunomide, MNA-715, HMR-1279 (syn. to HMR-1715, MNA-279),
  b) autoimmune suppressant, e.g. laquinimod,
  c) paclitaxel,
  d) antibodies, e.g. AGT-1, anti-granulocyte-macrophage colony-stimulating factor (GM-CSF) monoclonal antibody, Nogo receptor modulators, ABT-874, alemtuzumab (CAMPATH), anti-OX40 antibody, CNTO-1275, DN-1921, natalizumab (syn. to AN-100226, Antegren, VLA-4 Mab), daclizumab (syn. to Zenepax, Ro-34-7375, SMART anti-Tac), J-695, priliximab (syn. to Centara, CEN-000029, cM-T412), MRA, Dantes, anti-IL-12-antibody,
  e) peptide nucleic acid (PNA) preparations, e.g. reticulose,
  f) interferon alpha, e.g. Alfaferone, human alpha interferon (syn. to Omniferon, Alpha Leukoferon),
  g) interferon beta, e.g. Frone, interferon beta-1a like Avonex, Betron (Rebif), interferon beta analogs, interferon beta-transferrin fusion protein, recombinant interferon beta-1b like Betaseron,
  h) interferon tau,
  i) peptides, e.g. AT-008, AnergiX.MS, Immunokine (alpha-Immunokine-NNSO3), cyclic peptides like ZD-7349,
  j) therapeutic enzymes, e.g. soluble CD8 (sCD8),
  k) multiple sclerosis-specific autoantigen-encoding plasmid and cytokine-encoding plasmid, e.g. BHT-3009;
  l) inhibitor of TNF-alpha, e.g. BLX-1002, thalidomide, SH-636,
  m) TNF antagonists, e.g. solimastat, lenercept (syn. to RO-45-2081, Tenefuse), onercept (sTNFR1), CC-1069,
  n) TNF alpha, e.g. etanercept (syn. to Enbrel, TNR-001)
  o) CD28 antagonists, e.g. abatacept,
  p) Lck tyrosine kinase inhibitors,
  q) cathepsin K inhibitors,
  r) analogs of the neuron-targeting membrane transporter protein taurine and the plant-derived calpain inhibitor leupeptin, e.g. Neurodur,
  s) chemokine receptor-1 (CCR1) antagonist, e.g. BX-471,
  t) CCR2 antagonists,
  u) AMPA receptor antagonists, e.g. ER-167288-01 and ER-099487, E-2007, talampanel,
  v) potassium channel blockers, e.g. fampridine,
  w) tosyl-proline-phenylalanine small-molecule antagonists of the VLA-4/VCAM interaction, e.g. TBC-3342,
  x) cell adhesion molecule inhibitors, e.g. TBC-772,
  y) antisense oligonucleotides, e.g. EN-101,
  z) antagonists of free immunoglobulin light chain (IgLC) binding to mast cell receptors, e.g. F-991,
  aa) apoptosis inducing antigens, e.g. Apogen MS,
  bb) alpha-2 adrenoceptor agonist, e.g. tizanidine (syn. to Zanaflex, Ternelin, Sirdalvo, Sirdalud, Mionidine),
  cc) copolymer of L-tyrosine, L-lysine, L-glutamic acid and L-alanine, e.g. glatiramer acetate (syn. to Copaxone, COP-1, copolymer-1),
  dd) topoisomerase II modulators, e.g. mitoxantrone hydrochloride, ee) adenosine deaminase inhibitor, e.g. cladribine (syn. to Leustatin, Mylinax, RWJ-26251),
ff) interleukin-10, e.g. ilodecakin (syn. to Tenovil, Sch-52000, CSIF),
gg) interleukin-12 antagonists, e.g. lisofylline (syn. to CT-1501R, LSF, lysofylline),
hh) Ethanaminum, e.g. SR1-62-834 (syn. to CRC-8605, NSC-614383),
ii) immunomodulators, e.g. SAIK-MS, PNU-156804, alpha-fetoprotein peptide (AFP), IPDS,
jj) retinoid receptor agonists, e.g. adapalene (syn. to Differin, CD-271),
kk) TGF-beta, e.g. GDF-1 (growth and differentiation factor 1),
ll) TGF-beta-2, e.g. BetaKine,
mm) MMP inhibitors, e.g. glycomed,
nn) phosphodiesterase 4 (PDE4) inhibitors, e.g. RPR-122818,
oo) purine nucleoside phosphorylase inhibitors, e.g. 9-(3-pyridylmethyl)-9-deazaguanine, peldesine (syn. to BCX-34, TO-200),
pp) alpha-4/beta-1 integrin antagonists, e.g. ISIS-104278,
qq) antisense alpha4 integrin (CD49d), e.g. ISIS-17044, ISIS-27104,
rr) cytokine-inducing agents, e.g. nucleosides, ICN-17261,
ss) cytokine inhibitors,
tt) heat shock protein vaccines, e.g. HSPPC-96,
uu) neuregulin growth factors, e.g. GGF-2 (syn. to neuregulin, glial growth factor 2),
vv) cathepsin S-inhibitors,
ww) bropirimine analogs, e.g. PNU-56169, PNU-63693,
xx) Monocyte chemoattractant protein-1 inhibitors, e.g. benzimidazoles like MCP-1 inhibitors, LKS-1456, PD-064036, PD-064126, PD-084486, PD-172084, PD-172386.

Further, the present invention provides pharmaceutical compositions e.g. for parenteral, enteral or oral administration, comprising at least one QC inhibitor, optionally in combination with at least one of the other aforementioned agents.

These combinations provide a particularly beneficial effect. Such combinations are therefore shown to be effective and useful for the treatment of the aforementioned diseases. Accordingly, the invention provides a method for the treatment of these conditions.

The method comprises either co-administration of at least one QC inhibitor and at least one of the other agents or the sequential administration thereof.

Co-administration includes administration of a formulation, which comprises at least one QC inhibitor and at least one of the other agents or the essentially simultaneous administration of separate formulations of each agent.

Beta-amyloid antibodies and compositions containing the same are described, e.g. in WO 2006/137354, WO 2006/118959, WO 2006/103116, WO 2006/095041, WO 2006/081171, WO 2006/066233, WO 2006/066171, WO 2006/066089, WO 2006/066049, WO 2006/055178, WO 2006/046644, WO 2006/039470, WO 2006/036291, WO 2006/026408, WO 2006/016644, WO 2006/014638, WO 2006/014478, WO 2006/008661, WO 2005/123775, WO 2005/120571, WO 2005/105998, WO 2005/081872, WO 2005/080435, WO 2005/028511, WO 2005/025616, WO 2005/025516, WO 2005/023858, WO 2005/018424, WO 2005/011599, WO 2005/000193, WO 2004/108895, WO 2004/098631, WO 2004/080419, WO 2004/071408, WO 2004/069182, WO 2004/067561, WO 2004/044204, WO 2004/032868, WO 2004/031400, WO 2004/029630, WO 2004/029629, WO 2004/024770, WO 2004/024090, WO 2003/104437, WO 2003/089460, WO 2003/086310, WO 2003/077858, WO 2003/074081, WO 2003/070760, WO 2003/063760, WO 2003/055514, WO 2003/051374, WO 2003/048204, WO 2003/045128, WO 2003/040183, WO 2003/039467, WO 2003/016466, WO 2003/015691, WO 2003/014162, WO 2003/012141, WO 2002/088307, WO 2002/088306, WO 2002/074240, WO 2002/046237, WO 2002/046222, WO 2002/041842, WO 2001/062801, WO 2001/012598, WO 2000/077178, WO 2000/072880, WO 2000/063250, WO 1999/060024, WO 1999/027944, WO 1998/044955, WO 1996/025435, WO 1994/017197, WO 1990/014840, WO 1990/012871, WO 1990/012870, WO 1989/006242.

The beta-amyloid antibodies may be selected from, for example, polyclonal, monoclonal, chimenic or humanized antibodies. Furthermore, said antibodies may be useful to develop active and passive immune therapies, i.e. vaccines and monoclonal antibodies. Suitable examples of beta-amyloid antibodies are ACU-5A5, huC091 (Acumen/Merck); PF-4360365, RI-1014, RI-1219, RI-409, RN-1219 (Rinat Neuroscience Corp (Pfizer Inc)); the nanobody therapeutics of Ablynx/Boehringer Ingelheim; beta-amyloid-specific humanized monoclonal antibodies of Intellect Neurosciences/IBL; m266, m266.2 (Eli Lilly & Co.); AAB-02 (Elan); bapineuzumab (Elan); BAN-2401 (Bioarctic Neuroscience AB); ABP-102 (Abiogen Pharma SpA); BA-27, BC-05 (Takeda); R-1450 (Roche); ESBA-212 (ESBATech AG); AZD-3102 (AstraZeneca) and beta-amyloid antibodies of Mindset BioPharmaceuticals Inc.

Especially preferred are antibodies, which recognize the N-terminus of the Aβ peptide. A suitable antibody, which recognizes the Aβ-N-Terminus is, for example Acl-24 (AC Immune SA).

A monoclonal antibody against beta-amyloid peptide is disclosed in WO 2007/068412. Respective chimeric and humanized antibodies are disclosed in WO 2008/011348. A method for producing a vaccine composition for treating an amyloid-associated disease is disclosed in WO 2007/068411.

Suitable cysteine protease inhibitors are inhibitors of cathepsin B. Inhibitors of cathepsin B and compositions containing such inhibitors are described, e.g. in WO 2006/060473, WO 2006/042103, WO 2006/039807, WO 2006/021413, WO 2006/021409, WO 2005/097103, WO 2005/007199, WO2004/084830, WO 2004/078908, WO 2004/026851, WO 2002/094881, WO 2002/027418, WO 2002/021509, WO 1998/046559, WO 1996/021655.

Examples of suitable PIMT enhancers are 10-aminoaliphatyl-dibenz[b,f]oxepines described in WO 98/15647 and WO 03/057204, respectively. Further useful according to the present invention are modulators of PIMT activity described in WO 2004/039773.

Inhibitors of beta secretase and compositions containing such inhibitors are described, e.g. in WO03/059346, WO2006/099352, WO2006/078576, WO2006/060109, WO2006/057983, WO2006/057945, WO2006/055434, WO2006/044497, WO2006/034296, WO2006/034277, WO2006/029850, WO2006/026204, WO2006/014944, WO2006/014762, WO2006/002004, U.S. Pat. No. 7,109,217, WO2005/113484, WO2005/103043, WO2005/103020, WO2005/065195, WO2005/051914, WO2005/044830, WO2005/032471, WO2005/018545, WO2005/004803, WO2005/004802, WO2004/062625, WO2004/043916, WO2004/013098, WO03/099202, WO03/043987, WO03/039454, U.S. Pat. No. 6,562,783, WO02/098849 and WO02/096897.

Suitable examples of beta secretase inhibitors for the purpose of the present invention are WY-25105 (Wyeth);

Posiphen, (+)-phenserine (TorreyPines/NIH); LSN-2434074, LY-2070275, LY-2070273, LY-2070102 (Eli Lilly & Co.); PNU-159775A, PNU-178025A, PNU-17820A, PNU-33312, PNU-38773, PNU-90530 (Elan/Pfizer); KMI-370, KMI-358, kmi-008 (Kyoto University); OM-99-2, OM-003 (Athenagen Inc.); AZ-12304146 (AstraZeneca/Astex); GW-840736X (GlaxoSmithKline plc.), DNP-004089 (De Novo Pharmaceuticals Ltd.) and CT-21166 (CoMentis Inc.).

Inhibitors of gamma secretase and compositions containing such inhibitors are described, e.g. in WO2005/008250, WO2006/004880, U.S. Pat. Nos. 7,122,675, 7,030,239, 6,992,081, 6,982,264, WO2005/097768, WO2005/028440, WO2004/101562, U.S. Pat. Nos. 6,756,511, 6,683,091, WO03/066592, WO03/014075, WO03/013527, WO02/36555, WO01/53255, U.S. Pat. Nos. 7,109,217, 7,101,895, 7,049,296, 7,034,182, 6,984,626, WO2005/040126, WO2005/030731, WO2005/014553, U.S. Pat. No. 6,890,956, EP 1334085, EP 1263774, WO2004/101538, WO2004/00958, WO2004/089911, WO2004/073630, WO2004/069826, WO2004/039370, WO2004/031139, WO2004/031137, U.S. Pat. Nos. 6,713,276, 6,686,449, WO03/091278, U.S. Pat. Nos. 6,649,196, 6,448,229, WO01/77144 and WO01/66564.

Suitable gamma secretase inhibitors for the purpose of the present invention are GSI-953, WAY-GSI-A, WAY-GSI-B (Wyeth); MK-0752, MRK-560, L-852505, L-685-458, L-852631, L-852646 (Merck & Co. Inc.); LY-450139, LY-411575, AN-37124 (Eli Lilly & Co.); BMS-299897, BMS-433796 (Bristol-Myers Squibb Co.); E-2012 (Eisai Co. Ltd.); EHT-0206, EHT-206 (ExonHit Therapeutics SA); and NGX-555 (TorreyPines Therapeutics Inc.).

DP IV-inhibitors and compositions containing such inhibitors are described, e.g. in U.S. Pat. Nos. 6,011,155; 6,107,317; 6,110,949; 6,124,305; 6,172,081; WO99/61431, WO99/67278, WO99/67279, DE19834591, WO97/40832, WO95/15309, WO98/19998, WO00/07617, WO99/38501, WO99/46272, WO99/38501, WO01/68603, WO01/40180, WO01/81337, WO01/81304, WO01/55105, WO02/02560, WO01/34594, WO02/38541, WO02/083128, WO03/072556, WO03/002593, WO03/000250, WO03/000180, WO03/000181, EP1258476, WO03/002553, WO03/002531, WO03/002530, WO03/004496, WO03/004498, WO03/024942, WO03/024965, WO03/033524, WO03/035057, WO03/035067, WO03/037327, WO03/040174, WO03/045977, WO03/055881, WO03/057144, WO03/057666, WO03/068748, WO03/068757, WO03/082817, WO03/101449, WO03/101958, WO03/104229, WO03/74500, WO2004/007446, WO2004/007468, WO2004/018467, WO2004/018468, WO2004/018469, WO2004/026822, WO2004/032836, WO2004/033455, WO2004/037169, WO2004/041795, WO2004/043940, WO2004/048352, WO2004/050022, WO2004/052850, WO2004/058266, WO2004/064778, WO2004/069162, WO2004/071454, WO2004/076433, WO2004/076434, WO2004/087053, WO2004/089362, WO2004/099185, WO2004/103276, WO2004/103993, WO2004/108730, WO2004/110436, WO2004/111041, WO2004/112701, WO2005/000846, WO2005/000848, WO2005/011581, WO2005/016911, WO2005/023762, WO2005/025554, WO2005/026148, WO2005/030751, WO2005/033106, WO2005/037828, WO2005/040095, WO2005/044195, WO2005/047297, WO2005/051950, WO2005/056003, WO2005/056013, WO2005/058849, WO2005/075426, WO2005/082348, WO2005/085246, WO2005/087235, WO2005/095339, WO2005/095343, WO2005/095381, WO2005/108382, WO2005/113510, WO2005/116014, WO2005/116029, WO2005/118555, WO2005/120494, WO2005/121089, WO2005/121131, WO2005/123685, WO2006/995613; WO2006/009886; WO2006/013104; WO2006/017292; WO2006/019965; WO2006/020017; WO2006/023750; WO2006/039325; WO2006/041976; WO2006/047248; WO2006/058064; WO2006/058628; WO2006/066747; WO2006/066770 and WO2006/068978.

Suitable DP IV-inhibitors for the purpose of the present invention are for example Sitagliptin, des-fluoro-sitagliptin (Merck & Co. Inc.); vildagliptin, DPP-728, SDZ-272-070 (Novartis); ABT-279, ABT-341 (Abbott Laboratories); denagliptin, TA-6666 (GlaxoSmithKline plc.); SYR-322 (Takeda San Diego Inc.); talabostat (Point Therapeutics Inc.); Ro-0730699, R-1499, R-1438 (Roche Holding AG); FE-999011 (Ferring Pharmaceuticals); TS-021 (Taisho Pharmaceutical Co. Ltd.); GRC-8200 (Glenmark Pharmaceuticals Ltd.); ALS-2-0426 (Alantos Pharmaceuticals Holding Inc.); ARI-2243 (Arisaph Pharmaceuticals Inc.); SSR-162369 (Sanofi-Synthelabo); MP-513 (Mitsubishi Pharma Corp.); DP-893, CP-867534-01 (Pfizer Inc.); TSL-225, TMC-2A (Tanabe Seiyaku Co. Ltd.); PHX-1149 (Phenomenix Corp.); saxagliptin (Bristol-Myers Squibb Co.); PSN-9301 ((OSI) Prosidion), S-40755 (Servier); KRP-104 (ActivX Biosciences Inc.); sulphostin (Zaidan Hojin); KR-62436 (Korea Research Institute of Chemical Technology); P32/98 (Probiodrug AG); BI-A, BI-B (Boehringer Ingelheim Corp.); SK-0403 (Sanwa Kagaku Kenkyusho Co. Ltd.); and NNC-72-2138 (Novo Nordisk NS).

Other preferred DP IV-inhibitors are
(i) dipeptide-like compounds, disclosed in WO 99/61431, e.g. N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof;
(ii) peptide structures, disclosed in WO 03/002593, e.g. tripeptides;
(iii) peptidylketones, disclosed in WO 03/033524;
(vi) substituted aminoketones, disclosed in WO 03/040174;
(v) topically active DP IV-inhibitors, disclosed in WO 01/14318;
(vi) prodrugs of DP IV-inhibitors, disclosed in WO 99/67278 and WO 99/67279; and
(v) glutaminyl based DP IV-inhibitors, disclosed in WO 03/072556 and WO 2004/099134.

Suitable beta amyloid synthesis inhibitors for the purpose of the present invention are for example Bisnorcymserine (Axonyx Inc.); (R)-flurbiprofen (MCP-7869; Flurizan) (Myriad Genetics); nitroflurbiprofen (NicOx); BGC-20-0406 (Sankyo Co. Ltd.) and BGC-20-0466 (BTG plc.).

Suitable amyloid protein deposition inhibitors for the purpose of the present invention are for example SP-233 (Samaritan Pharmaceuticals); AZD-103 (Ellipsis Neurotherapeutics Inc.); AAB-001 (Bapineuzumab), AAB-002, ACC-001 (Elan Corp plc.); Colostrinin (ReGen Therapeutics plc.); Tramiprosate (Neurochem); AdPEDI-(amyloid-beta1-6)11) (Vaxin Inc.); MPI-127585, MPI-423948 (Mayo Foundation); SP-08 (Georgetown University); ACU-5A5 (Acumen/Merck); Transthyretin (State University of New York); PTI-777, DP-74, DP 68, Exebryl (ProteoTech Inc.); m266 (Eli Lilly & Co.); EGb-761 (Dr. Willmar Schwabe GmbH); SPI-014 (Satori Pharmaceuticals Inc.); ALS-633, ALS-499 (Advanced Life Sciences Inc.); AGT-160 (ArmaGen Technologies Inc.); TAK-070 (Takeda Pharmaceutical Co. Ltd.); CHF-5022, CHF-5074, CHF-5096 and CHF-5105 (Chiesi Farmaceutici SpA.).

Suitable PDE-4 inhibitors for the purpose of the present invention are for example Doxofylline (Instituto Biologico Chemioterapica ABC SpA.); idudilast eye drops, tipelukast, ibudilast (Kyorin Pharmaceutical Co. Ltd.); theophylline (Elan Corp.); cilomilast (GlaxoSmithKline plc.); Atopik (Barrier Therapeutics Inc.); tofimilast, CI-1044, PD-189659, CP-220629, PDE 4d inhibitor BHN (Pfizer Inc.); arofylline, LAS-37779 (Almirall Prodesfarma SA.); roflumilast, hydroxypumafentrine (Altana AG), tetomilast (Otska Pharmaceutical Co. Ltd.); tipelukast, ibudilast (Kyorin Pharmaceutical), CC-10004 (Celgene Corp.); HT-0712, IPL-4088 (Inflazyme Pharmaceuticals Ltd.); MEM-1414, MEM-1917 (Memory Pharmaceuticals Corp.); oglemilast, GRC-4039 (Glenmark Pharmaceuticals Ltd.); AWD-12-281, ELB-353, ELB-526 (Elbion AG); EHT-0202 (ExonHit Therapeutics SA.); ND-1251 (Neuro3d SA.); 4AZA-PDE4 (4 AZA Bioscience NV.); AVE-8112 (Sanofi-Aventis); CR-3465 (Rottapharm SpA.); GP-0203, NCS-613 (Centre National de la Recherche Scientifique); KF-19514 (Kyowa Hakko Kogyo Co. Ltd.); ONO-6126 (Ono Pharmaceutical Co. Ltd.); OS-0217 (Dainippon Pharmaceutical Co. Ltd.); IBFB-130011, IBFB-150007, IBFB-130020, IBFB-140301 (IBFB Pharma GmbH); IC-485 (ICOS Corp.); RBx-14016 and RBx-11082 (Ranbaxy Laboratories Ltd.). A preferred PDE-4-inhibitor is Rolipram.

MAO inhibitors and compositions containing such inhibitors are described, e.g. in WO2006/091988, WO2005/007614, WO2004/089351, WO01/26656, WO01/12176, WO99/57120, WO99/57119, WO99/13878, WO98/40102, WO98/01157, WO96/20946, WO94/07890 and WO92/21333.

Suitable MAO-inhibitors for the purpose of the present invention are for example Linezolid (Pharmacia Corp.); RWJ-416457 (RW Johnson Pharmaceutical Research Institute); budipine (Altana AG); GPX-325 (BioResearch Ireland); isocarboxazid; phenelzine; tranylcypromine; indantadol (Chiesi Farmaceutici SpA.); moclobemide (Roche Holding AG); SL-25.1131 (Sanofi-Synthelabo); CX-1370 (Burroughs Wellcome Co.); CX-157 (Krenitsky Pharmaceuticals Inc.); desoxypeganine (HF Arzneimittelforschung GmbH & Co. KG); bifemelane (Mitsubishi-Tokyo Pharmaceuticals Inc.); RS-1636 (Sankyo Co. Ltd.); esuprone (BASF AG); rasagiline (Teva Pharmaceutical Industries Ltd.); ladostigil (Hebrew University of Jerusalem); safinamide (Pfizer) and NW-1048 (Newron Pharmaceuticals SpA.).

Suitable histamine H3 antagonists for the purpose of the present invention are, e.g. ABT-239, ABT-834 (Abbott Laboratories); 3874-H1 (Aventis Pharma); UCL-2173 (Berlin Free University), UCL-1470 (BioProjet, Societe Civile de Recherche); DWP-302 (Daewoong Pharmaceutical Co Ltd); GSK-189254A, GSK-207040A (GlaxoSmithKline Inc.); cipralisant, GT-2203 (Gliatech Inc.); Ciproxifan (INSERM), 1S,2S-2-(2-Aminoethyl)-1-(1H-imidazol-4-yl)cyclopropane (Hokkaido University); JNJ-17216498, JNJ-5207852 (Johnson & Johnson); NNC-0038-0000-1049 (Novo Nordisk NS); and Sch-79687 (Schering-Plough).

PEP inhibitors and compositions containing such inhibitors are described, e.g. in JP 01042465, JP 03031298, JP 04208299, WO 00/71144, U.S. Pat. No. 5,847,155; JP 09040693, JP 10077300, JP 05331072, JP 05015314, WO 95/15310, WO 93/00361, EP 0556482, JP 06234693, JP 01068396, EP 0709373, U.S. Pat. Nos. 5,965,556, 5,756,763, 6,121,311, JP 63264454, JP 64000069, JP 63162672, EP 0268190, EP 0277588, EP 0275482, U.S. Pat. Nos. 4,977,180, 5,091,406, 4,983,624, 5,112,847, 5,100,904, 5,254,550, 5,262,431, 5,340,832, 4,956,380, EP 0303434, JP 03056486, JP 01143897, JP 1226880, EP 0280956, U.S. Pat. No. 4,857, 537, EP 0461677, EP 0345428, JP 02275858, U.S. Pat. No. 5,506,256, JP 06192298, EP 0618193, JP 03255080, EP 0468469, U.S. Pat. No. 5,118,811, JP 05025125, WO 9313065, JP 05201970, WO 9412474, EP 0670309, EP 0451547, JP 06339390, U.S. Pat. Nos. 5,073,549, 4,999,349, EP 0268281, U.S. Pat. No. 4,743,616, EP 0232849, EP 0224272, JP 62114978, JP 62114957, U.S. Pat. Nos. 4,757, 083, 4,810,721, 5,198,458, 4,826,870, EP 0201742, EP 0201741, U.S. Pat. No. 4,873,342, EP 0172458, JP 61037764, EP 0201743, U.S. Pat. No. 4,772,587, EP 0372484, U.S. Pat. No. 5,028,604, WO 91/18877, JP 04009367, JP 04235162, U.S. Pat. No. 5,407,950, WO 95/01352, JP 01250370, JP 02207070, U.S. Pat. No. 5,221, 752, EP 0468339, JP 04211648, WO 99/46272, WO 2006/058720 and PCT/EP2006/061428.

Suitable prolyl endopeptidase inhibitors for the purpose of the present invention are, e.g. Fmoc-Ala-Pyrr-CN, Z-Phe-Pro-Benzothiazole (Probiodrug), Z-321 (Zeria Pharmaceutical Co Ltd.); ONO-1603 (Ono Pharmaceutical Co Ltd); JTP-4819 (Japan Tobacco Inc.) and S-17092 (Servier).

Other suitable compounds that can be used according to the present invention in combination with QC-inhibitors are NPY, an NPY mimetic or an NPY agonist or antagonist or a ligand of the NPY receptors.

Preferred according to the present invention are antagonists of the NPY receptors.

Suitable ligands or antagonists of the NPY receptors are 3a,4,5,9b-tetrahydro-1h-benz[e]indol-2-yl amine-derived compounds as disclosed in WO 00/68197.

NPY receptor antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494 and WO 98/07420; WO 00/30674, U.S. Pat. Nos. 5,552,411, 5,663,192 and 5,567,714; 6,114,336, Japanese patent application JP 09157253; international patent applications WO 94/00486, WO 93/12139, WO 95/00161 and WO 99/15498; U.S. Pat. No. 5,328,899; German patent application DE 393 97 97; European patent applications EP 355 794 and EP 355 793; and Japanese patent applications JP 06116284 and JP 07267988. Preferred NPY antagonists include those compounds that are specifically disclosed in these patent documents. More preferred compounds include amino acid and non-peptide-based NPY antagonists. Amino acid and non-peptide-based NPY antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494, WO 98/07420 and WO 99/15498; U.S. Pat. Nos. 5,552,411, 5,663,192 and 5,567,714; and Japanese patent application JP 09157253. Preferred amino acid and non-peptide-based NPY antagonists include those compounds that are specifically disclosed in these patent documents.

Particularly preferred compounds include amino acid-based NPY antagonists. Amino acid-based compounds, which may be mentioned include those disclosed in international patent applications WO 94/17035, WO 97/19911, WO 97/19913, WO 97/19914 or, preferably, WO 99/15498. Preferred amino acid-based NPY antagonists include those that are specifically disclosed in these patent documents, for example BIBP3226 and, especially, (R)—N-2-(diphenylacetyl)-(R)—N-[1-(4-hydroxy-phenyl)ethyl]arginine amide (Example 4 of international patent application WO 99/15498).

M1 receptor agonists and compositions containing such inhibitors are described, e.g. in WO2004/087158, WO91/10664.

Suitable M1 receptor antagonists for the purpose of the present invention are for example CDD-0102 (Cognitive Pharmaceuticals); Cevimeline (Evoxac) (Snow Brand Milk Products Co. Ltd.); NGX-267 (TorreyPines Therapeutics); sabcomeline (GlaxoSmithKline); alvameline (H Lundbeck NS); LY-593093 (Eli Lilly & Co.); VRTX-3 (Vertex Pharmaceuticals Inc.); WAY-132983 (Wyeth) and CI-101 7/(PD-151832) (Pfizer Inc.).

Acetylcholinesterase inhibitors and compositions containing such inhibitors are described, e.g. in WO2006/071274, WO2006/070394, WO2006/040688, WO2005/092009, WO2005/079789, WO2005/039580, WO2005/027975, WO2004/084884, WO2004/037234, WO2004/032929, WO03/101458, WO03/091220, WO03/082820, WO03/020289, WO02/32412, WO01/85145, WO01/78728, WO01/66096, WO00/02549, WO01/00215, WO00/15205, WO00/23057, WO00/33840, WO00/30446, WO00/23057, WO00/15205, WO00/09483, WO00/07600, WO00/02549, WO99/47131, WO99/07359, WO98/30243, WO97/38993, WO97/13754, WO94/29255, WO94/20476, WO94/19356, WO93/03034 and WO92/19238.

Suitable acetylcholinesterase inhibitors for the purpose of the present invention are for example Donepezil (Eisai Co. Ltd.); rivastigmine (Novartis AG); (−)-phenserine (TorreyPines Therapeutics); ladostigil (Hebrew University of Jerusalem); huperzine A (Mayo Foundation); galantamine (Johnson & Johnson); Memoquin (Universita di Bologna); SP-004 (Samaritan Pharmaceuticals Inc.); BGC-20-1259 (Sankyo Co. Ltd.); physostigmine (Forest Laboratories Inc.); NP-0361 (Neuropharma SA); ZT-1 (Debiopharm); tacrine (Warner-Lambert Co.); metrifonate (Bayer Corp.) and INM-176 (Whanln).

NMDA receptor antagonists and compositions containing such inhibitors are described, e.g. in WO2006/094674, WO2006/058236, WO2006/058059, WO2006/010965, WO2005/000216, WO2005/102390, WO2005/079779, WO2005/079756, WO2005/072705, WO2005/070429, WO2005/055996, WO2005/035522, WO2005/009421, WO2005/000216, WO2004/092189, WO2004/039371, WO2004/028522, WO2004/009062, WO03/010159, WO02/072542, WO02/34718, WO01/98262, WO01/94321, WO01/92204, WO01/81295, WO01/32640, WO01/10833, WO01/10831, WO00/56711, WO00/29023, WO00/00197, WO99/53922, WO99/48891, WO99/45963, WO99/01416, WO99/07413, WO99/01416, WO98/50075, WO98/50044, WO98/10757, WO98/05337, WO97/32873, WO97/23216, WO97/23215, WO97/23214, WO96/14318, WO96/08485, WO95/31986, WO95/26352, WO95/26350, WO95/26349, WO95/26342, WO95/12594, WO95/02602, WO95/02601, WO94/20109, WO94/13641, WO94/09016 and WO93/25534.

Suitable NMDA receptor antagonists for the purpose of the present invention are for example Memantine (Merz & Co. GmbH); topiramate (Johnson & Johnson); AVP-923 (Neurodex) (Center for Neurologic Study); EN-3231 (Endo Pharmaceuticals Holdings Inc.); neramexane (MRZ-2/579) (Merz and Forest); CNS-5161 (CeNeS Pharmaceuticals Inc.); dexanabinol (HU-211; Sinnabidol; PA-50211) (Pharmos); EpiCept NP-1 (Dalhousie University); indantadol (V-3381; CNP-3381) (Vernalis); perzinfotel (EAA-090, WAY-126090, EAA-129) (Wyeth); RGH-896 (Gedeon Richter Ltd.); traxoprodil (CP-101606), besonprodil (PD-196860, CI-1041) (Pfizer Inc.); CGX-1007 (Cognetix Inc.); delucemine (NPS-1506) (NPS Pharmaceuticals Inc.); EVT-101 (Roche Holding AG); acamprosate (Synchroneuron LLC.); CR-3991, CR-2249, CR-3394 (Rottapharm SpA.); AV-101 (4-Cl-kynurenine (4-Cl-KYN)), 7-chloro-kynurenic acid (7-Cl-KYNA) (VistaGen); NPS-1407 (NPS Pharmaceuticals Inc.); YT-1006 (Yaupon Therapeutics Inc.); ED-1812 (Sosei R&D Ltd.); himantane (hydrochloride N-2-(adamantly)-hexamethylen-imine) (RAMS); Lancicemine (AR-R-15896) (AstraZeneca); EVT-102, Ro-25-6981 and Ro-63-1908 (Hoffmann-La Roche AG/Evotec).

Furthermore, the present invention relates to combination therapies useful for the treatment of atherosclerosis, restenosis or arthritis, administering a QC inhibitor in combination with another therapeutic agent selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors providing beneficial or synergistic therapeutic effects over each monotherapy component alone.

Angiotensin II receptor blockers are understood to be those active agents that bind to the AT1-receptor subtype of angiotensin II receptor but do not result in activation of the receptor. As a consequence of the blockade of the AT1 receptor, these antagonists can, e.g. be employed as antihypertensive agents.

Suitable angiotensin II receptor blockers which may be employed in the combination of the present invention include AT, receptor antagonists having differing structural features, preferred are those with non-peptidic structures. For example, mention may be made of the compounds that are selected from the group consisting of valsartan (EP 443983), losartan (EP 253310), candesartan (EP 459136), eprosartan (EP 403159), irbesartan (EP 454511), olmesartan (EP 503785), tasosartan (EP 539086), telmisartan (EP 522314), the compound with the designation E-41 77 of the formula

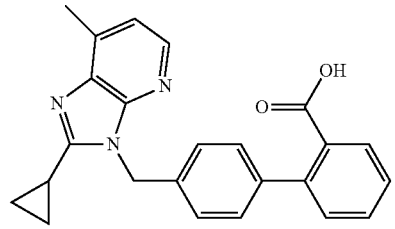 [SMILES: Cc1ccnc2c1nc(C1CC1)n2Cc1ccc(-c2ccccc2C(=O)O)cc1]

the compound with the designation SC-52458 of the following formula

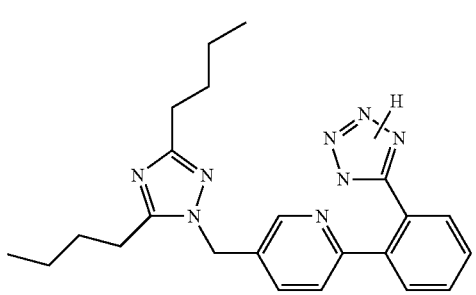

and the compound with the designation the compound ZD-8731 of the formula

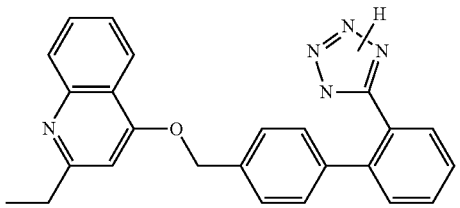

or, in each case, a pharmaceutically acceptable salt thereof.

Preferred AT1-receptor antagonists are those agents that have been approved and reached the market, most preferred is valsartan, or a pharmaceutically acceptable salt thereof.

The interruption of the enzymatic degradation of angiotensin to angiotensin II with ACE inhibitors is a successful variant for the regulation of blood pressure and thus also makes available a therapeutic method for the treatment of hypertension.

A suitable ACE inhibitor to be employed in the combination of the present invention is, e.g. a compound selected from the group consisting alacepril, benazepril, benazeprilat; captopril, ceronapril, cilazapril, delapril, enalapril, enaprilat, fosinopril, imidapril, lisinopril, moveltopril, perindopril, quinapril, ramipril, spirapril, temocapril and trandolapril, or in each case, a pharmaceutically acceptable salt thereof.

Preferred ACE inhibitors are those agents that have been marketed, most preferred are benazepril and enalapril.

A diuretic is, for example, a thiazide derivative selected from the group consisting of chlorothiazide, hydrochlorothiazide, methylclothiazide, and chlorothalidon. The most preferred diuretic is hydrochlorothiazide. A diuretic furthermore comprises a potassium sparing diuretic such as amiloride or triameterine, or a pharmaceutically acceptable salt thereof.

The class of CCBs essentially comprises dihydropyridines (DHPs) and non-DHPs, such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine and verapamil or, e.g. dependent on the specific CCB, a pharmaceutically acceptable salt thereof. Especially preferred as DHP is amlodipine or a pharmaceutically acceptable salt thereof, especially the besylate. An especially preferred representative of non-DHPs is verapamil or a pharmaceutically acceptable salt, especially the hydrochloride, thereof.

Beta-blockers suitable for use in the present invention include beta-adrenergic blocking agents (beta-blockers), which compete with epinephrine for beta-adrenergic receptors and interfere with the action of epinephrine. Preferably, the beta-blockers are selective for the beta-adrenergic receptor as compared to the alpha-adrenergic receptors, and so do not have a significant alpha-blocking effect. Suitable beta-blockers include compounds selected from acebutolol, atenolol, betaxolol, bisoprolol, carteolol, carvedilol, esmolol, labetalol, metoprolol, nadolol, oxprenolol, penbutolol, pindolol, propranolol, sotalol and timolol. Where the beta-blocker is an acid or base or otherwise capable of forming pharmaceutically acceptable salts or prodrugs, these forms are considered to be encompassed herein, and it is understood that the compounds may be administered in free form or in the form of a pharmaceutically acceptable salt or a prodrug, such as a physiologically hydrolyzable and acceptable ester. For example, metoprolol is suitably administered as its tartrate salt, propranolol is suitably administered as the hydrochloride salt, and so forth.

Platelet aggregation inhibitors include PLAVIX® (clopidogrel bisulfate), PLETAL® (cilostazol) and aspirin.

Cholesterol absorption modulators include ZETIA® (ezetimibe) and KT6-971 (Kotobuki Pharmaceutical Co. Japan).

HMG-Co-A reductase inhibitors (also called beta-hydroxy-beta-methylglutaryl-co-enzyme-A reductase inhibitors or statins) are understood to be those active agents which may be used to lower lipid levels including cholesterol in blood.

The class of HMG-Co-A reductase inhibitors comprises compounds having differing structural features. For example, mention may be made of the compounds, which are selected from the group consisting of atorvastatin, cerivastatin, fluvastatin, lovastatin, pitavastatin, pravastatin, rosuvastatin and simvastatin, or in each case, a pharmaceutically acceptable salt thereof.

Preferred HMG-Co-A reductase inhibitors are those agents, which have been marketed, most preferred is atorvastatin, pitavastatin or simvastatin, or a pharmaceutically acceptable salt thereof.

HDL-increasing compounds include, but are not limited to, cholesterol ester transfer protein (CETP) inhibitors. Examples of CETP inhibitors include JTT705 disclosed in Example 26 of U.S. Pat. No. 6,426,365 issued Jul. 30, 2002, and pharmaceutically acceptable salts thereof.

Inhibition of interleukin 6 mediated inflammation may be achieved indirectly through regulation of endogenous cholesterol synthesis and isoprenoid depletion or by direct inhibition of the signal transduction pathway utilizing interleukin-6 inhibitor/antibody, interleukin-6 receptor inhibitor/antibody, interleukin-6 antisense oligonucleotide (ASON), gp130 protein inhibitor/antibody, tyrosine kinase inhibitors/antibodies, serine/threonine kinase inhibitors/antibodies, mitogen-activated protein (MAP) kinase inhibitors/antibodies, phosphatidylinositol 3-kinase (PI3K) inhibitors/antibodies, Nuclear factor kappaB (NF-KB) inhibitors/antibodies, IKB kinase (IKK) inhibitors/antibodies, activator protein-1 (AP-1) inhibitors/antibodies, STAT transcription factors inhibitors/antibodies, altered IL-6, partial peptides of IL-6 or IL-6 receptor, or SOCS (suppressors of cytokine signaling) protein, PPAR gamma and/or PPAR beta/delta activators/ligands or a functional fragment thereof.

A suitable antiinflammatory corticosteroid is dexamethasone.

Suitable antiproliferative agents are cladribine, rapamycin, vincristine and taxol.

A suitable inhibitor of extracellular matrix synthesis is halofuginone.

A suitable growth factor or cytokine signal transduction inhibitor is, e.g. the ras inhibitor R115777.

A suitable tyrosine kinase inhibitor is tyrphostin.

Suitable renin inhibitors are described, e.g. in WO 2006/116435. A preferred renin inhibitor is aliskiren, preferably in the form of the hemi-fumarate salt thereof.

MCP-1 antagonists may, e.g. be selected from anti-MCP-1 antibodies, preferably monoclonal or humanized monoclonal antibodies, MCP-1 expression inhibitors, CCR2-antagonists, TNF-alpha inhibitors, VCAM-1 gene expression inhibitors and anti-05a monoclonal antibodies.

MCP-1 antagonists and compositions containing such inhibitors are described, e.g. in WO02/070509, WO02/081463, WO02/060900, US2006/670364, US2006/677365, WO2006/097624, US2006/316449, WO2004/056727, WO03/053368, WO00/198289, WO00/157226, WO00/046195, WO00/046196, WO00/046199, WO00/046198, WO00/046197, WO99/046991, WO99/007351, WO98/006703, WO97/012615, WO2005/105133, WO03/037376, WO2006/125202, WO2006/085961, WO2004/024921, WO2006/074265.

Suitable MCP-1 antagonists are, for instance, C-243 (Telik Inc.); NOX-E36 (Noxxon Pharma AG); AP-761 (Actimis Pharmaceuticals Inc.); ABN-912, NIBR-177 (Novartis AG); CC-11006 (Celgene Corp.); SSR-150106 (Sanofi-Aventis); MLN-1202 (Millenium Pharmaceuticals Inc.); AG1-1067, AGIX-4207, AGM 096 (AtherioGenics Inc.); PRS-211095, PRS-211092 (Pharmos Corp.); anti-05a monoclonal antibodies, e.g. neutrazumab (G2 Therapies Ltd.); AZD-6942 (AstraZeneca plc.); 2-mercaptoimidazoles (Johnson & Johnson); TEI-E00526, TEI-6122 (Deltagen); RS-504393 (Roche Holding AG); SB-282241, SB-380732, ADR-7 (GlaxoSmithKline); anti-MCP-1 monoclonal antibodies(Johnson & Johnson).

Combinations of QC-inhibitors with MCP-1 antagonists may be useful for the treatment of inflammatory diseases in general, including neurodegenerative diseases.

Combinations of QC-inhibitors with MCP-1 antagonists are preferred for the treatment of Alzheimer's disease.

Most preferably the QC inhibitor is combined with one or more compounds selected from the following group:

PF-4360365, m266, bapineuzumab, R-1450, Posiphen, (+)-phenserine, MK-0752, LY-450139, E-2012, (R)-flurbiprofen, AZD-103, AAB-001 (Bapineuzumab), Tramiprosate, EGb-761, TAK-070, Doxofylline, theophylline, cilomilast, tofimilast, roflumilast, tetomilast, tipelukast, ibudilast, HT-0712, MEM-1414, oglemilast, Linezolid, budipine, isocarboxazid, phenelzine, tranylcypromine, indantadol, moclobemide, rasagiline, ladostigil, safinamide, ABT-239, ABT-834, GSK-189254A, Ciproxifan, JNJ-17216498, Fmoc-Ala-Pyrr-CN, Z-Phe-Pro-Benzothiazole, Z-321, ONO-1603, JTP-4819, S-17092, BIBP3226; (R)—N-2-(diphenylacetyl)-(R)—N-[1-(4-hydroxyphenyl)ethyl]arginine amide, Cevimeline, sabcomeline, (PD-151832), Donepezil, rivastigmine, (−)-phenserine, ladostigil, galantamine, tacrine, metrifonate, Memantine, topiramate, AVP-923, EN-3231, neramexane, valsartan, benazepril, enalapril, hydrochlorothiazide, amlodipine, diltiazem, isradipine, nicardipine, nifedipine, nimodipine, nisoldipine, nitrendipine, verapamil, amlodipine, acebutolol, atenolol, betaxolol, bisoprolol, carteolol, carvedilol, esmolol, labetalol, metoprolol, nadolol, oxprenolol, penbutolol, pindolol, propranolol, sotalol, timolol, PLAVIX® (clopidogrel bisulfate), PLETAL® (cilostazol), aspirin, ZETIA® (ezetimibe) and KT6-971, statins, atorvastatin, pitavastatin or simvastatin; dexamethasone, cladribine, rapamycin, vincristine, taxol, aliskiren, C-243, ABN-912, SSR-150106, MLN-1202 and betaferon.

In particular, the following combinations are considered:

a QC inhibitor, preferably a QC inhibitor of formula (I), more preferably a QC inhibitor selected from any one of examples 1-94, in combination with Atorvastatin for the treatment and/or prevention of artherosclerosis, a QC inhibitor, preferably a QC inhibitor of formula (I), more preferably a QC inhibitor selected from any one of examples 1-94, in combination with immunosuppressive agents, preferably rapamycin for the prevention and/or treatment of restenosis, a QC inhibitor, preferably a QC inhibitor of formula (I), more preferably a QC inhibitor selected from any one of examples 1-94, in combination with immunosuppressive agents, preferably paclitaxel for the prevention and/or treatment of restenosis, a QC inhibitor, preferably a QC inhibitor of formula (I), more preferably a QC inhibitor selected from any one of examples 1-94, in combination with AChE inhibitors, preferably Donepezil, for the prevention and/or treatment of Alzheimer's disease, a QC inhibitor, preferably a QC inhibitor of formula (I), more preferably a QC inhibitor selected from any one of examples 1-94, in combination with interferones, preferably Aronex, for the prevention and/or treatment of multiple sclerosis, a QC inhibitor, preferably a QC inhibitor of formula (I), more preferably a QC inhibitor selected from any one of examples 1-94, in combination with interferones, preferably betaferon, for the prevention and/or treatment of multiple sclerosis, a QC inhibitor, preferably a QC inhibitor of formula (I), more preferably a QC inhibitor selected from any one of examples 1-94, in combination with interferones, preferably Rebif, for the prevention and/or treatment of multiple sclerosis a QC inhibitor, preferably a QC inhibitor of formula (I), more preferably a QC inhibitor selected from any one of examples 1-94, in combination with Copaxone, for the prevention and/or treatment of multiple sclerosis, a QC inhibitor, preferably a QC inhibitor of formula (I), more preferably a QC inhibitor selected from any one of examples 1-94, in combination with dexamethasone, for the prevention and/or treatment of restenosis, a QC inhibitor, preferably a QC inhibitor of formula (I), more preferably a QC inhibitor selected from any one of examples 1-94, in combination with dexamethasone, for the prevention and/or treatment of atherosclerosis, a QC inhibitor, preferably a QC inhibitor of formula (I), more preferably a QC inhibitor selected from any one of examples 1-94, in combination with dexamethasone, for the prevention and/or treatment of rheumatid arthritis, a QC inhibitor, preferably a QC inhibitor of formula (I), more preferably a QC inhibitor selected from any one of examples 1-94, in combination with HMG-Co-A-reductase inhibitors, for the prevention and/or treatment of restenosis, wherein the HMG-Co-A-reductase inhibitor is selected from atorvastatin, cerivastatin, fluvastatin, lovastatin, pitavastatin, pravastatin, rosuvastatin and simvastatin, a QC inhibitor, preferably a QC inhibitor of formula (I), more preferably a QC inhibitor selected from any one of examples 1-94, in combination with HMG-Co-A reductase inhibitors, for the prevention and/or treatment of atherosclerosis wherein the HMG-Co-A-reductase inhibitor is selected from atorvastatin, cerivastatin, fluvastatin, lovastatin, pitavastatin, pravastatin, rosuvastatin and simvastatin, a QC inhibitor, preferably a QC inhibitor of formula (I), more preferably a QC inhibitor selected from any one of examples 1-94, in combination with HMG-Co-A reductase inhibitors, for the prevention and/or treatment of rheumatoid arthritis wherein the HMG-Co-A-reductase inhibitor is selected from atorvastatin, cerivastatin, fluvastatin, lovastatin, pitavastatin, pravastatin, rosuvastatin and simvastatin, a QC inhibitor, preferably a QC inhibitor of formula (I), more preferably a QC inhibitor selected from any one of examples 1-94, in combination with amyloid-beta antibodies for the prevention and/or treatment of mild cognitive impairment, wherein the amyloid-beta antibody is Act-24, a QC inhibitor, preferably a QC inhibitor of formula (I), more preferably a QC inhibitor selected from any one of examples 1-94, in combination with amyloid-beta antibodies for the prevention and/or treatment of Alzheimer's disease, wherein the amyloid-beta antibody is Act-24, a QC inhibitor, preferably a QC inhibitor of formula (I), more preferably a QC inhibitor selected from any one of examples 1-94, in combination with amyloid-beta antibodies for the prevention and/or treatment of neurodegeneration in Down Syndrome, wherein the amyloid-beta antibody is Act-24, a QC inhibitor, preferably a QC inhibitor of formula (I), more preferably a QC inhibitor selected from any one of examples 1-94, in combination with beta-secretase inhibitors for the prevention and/or treatment of mild cognitive impairment, wherein the beta-secretase inhibitor is selected from WY-25105, GW-840736X and CTS-21166, a QC inhibitor, preferably a QC inhibitor of formula (I), more preferably a QC inhibitor selected from any one of examples 1-94, in combination with beta-secretase inhibitors for the prevention and/or treatment of Alzheimer's disease, wherein the beta-secretase inhibitor is selected from WY-25105, GW-840736X and CTS-21166, a QC inhibitor, preferably a QC inhibitor of formula (I), more preferably a QC inhibitor selected from any one of examples 1-94, in combination with beta-secretase inhibitors for the prevention and/or treatment of neurodegeneration in Down Syndrome, wherein the beta-secretase inhibitor is selected from WY-25105, GW-840736X and CTS-21166, a QC inhibitor, preferably a QC inhibitor of formula (I), more preferably a QC inhibitor selected from any one of examples 1-94, in combination with gamma-secretase inhibitors for the prevention and/or treatment of mild cognitive impairment, wherein the gamma-secretase inhibitor is selected from LY-450139, LY-411575 and AN-37124, a QC inhibitor, preferably a QC inhibitor of formula (I), more preferably a QC inhibitor selected from any one of examples 1-94, in combination with gamma-secretase inhibitors for the prevention and/or treatment of Alzheimer's disease, wherein the gamma-secretase inhibitor is selected from LY-450139, LY-411575 and AN-37124, a QC inhibitor, preferably a QC inhibitor of formula (I), more preferably a QC inhibitor selected from any one of examples 1-94, in combination with gamma-secretase inhibitors for the prevention and/or treatment of neurodegeneration in Down Syndrome, wherein the gamma-secretase inhibitor is selected from LY-450139, LY-411575 and AN-37124.

Such a combination therapy is in particular useful for AD, FAD, FDD and neurodegeneration in Down syndrome as well as atherosclerosis, rheumatoid arthritis, restenosis and pancreatitis.

Such combination therapies might result in a better therapeutic effect (less proliferation as well as less inflammation, a stimulus for proliferation) than would occur with either agent alone.

With regard to the specific combination of inhibitors of QC and further compounds it is referred in particular to WO 2004/098625 in this regard, which is incorporated herein by reference.

Pharmaceutical Compositions

To prepare the pharmaceutical compositions of this invention, at least one compound of formula (I) optionally in combination with at least one of the other aforementioned agents can be used as the active ingredient(s). The active ingredient(s) is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

The pharmaceutical composition may contain between about 0.01 mg and 100 mg, preferably about 5 to 50 mg, of each compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamid-ephenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

In a further aspect, the invention also provides a process for preparing a pharmaceutical composition comprising at least one compound of formula (I), optionally in combination with at least one of the other aforementioned agents and a pharmaceutically acceptable carrier.

The compositions are preferably in a unit dosage form in an amount appropriate for the relevant daily dosage.

Suitable dosages, including especially unit dosages, of the compounds of the present invention include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

| Example | Structure | Name | [M + H]$^+$ | Process Route |
|---|---|---|---|---|
| 1 | 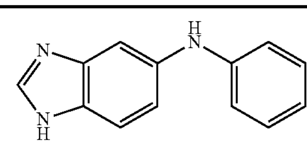 | N-Phenyl-1H-benzo[d]imidazol-5-amine | 210.2 | 1 |

-continued

| Example | Structure | Name | [M + H]⁺ | Process Route |
|---|---|---|---|---|
| 2 | 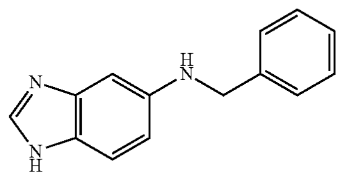 [SMILES: c1ccc(CNc2ccc3[nH]cnc3c2)cc1] | N-Benzyl-1H-benzo[d]imidazol-5-amine | 224.5 | 1, and alternative procedure as shown |
| 3 | 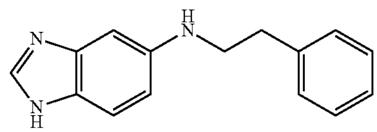 [SMILES: c1ccc(CCNc2ccc3[nH]cnc3c2)cc1] | N-Phenethyl-1H-benzo[d]imidazol-5-amine | 238.3 | 1 |
| 4 | 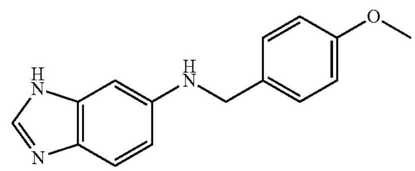 [SMILES: COc1ccc(CNc2ccc3nc[nH]c3c2)cc1] | N-(4-Methoxybenzyl)-3H-benzo[d]imidazol-5-amine | 254.3 | 1 and 2 |
| 5 | 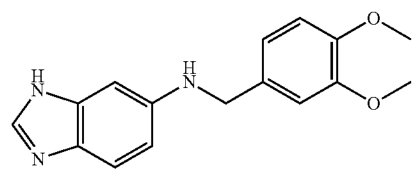 [SMILES: COc1ccc(CNc2ccc3nc[nH]c3c2)cc1OC] | N-(3,4-Dimethoxybenzyl)-3H-benzo[d]imidazol-5-amine | 284.3 | 1 |
| 6 | 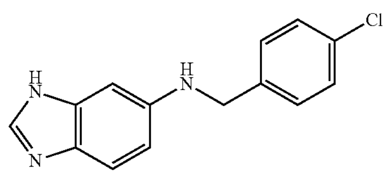 [SMILES: Clc1ccc(CNc2ccc3nc[nH]c3c2)cc1] | N-(4-Chlorobenzyl)-3H-benzo[d]imidazol-5-amine | 258.3 | 1 and 2 |
| 7 | 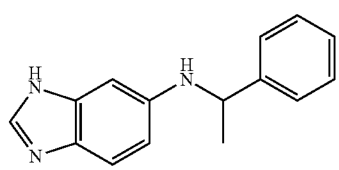 [SMILES: CC(Nc1ccc2nc[nH]c2c1)c1ccccc1] | N-(1-Phenyethyl)-3H-benzo[d]imidazol-5-amine | 238.1 | 1 |
| 8 | 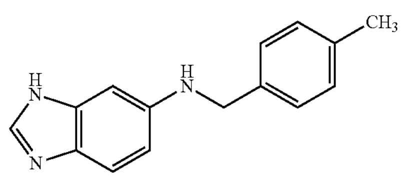 [SMILES: Cc1ccc(CNc2ccc3nc[nH]c3c2)cc1] | N-(4-Methylbenzyl)-3H-benzo[d]imidazol-5-amine | 238.3 | 1 |
| 9 | 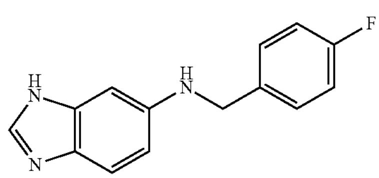 [SMILES: Fc1ccc(CNc2ccc3nc[nH]c3c2)cc1] | N-(4-Fluorobenzyl)-3H-benzo[d]imidazol-5-amine | 242.4 | 1 |

-continued

| Example | Structure | Name | [M + H]⁺ | Process Route |
|---|---|---|---|---|
| 10 | 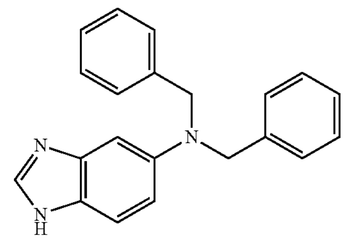 [SMILES: c1ccc(CN(Cc2ccccc2)c2ccc3[nH]cnc3c2)cc1] | N,N-Dibenzyl-1H-benzo[d]imidazol-5-amine | 242.4 | 1 |
| 11 | 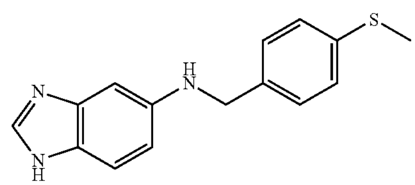 [SMILES: CSc1ccc(CNc2ccc3[nH]cnc3c2)cc1] | N-(4-(Methylthio)benzyl)-1H-benzo[d]imidazol-5-amine | 270.5 | 2 and 5 |
| 12 | 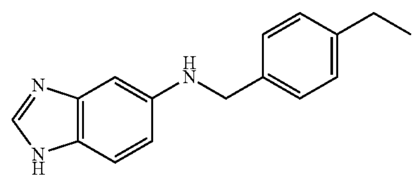 [SMILES: CCc1ccc(CNc2ccc3[nH]cnc3c2)cc1] | N-(4-Ethylbenzyl)-1H-benzo[d]imidazol-5-amine | 252.4 | 2 |
| 13 | 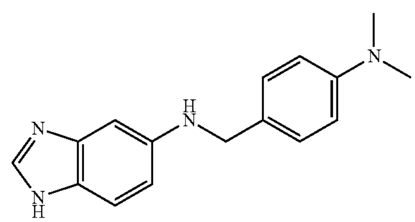 [SMILES: CN(C)c1ccc(CNc2ccc3[nH]cnc3c2)cc1] | N-(4-(Dimethylamino)benzyl)-1H-benzo[d]imidazol-5-amine | 166.3 | 2 |
| 14 | 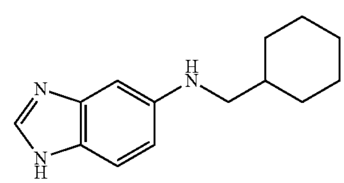 [SMILES: c1nc2cc(NCC3CCCCC3)ccc2[nH]1] | N-(Cyclohexylmethyl)-1H-benzo[d]imidazol-5-amine | 230.4 | 3 |
| 15 | 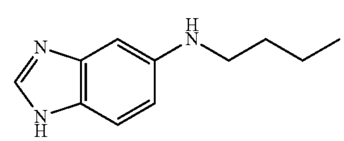 | N-Butyl-1H-benzo[d]imidazol-5-amine | 190.4 | 3 |
| 16 | 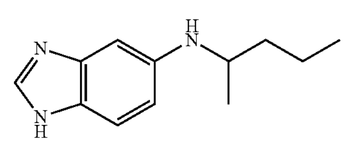 | N-(Pentan-2-yl)-1H-benzo[d]imidazol-5-amine | 204.4 | 3 |
| 17 | 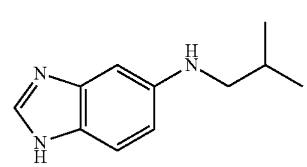 | N-Isobutyl-1H-benzo[d]imidazol-5-amine | 190.4 | 3 |

-continued

| Example | Structure | Name | [M + H]⁺ | Process Route |
|---------|-----------|------|----------|---------------|
| 18 | 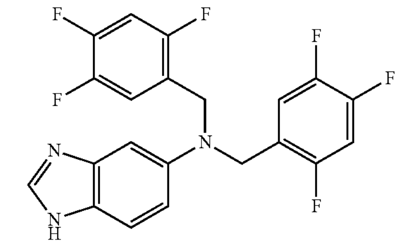 [SMILES: Fc1cc(F)c(CN(Cc2cc(F)c(F)cc2F)c2ccc3[nH]cnc3c2)cc1F] | N,N-Bis(2,4,5-trifluorobenzyl)-1H-benzo[d]imidazol-5-amine | 422.2 | 4 |
| 19 | 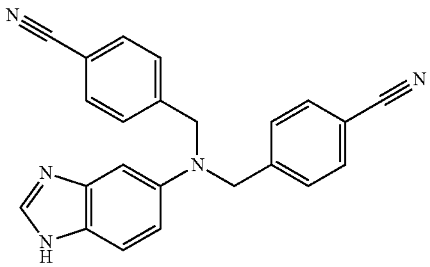 [SMILES: N#Cc1ccc(CN(Cc2ccc(C#N)cc2)c2ccc3[nH]cnc3c2)cc1] | N,N-Bis(4-cyanobenzyl)-1H-benzo[d]imidazol-5-amine | 364.2 | 4 |
| 20 | 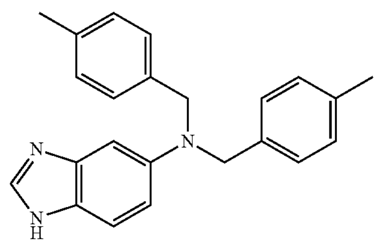 [SMILES: Cc1ccc(CN(Cc2ccc(C)cc2)c2ccc3[nH]cnc3c2)cc1] | N,N-Bis((4-methylbenzyl)-1H-benzo[d]imidazol-5-amine | 342.1 | 5 |
| 21 | 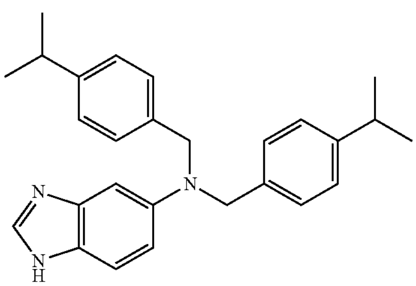 [SMILES: CC(C)c1ccc(CN(Cc2ccc(C(C)C)cc2)c2ccc3[nH]cnc3c2)cc1] | N,N-Bis(4-isopropylbenzyl)-1H-benzo[d]imidazol-5-amine | 398.4 | 5 |
| 22 | 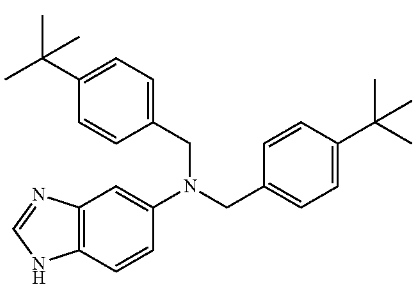 [SMILES: CC(C)(C)c1ccc(CN(Cc2ccc(C(C)(C)C)cc2)c2ccc3[nH]cnc3c2)cc1] | N,N-Bis(4-tert-butylbenzyl)-1H-benzo[d]imidazol-5-amine | 426.3 | 5 |
| 23 | 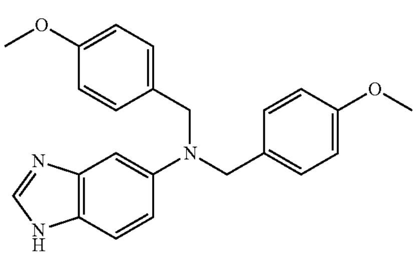 | N,N-Bis(4-methoxybenzyl)-1H-benzo[d]imidazol-5-amine | 374.1 | 5 |

-continued

| Example | Structure | Name | [M + H]⁺ | Process Route |
|---|---|---|---|---|
| 24 | 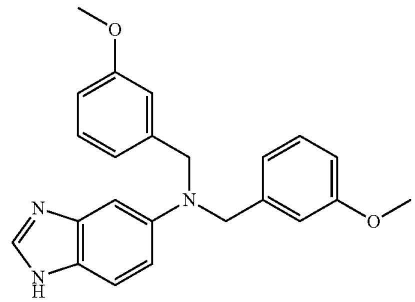 [SMILES: COc1cccc(CN(Cc2cccc(OC)c2)c2ccc3[nH]cnc3c2)c1] | N,N-Bis(3-methoxybenzyl)-1H-benzo[d]imidazol-5-amine | 374.1 | 5 |
| 25 | 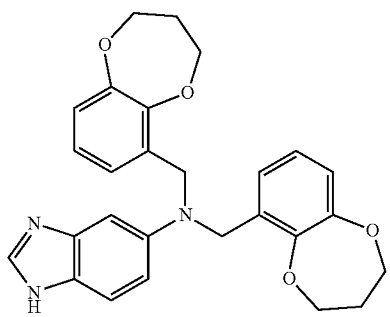 [SMILES: c1cc(CN(Cc2cccc3c2OCCCO3)c2ccc3[nH]cnc3c2)c2c(c1)OCCCO2] | N,N-Bis((3,4-dihydro-2H-benzo[b][1,4]dioxepin-9-yl)methyl)-1H-benzo[d]imidazol-5-amine | 458.5 | 5 |
| 26 | 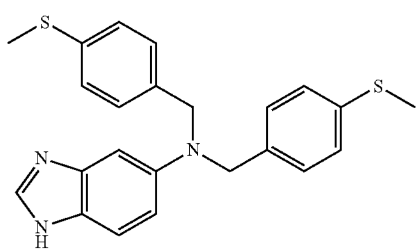 | N,N-Bis(4-(methylthio)benzyl)-1H-benzo[d]imidazol-5-amine | 406.4 | 5 |
| 27 | 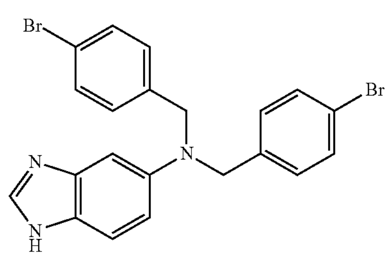 [SMILES: Brc1ccc(CN(Cc2ccc(Br)cc2)c2ccc3[nH]cnc3c2)cc1] | N,N-Bis(4-bromobenzyl)-1H-benzo[d]imidazol-5-amine | 472.3 | 5 |
| 28 | 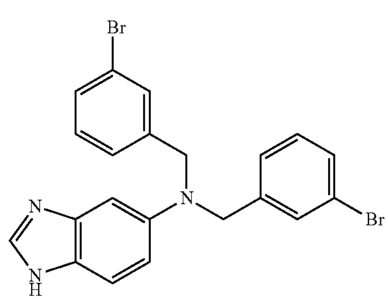 [SMILES: Brc1cccc(CN(Cc2cccc(Br)c2)c2ccc3[nH]cnc3c2)c1] | N,N-Bis(3-bromobenzyl)-1H-benzo[d]imidazol-5-amine | 472.2 | 5 |

-continued

| Example | Structure | Name | [M + H]+ | Process Route |
|---|---|---|---|---|
| 29 | 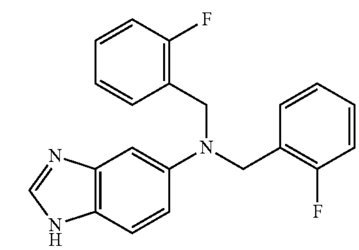 [SMILES: Fc1ccccc1CN(Cc1ccccc1F)c1ccc2[nH]cnc2c1] | N,N-Bis(2-fluorobenzyl)-1H-benzo[d]imidazol-5-amine | 350.2 | 5 |
| 30 | 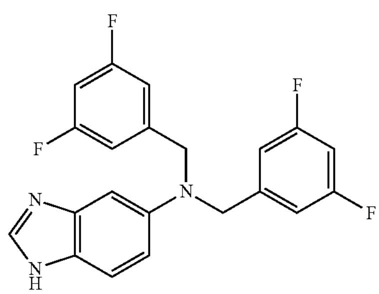 [SMILES: Fc1cc(F)cc(CN(Cc2cc(F)cc(F)c2)c2ccc3[nH]cnc3c2)c1] | N,N-Bis(3,5-difluorobenzyl)-1H-benzo[d]imidazol-5-amine | 386.2 | 5 |
| 31 | 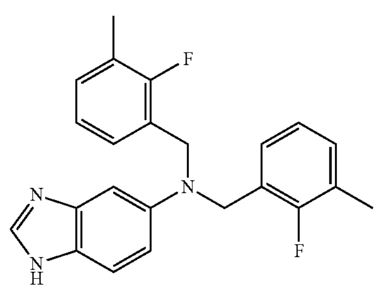 [SMILES: Cc1cccc(CN(Cc2cccc(C)c2F)c2ccc3[nH]cnc3c2)c1F] | N,N-Bis(2-fluoro-3-methylbenzyl)-1H-benzo[d]imidazol-5-amine | 378.1 | 5 |
| 32 | 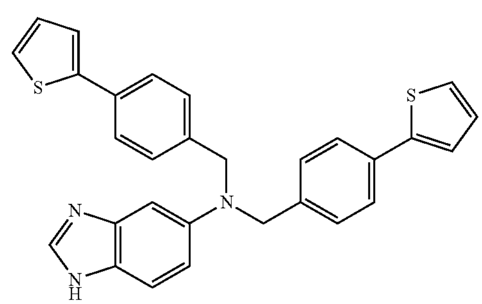 [SMILES: c1csc(-c2ccc(CN(Cc3ccc(-c4cccs4)cc3)c3ccc4[nH]cnc4c3)cc2)c1] | N,N-Bis(4-(thiophen-2-yl)benzyl)-1H-benzo[d]imidazol-5-amine | 478.4 | 5 |
| 33 | 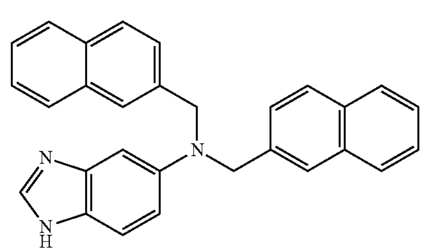 [SMILES: c1ccc2cc(CN(Cc3ccc4ccccc4c3)c3ccc4[nH]cnc4c3)ccc2c1] | N,N-Bis((naphthalen-2-yl)methyl))-1H-benzo[d]imidazol-5-amine | 414.5 | 5 |

-continued

| Example | Structure | Name | [M + H]⁺ | Process Route |
|---|---|---|---|---|
| 34 | 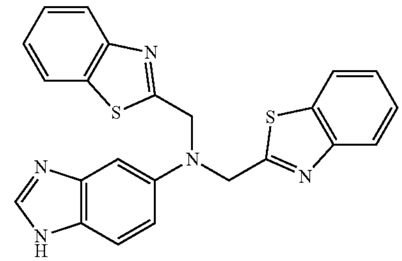 [SMILES: c1ccc2sc(CN(Cc3nc4ccccc4s3)c3ccc4[nH]cnc4c3)nc2c1] | N,N-Bis((benzo[d]thiazol-2-yl)methyl)-1H-benzo[d]imidazol-5-amine | 428.1 | 5 |
| 35 | 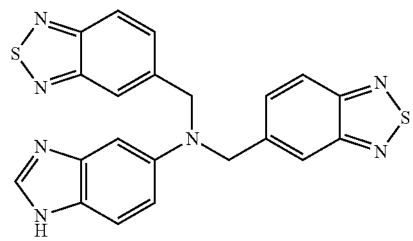 [SMILES: c1nc2cc(N(Cc3ccc4nsnc4c3)Cc3ccc4nsnc4c3)ccc2[nH]1] | N,N-Bis-((benzo[c][1,2,5]thiadiazol-5-yl)methyl)-1H-benzo[d]imidazol-5-amine | 430.4 | 5 |
| 36 | 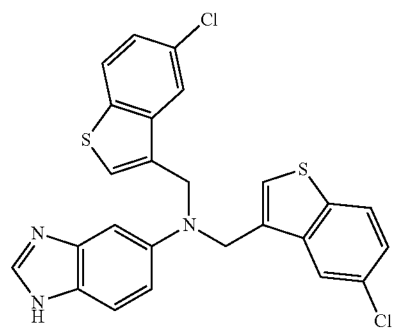 [SMILES: Clc1ccc2scc(CN(Cc3csc4ccc(Cl)cc34)c3ccc4[nH]cnc4c3)c2c1] | N,N-Bis((5-chlorobenzo[b]thiophen-3-yl)methyl)-1H-benzo[d]imidazol-5-amine | 494.4 | 5 |
| 37 | 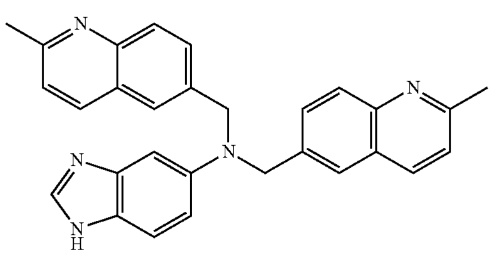 | N,N-Bis((2-methylquinolin-6-yl)methyl)-1H-benzo[d]imidazol-5-amine | 444.5 | 5 |
| 38 | 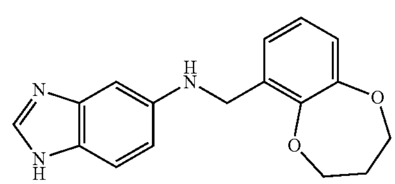 [SMILES: c1cc(CNc2ccc3[nH]cnc3c2)c2c(c1)OCCCO2] | N-((3,4-Dihydro-2H-benzo[b][1,4]dioxepin-9-yl)methyl)-1H-benzo[d]imidazol-5-amine | 296.5 | 5 mono-alkylated side product |
| 39 | 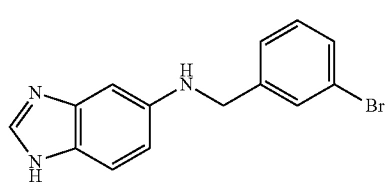 [SMILES: Brc1cccc(CNc2ccc3[nH]cnc3c2)c1] | N-(3-Bromobenzyl)-1H-benzo[d]imidazol-5-amine | 302.3 | 5 mono-alkylated side product |

-continued

| Example | Structure | Name | [M + H]⁺ | Process Route |
|---------|-----------|------|----------|---------------|
| 40 | 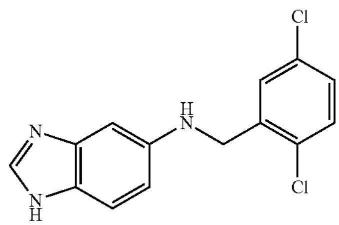 [SMILES: Clc1ccc(Cl)c(CNc2ccc3[nH]cnc3c2)c1] | N-(2,5-Dichlorobenzyl)-1H-benzo[d]imidazol-5-amine | 292.2 | 5 |
| 41 | 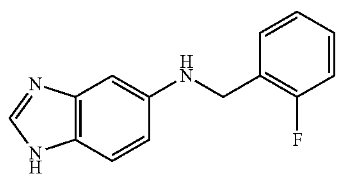 [SMILES: Fc1ccccc1CNc1ccc2[nH]cnc2c1] | N-(2-Fluorobenzyl)-1H-benzo[d]imidazol-5-amine | 242.3 | 5 mono-alkylated side product |
| 42 | 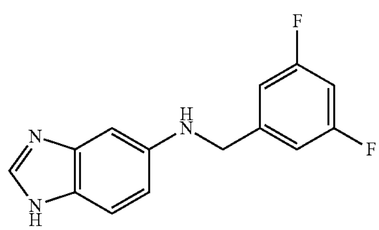 [SMILES: Fc1cc(F)cc(CNc2ccc3[nH]cnc3c2)c1] | N-(3,5-Difluorobenzyl)-1H-benzo[d]imidazol-5-amine | 260.3 | 5 mono-alkylated side product |
| 43 | 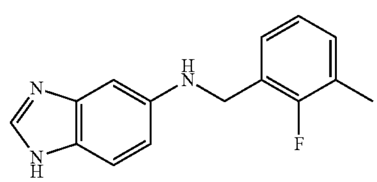 [SMILES: Cc1cccc(CNc2ccc3[nH]cnc3c2)c1F] | N-(2-Fluoro-3-methylbenzyl)-1H-benzo[d]imidazol-5-amine | 256.5 | 5 mono-alkylated side product |
| 44 | 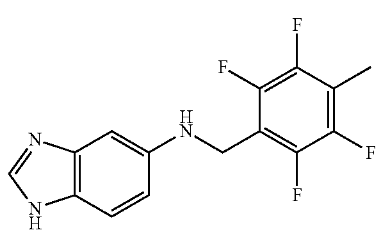 [SMILES: Cc1c(F)c(F)c(CNc2ccc3[nH]cnc3c2)c(F)c1F] | N-(2,3,5,6-Tetrafluoro-4-methylbenzyl)-1H-benzo[d]imidazol-5-amine | 310.2 | 5 |
| 45 | 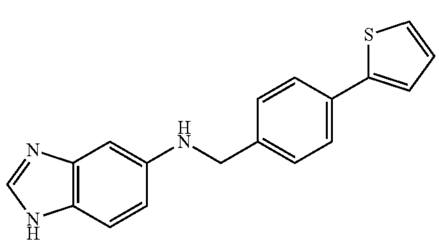 [SMILES: c1csc(-c2ccc(CNc3ccc4[nH]cnc4c3)cc2)c1] | N-(4-(Thiophen-2-yl)benzyl)-1H-benzo[d]imidazol-5-amine | 306.0 | 5 mono-alkylated side product |
| 46 | 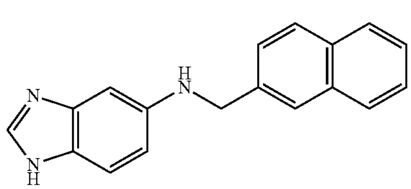 [SMILES: c1ccc2cc(CNc3ccc4[nH]cnc4c3)ccc2c1] | N-((Naphthalen-2-yl)methyl)-1H-benzo[d]imidazol-5-amine | 274.4 | 5 mono-alkylated side product |

-continued

| Example | Structure | Name | [M + H]+ | Process Route |
|---|---|---|---|---|
| 47 | 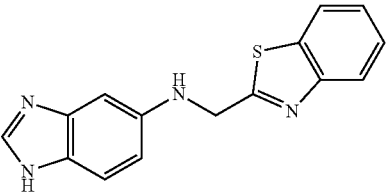 [SMILES: c1ccc2sc(CNc3ccc4[nH]cnc4c3)nc2c1] | N-((Benzo[d]thiazol-2-yl)methyl)-1H-benzo[d]imidazol-5-amine | 281.3 | 5 mono-alkylated side product |
| 48 | 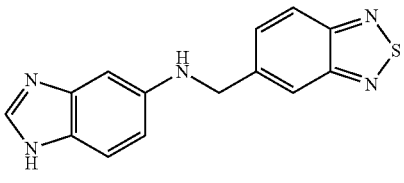 [SMILES: c1nc2cc(NCc3ccc4nsnc4c3)ccc2[nH]1] | N-((Benzo[c][1,2,5]thiadiazol-6-yl)methyl)-1H-benzo[d]imidazol-5-amine | 282.4 | 5 mono-alkylated side product |
| 49 | 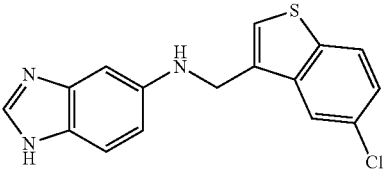 [SMILES: Clc1ccc2scc(CNc3ccc4[nH]cnc4c3)c2c1] | N-((5-Chlorobenzo[b]thiophen-3-yl)methyl)-1H-benzo[d]imidazol-5-amine | 314.3 | 5 mono-alkylated side product |
| 50 | 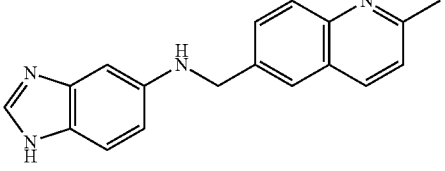 | N-((2-Methylquinolin-6-yl)methyl)-1H-benzo[d]imidazol-5-amine | 289.1 | 5 mono-alkylated side product |
| 51 | 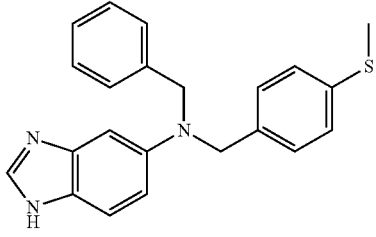 [SMILES: CSc1ccc(CN(Cc2ccccc2)c2ccc3[nH]cnc3c2)cc1] | N-(4-(Methylthio)benzyl)-N-benzyl-1H-benzo[d]imidazol-5-amine | 360.4 | 6 |
| 52 | 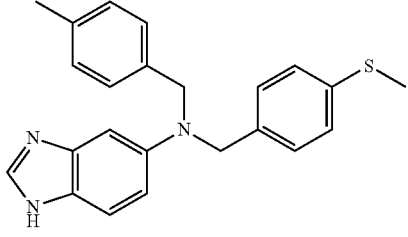 | N-(4-(Methylthio)benzyl)-N-(4-methylbenzyl)-1H-benzo[d]imidazol-5-amine | 374.1 | 6 |
| 53 | 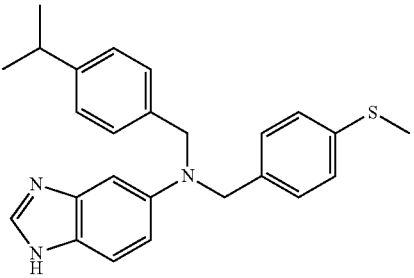 [SMILES: CSc1ccc(CN(Cc2ccc(C(C)C)cc2)c2ccc3[nH]cnc3c2)cc1] | N-(4-(Methylthio)benzyl)-N-(4-isopropylbenzyl)-1H-benzo[d]imidazol-5-amine | 402.4 | 6 |

-continued

| Example | Structure | Name | [M + H]+ | Process Route |
|---------|-----------|------|----------|---------------|
| 54 | 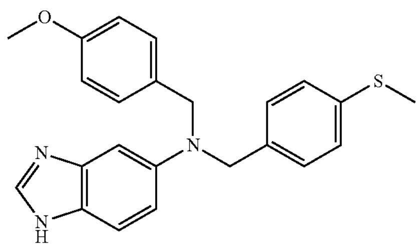 | N-(4-(Methylthio)benzyl)-N-(4-methoxybenzyl)-1H-benzo[d]imidazol-5-amine | 390.2 | 6 |
| 55 | 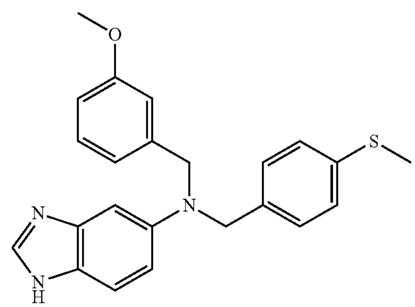 [SMILES: COc1cccc(CN(Cc2ccc(SC)cc2)c2ccc3[nH]cnc3c2)c1] | N-(3-Methoxybenzyl)-N-(4-(methylthio)benzyl)-1H-benzo[d]imidazol-5-amine | 390.1 | 6 |
| 56 | 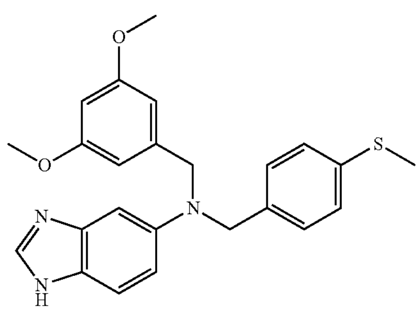 | N-(3,5-Dimethoxybenzyl)-N-(4-(methylthio)benzyl)-1H-benzo[d]imidazol-5-amine | 420.5 | 6 |
| 57 | 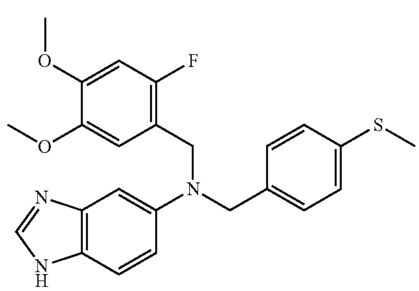 | N-(2-Fluoro-4,5-dimethoxybenzyl)-N-(4-(methylthio)benzyl)-1H-benzo[d]imidazol-5-amine | 438.5 | 6 |
| 58 | 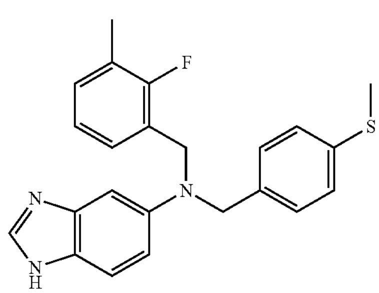 [SMILES: CSc1ccc(CN(Cc2cccc(C)c2F)c2ccc3[nH]cnc3c2)cc1] | N-(2-Fluoro-3-methylbenzyl)-N-(4-(methylthio)benzyl)-1H-benzo[d]imidazol-5-amine | 392.2 | 6 |

-continued

| Example | Structure | Name | [M + H]⁺ | Process Route |
|---|---|---|---|---|
| 59 | 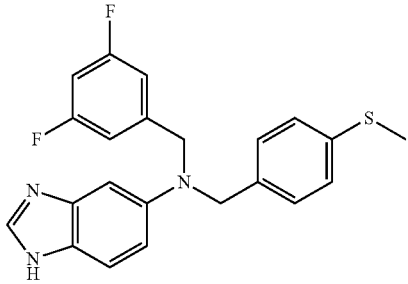 [SMILES: CSc1ccc(CN(Cc2cc(F)cc(F)c2)c2ccc3[nH]cnc3c2)cc1] | N-(3,5-Difluorobenzyl)-N-(4-(methylthio)benzyl)-1H-benzo[d]imidazol-5-amine | 396.2 | 6 |
| 60 | 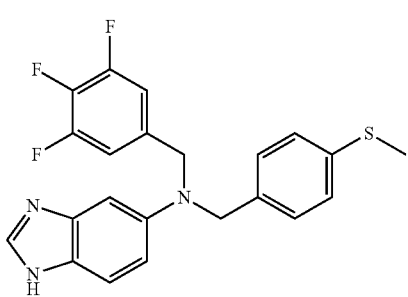 [SMILES: CSc1ccc(CN(Cc2cc(F)c(F)c(F)c2)c2ccc3[nH]cnc3c2)cc1] | N-(3,4,5-Trifluorobenzyl)-N-(4-(methylthio)benzyl)-1H-benzo[d]imidazol-5-amine | 414.3 | 6 |
| 61 | 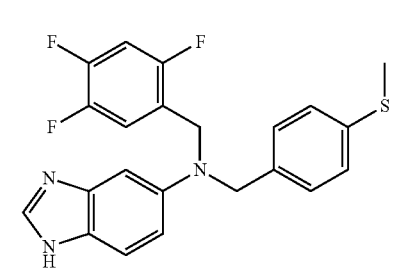 [SMILES: CSc1ccc(CN(Cc2cc(F)c(F)cc2F)c2ccc3[nH]cnc3c2)cc1] | N-(2,4,5-Trifluorobenzyl)-N-(4-(methylthio)benzyl)-1H-benzo[d]imidazol-5-amine | 414.2 | 6 |
| 62 | 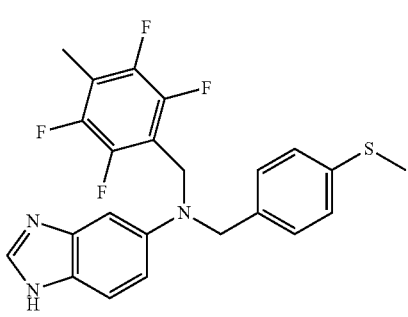 [SMILES: CSc1ccc(CN(Cc2c(F)c(F)c(C)c(F)c2F)c2ccc3[nH]cnc3c2)cc1] | N-(2,3,5,6-Tetrafluoro-4-methylbenzyl)-N-(4-(methylthio)benzyl)-1H-benzo[d]imidazol-5-amine | 446.4 | 6 |
| 63 | 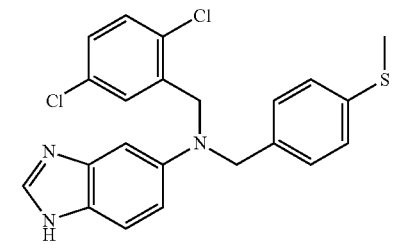 [SMILES: CSc1ccc(CN(Cc2cc(Cl)ccc2Cl)c2ccc3[nH]cnc3c2)cc1] | N-(2,5-Dichlorobenzyl)-N-(4-(methylthio)benzyl)-1H-benzo[d]imidazol-5-amine | 428.1 | 6 |

-continued

| Example | Structure | Name | [M + H]+ | Process Route |
|---|---|---|---|---|
| 64 | 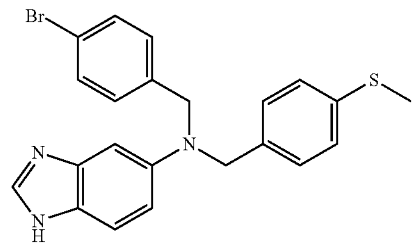 [SMILES: CSc1ccc(CN(Cc2ccc(Br)cc2)c2ccc3[nH]cnc3c2)cc1] | N-(4-(Methylthio)benzyl)-N-(4-bromobenzyl)-1H-benzo[d]imidazol-5-amine | 440.3 | 6 |
| 65 | 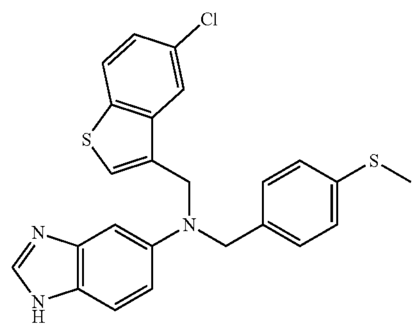 [SMILES: CSc1ccc(CN(Cc2csc3ccc(Cl)cc23)c2ccc3[nH]cnc3c2)cc1] | N-(4-(Methylthio)benzyl)-N-((5-chlorobenzo[b]thiophen-3-yl)methyl)-1H-benzo[d]imidazol-5-amine | 450.3 | 6 |
| 66 | 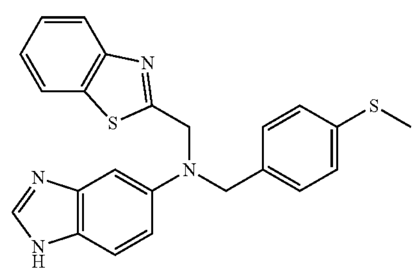 | N-(4-(Methylthio)benzyl)-N-((benzo[d]thiazol-2-yl)methyl)-1H-benzo[d]imidazol-5-amine | 417.2 | 6 |
| 67 | 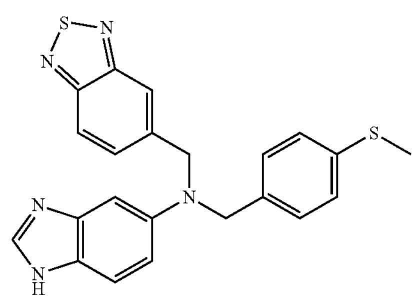 [SMILES: CSc1ccc(CN(Cc2ccc3nsnc3c2)c2ccc3[nH]cnc3c2)cc1] | N-(4-(Methylthio)benzyl)-N-((benzo[c][1,2,5]thiadiazol-6-yl)methyl)-1H-benzo[d]imidazol-5-amine | 418.5 | 6 |
| 68 | 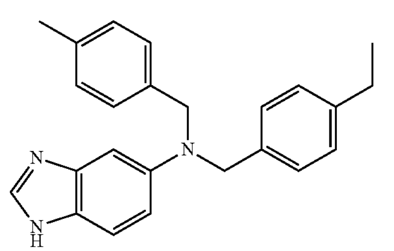 [SMILES: CCc1ccc(CN(Cc2ccc(C)cc2)c2ccc3[nH]cnc3c2)cc1] | N-(4-(Ethylbenzyl)-N-(4-methylbenzyl)-1H-benzo[d]imidazol-5-amine | 356.5 | 6 |

-continued

| Example | Structure | Name | [M + H]⁺ | Process Route |
|---|---|---|---|---|
| 69 | 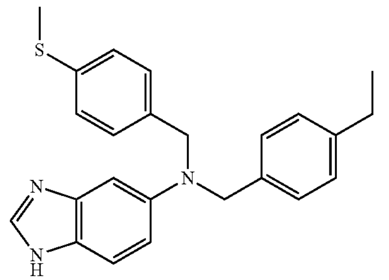 [SMILES: CCc1ccc(CN(Cc2ccc(SC)cc2)c2ccc3[nH]cnc3c2)cc1] | N-(4-(Methylthio)benzyl)-N-(4-ethylbenzyl)-1H-benzo[d]imidazol-5-amine | 388.4 | 6 |
| 70 | 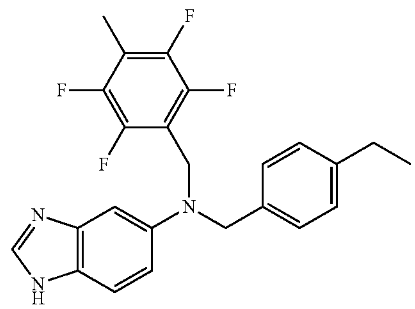 [SMILES: CCc1ccc(CN(Cc2c(F)c(F)c(C)c(F)c2F)c2ccc3[nH]cnc3c2)cc1] | N-(2,3,5,6-Tetrafluoro-4-methylbenzyl)-N-(4-ethylbenzyl)-1H-benzo[d]imidazol-5-amine | 428.4 | 6 |
| 71 | 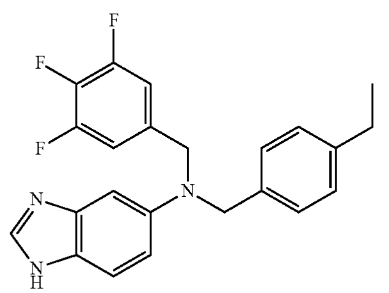 [SMILES: CCc1ccc(CN(Cc2cc(F)c(F)c(F)c2)c2ccc3[nH]cnc3c2)cc1] | N-(3,4,5-Trifluorobenzyl)-N-(4-ethylbenzyl)-1H-benzo[d]imidazol-5-amine | 396.2 | 6 |
| 72 | 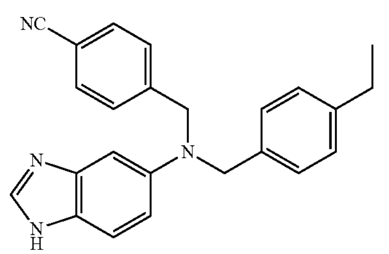 [SMILES: CCc1ccc(CN(Cc2ccc(C#N)cc2)c2ccc3[nH]cnc3c2)cc1] | N-(4-Cyanobenzyl)-N-(4-ethylbenzyl)-1H-benzo[d]imidazol-5-amine | 367.2 | 6 |
| 73 | 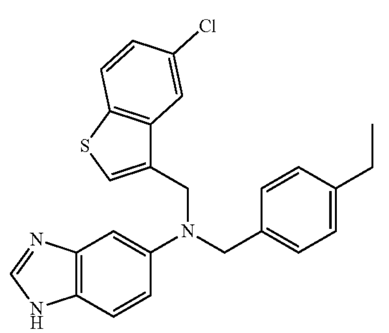 [SMILES: CCc1ccc(CN(Cc2csc3ccc(Cl)cc23)c2ccc3[nH]cnc3c2)cc1] | N-(4-Ethylbenzyl)-N-((5-chlorobenzo[b]thiophen-3-yl)methyl)-1H-benzo[d]imidazol-5-amine | 432.6 | 6 |

| Example | Structure | Name | [M + H]+ | Process Route |
|---|---|---|---|---|
| 74 | 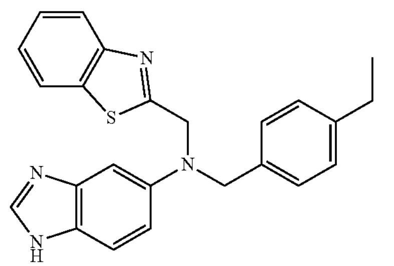 [SMILES: CCc1ccc(CN(Cc2nc3ccccc3s2)c2ccc3[nH]cnc3c2)cc1] | N-(4-Ethylbenzyl)-N-((benzo[d]thiazol-2-yl)methyl)-1H-benzo[d]imidazol-5-amine | 399.4 | 6 |
| 75 | 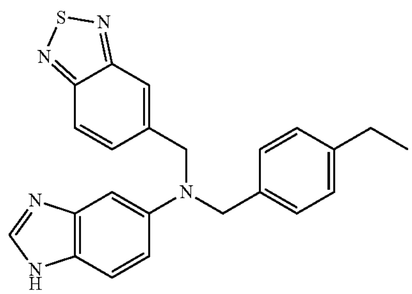 [SMILES: CCc1ccc(CN(Cc2ccc3nsnc3c2)c2ccc3[nH]cnc3c2)cc1] | N-(4-Ethylbenzyl)-N-((benzo[c][1,2,5]thiadiazol-6-yl)methyl)-1H-benzo[d]imidazol-5-amine | 400.2 | 6 |
| 76 | 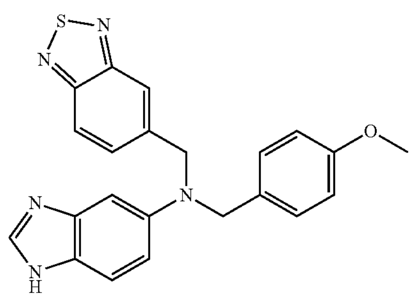 [SMILES: COc1ccc(CN(Cc2ccc3nsnc3c2)c2ccc3[nH]cnc3c2)cc1] | N-(4-Methoxybenzyl)-N-((benzo[c][1,2,5]thiadiazol-6-yl)methyl)-1H-benzo[d]imidazol-5-amine | 402.3 | 6 |
| 77 | 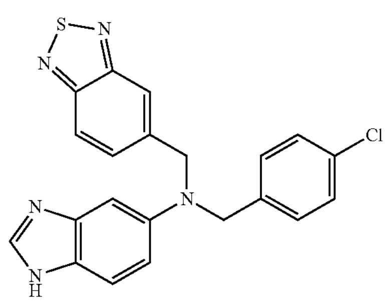 [SMILES: Clc1ccc(CN(Cc2ccc3nsnc3c2)c2ccc3[nH]cnc3c2)cc1] | N-(4-Chlorobenzyl)-N-((benzo[c][1,2,5]thiadiazol-6-yl)methyl)-1H-benzo[d]imidazol-5-amine | 406.4 | 6 |
| 78 | 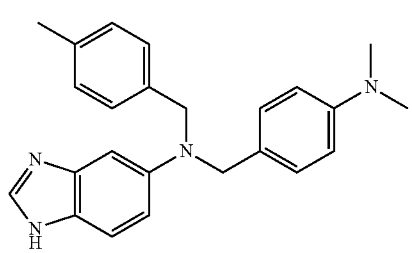 [SMILES: Cc1ccc(CN(Cc2ccc(N(C)C)cc2)c2ccc3[nH]cnc3c2)cc1] | N-(4-(Dimethylamino)benzyl)-N-(4-methylbenzyl)-1H-benzo[d]imidazol-5-amine | 371.4 | 6 |

-continued

| Example | Structure | Name | [M + H]⁺ | Process Route |
|---|---|---|---|---|
| 79 | 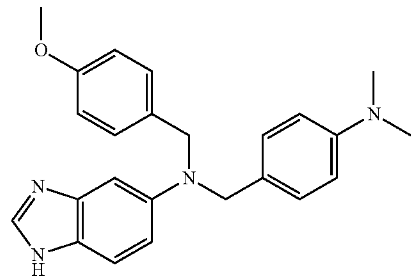 [SMILES: COc1ccc(CN(Cc2ccc(N(C)C)cc2)c2ccc3[nH]cnc3c2)cc1] | N-(4-(Dimethylamino)benzyl)-N-(4-methoxybenzyl)-1H-benzo[d]imidazol-5-amine | n.d. | 6 |
| 80 | 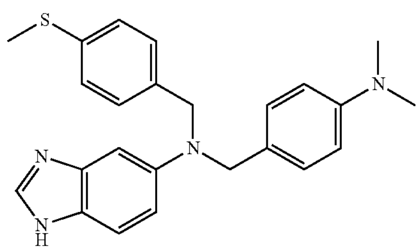 | N-(4-(Dimethylamino)benzyl)-N-(4-(methylthio)benzyl)-1H-benzo[d]imidazol-5-amine | n.d. | 6 |
| 81 | 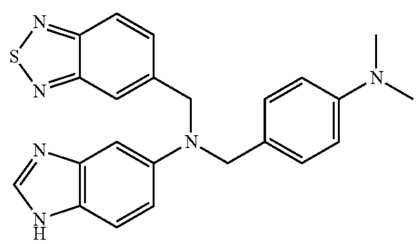 [SMILES: CN(C)c1ccc(CN(Cc2ccc3nsnc3c2)c2ccc3[nH]cnc3c2)cc1] | N-(4-(Dimethylamino)benzyl)-N-((benzo[c][1,2,5]thiadiazol-5-yl)methyl)-1H-benzo[d]imidazol-5-amine | n.d. | 6 |
| 82 | 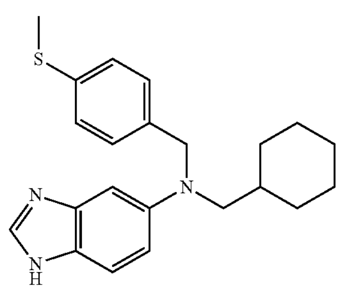 [SMILES: CSc1ccc(CN(CC2CCCCC2)c2ccc3[nH]cnc3c2)cc1] | N-(4-(Methylthio)benzyl)-N-(cyclohexylmethyl)-1H-benzo[d]imidazol-5-amine | 366.4 | 6 |
| 83 | 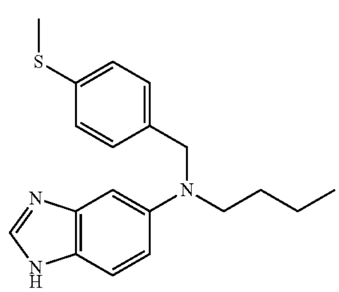 [SMILES: CCCCN(Cc1ccc(SC)cc1)c1ccc2[nH]cnc2c1] | N-(4-(Methylthio)benzyl)-N-butyl-1H-benzo[d]imidazol-5-amine | 326.4 | 6 |

-continued

| Example | Structure | Name | [M + H]+ | Process Route |
|---|---|---|---|---|
| 84 | 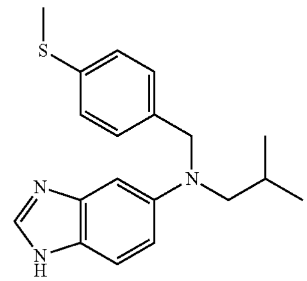 [SMILES: CSc1ccc(CN(CC(C)C)c2ccc3[nH]cnc3c2)cc1] | N-(4-(Methylthio)benzyl)-N-isobutyl-1H-benzo[d]imidazol-5-amine | 326.4 | 6 |
| 85 | 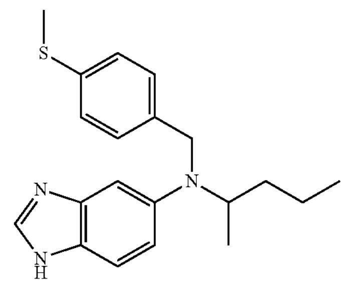 [SMILES: CCCC(C)N(Cc1ccc(SC)cc1)c1ccc2[nH]cnc2c1] | N-(4-(Methylthio)benzyl)-N-(pentan-2-yl)-1H-benzo[d]imidazol-5-amine | 340.3 | 6 |
| 86 | 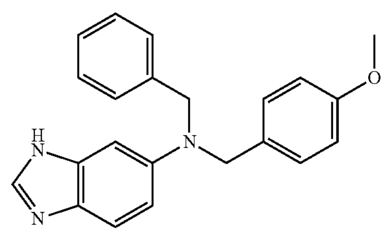 [SMILES: COc1ccc(CN(Cc2ccccc2)c2ccc3nc[nH]c3c2)cc1] | N-(4-Methoxybenzyl)-N-benzyl-3H-benzo[d]imidazol-5-amine | 344.1 | 6 |
| 87 | 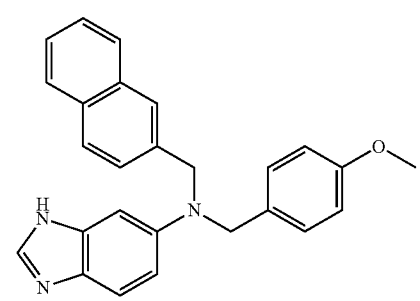 [SMILES: COc1ccc(CN(Cc2ccc3ccccc3c2)c2ccc3nc[nH]c3c2)cc1] | N-(4-Methoxybenzyl)-N-((naphthalen-2-yl)methyl)-3H-benzo[d]imidazol-5-amine | 394.2 | 6 |
| 88 | 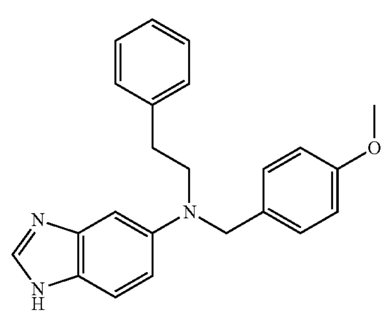 [SMILES: COc1ccc(CN(CCc2ccccc2)c2ccc3[nH]cnc3c2)cc1] | N-(4-Methoxybenzyl)-N-phenethyl-1H-benzo[d]imidazol-5-amine | 358.1 | 6 |

-continued

| Example | Structure | Name | [M + H]⁺ | Process Route |
|---|---|---|---|---|
| 89 | 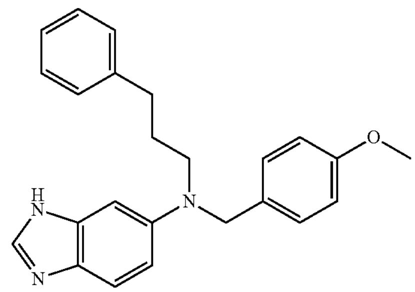 [SMILES: COc1ccc(CN(CCCc2ccccc2)c2ccc3nc[nH]c3c2)cc1] | N-(4-Methoxybenzyl)-N-(3-phenylpropyl)-3H-benzo[d]imidazol-5-amine | 372.1 | 6 |
| 90 | 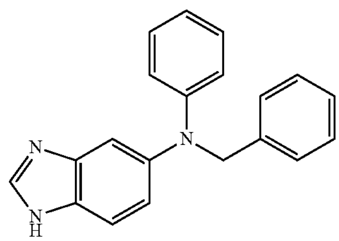 [SMILES: c1ccc(CN(c2ccccc2)c2ccc3[nH]cnc3c2)cc1] | N-Benzyl-N-phenyl-1H-benzo[d]imidazol-5-amine | 300.1 | See detailed description for Example 91 |
| 91 | 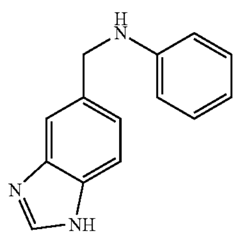 [SMILES: c1ccc(NCc2ccc3[nH]cnc3c2)cc1] | N-((1H-Benzo[d]imidazol-5-yl)methyl)benzenamine | 224.3 | 7 |
| 92 | 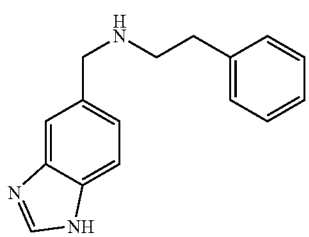 [SMILES: c1ccc(CCNCc2ccc3[nH]cnc3c2)cc1] | N-((1H-Benzo[d]imidazol-5-yl)methyl)-2-phenylethanamine | 252.2 | 7 |
| 93 | 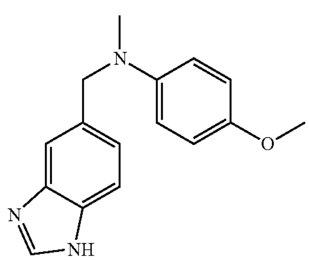 [SMILES: COc1ccc(N(C)Cc2ccc3[nH]cnc3c2)cc1] | N-((1H-Benzo[d]imidazol-5-yl)methyl)(4-methoxyphenyl)-N-methylmethanamine | 268.3 | 7 |
| 94 | 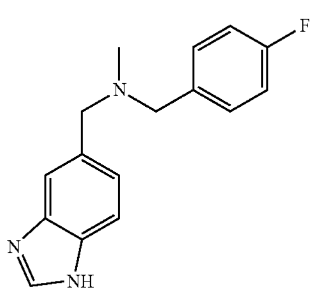 [SMILES: CN(Cc1ccc(F)cc1)Cc1ccc2[nH]cnc2c1] | N-((1H-Benzo[d]imidazol-5-yl)methyl)(4-fluorophenyl)-N-methylmethanamine | 270.1 | 7 |

General Synthesis Description:
Method 1

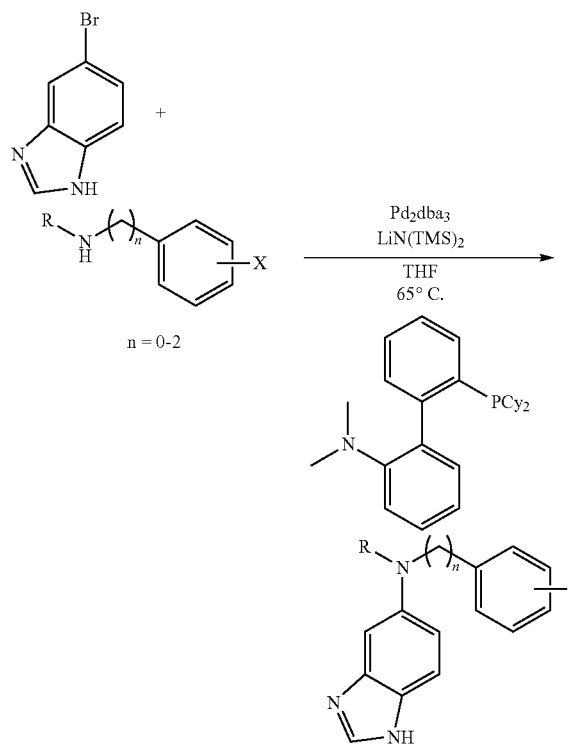

n = 0-2

5-Bromobenzimidazole (1 eq.) was dissolved in THF (3 ml). The respective amine (1.2 eq.), 2-dicyclohexylphosphino-2'-(N,N-dimethylamino)biphenyl (0.024 eq.; 2.4 mol %), $Pd_2 dba_3$ (0.01 eq.; 1 mol %) and lithiumbis(trimethylsilyl)amide 1 M in THF (2.2 eq.) were added and the mixture was heated under argon atmosphere to 65° C. for 24 h. After cooling to room temperature the mixture was acidified by means of 5 N HCl aq. and stirring was continued for an additional 10 min. The mixture was poured into a sat. solution of $NaHCO_3$ and extracted by means of ethyl acetate (3×20 ml). The combined organic layers were dried over $Na_2SO_4$, evaporated and the residue was purified by flash chromatography using basic $Al_2O_3$ and a $CHCl_3$/MeOH-gradient.

Method 2

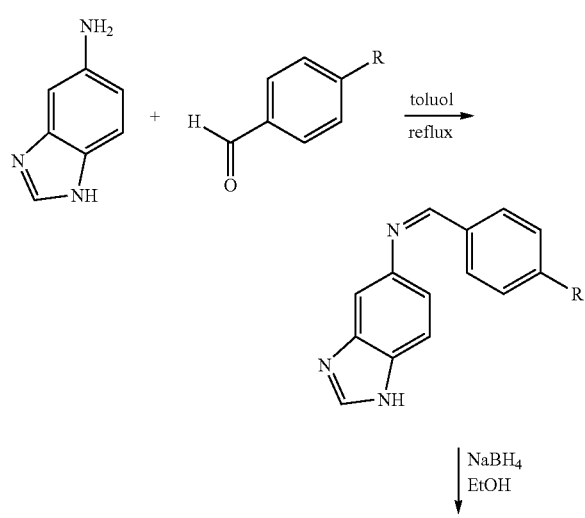

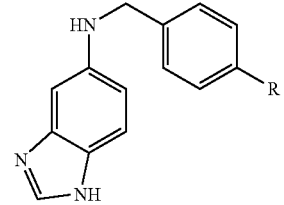

Benzimidazol-5-amine (1 eq.) was suspended in dry toluol (50 ml). After addition of the respective aldehyde (1.1 eq.), the mixture was heated to reflux for 3 h. The solvent was removed in vacuo and the remains were dissolved in dry EtOH (100 ml). This solution was added dropwise to a solution of $NaBH_4$ (1.5 eq.) in EtOH (50 ml) at room temperature. After stirring for 1 h the mixture was heated to reflux for an additional 4 h. After the addition of 5 N NaOH (5 eq.) the reaction was stirred at 60° C. overnight. The solvent was concentrated by half, diluted with water and extracted by means of ethyl acetate (3×100 ml). The combined organic layers were dried over $Na_2SO_4$, evaporated and the residue was purified by flash chromatography on silica using a $CHCl_3$/MeOH gradient.

Method 3

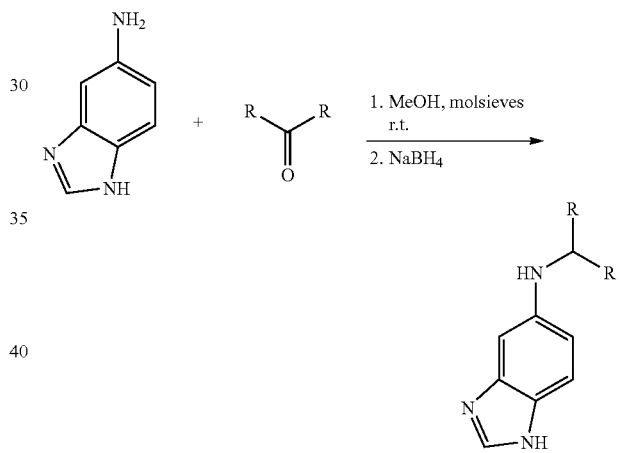

Benzimidazol-5-amine (1 eq.) was dissolved in MeOH (10 ml) and treated with the respective aldehyde or ketone (1.1 eq.). After the addition of molsieves 3 Å the mixture was stirred at room temperature for 24 h. $NaBH_4$ (2 eq.) was added and the mixture was stirred for 1 h and heated to reflux for additional 4 h. After the addition of 5 N NaOH (5 eq.) the mixture was stirred at 60° C. overnight. The mixture was diluted with water and extracted by means of ethyl acetate (3×25 ml). The combined organic layers were dried over $Na_2SO_4$, evaporated and the residue was purified by flash chromatography on silica using a $CHCl_3$/MeOH gradient.

Method 4

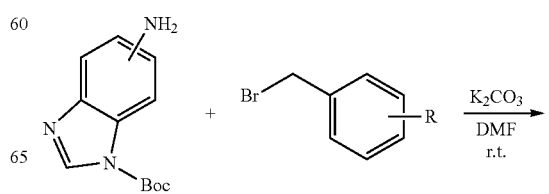

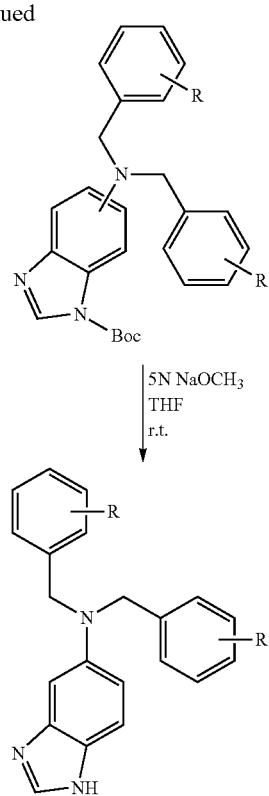

N1-Boc-benzimidazol-5-amine (1 eq.) was dissolved in DMF (5 ml) and treated with $K_2CO_3$ (2.5 eq.) and the respective benzylhalide (2.5 eq.). After stirring at room temperature for 24 h the mixture was diluted with water and extracted by means of ethyl acetate (3×25 ml). The combined organic layers were dried over $Na_2SO_4$ and the solvent was removed in vacuo. The residue was redissolved in THF (5 ml), treated with 5 N $NaOCH_3$ (3 eq.) and stirred at room temperature for 1 h. The mixture was diluted with water and extracted by means of ethyl acetate (3×25 ml). The combined organic layers were dried over $Na_2SO_4$, evaporated and the residue was purified by flash chromatography on silica using a $CHCl_3$/MeOH gradient.

Method 5

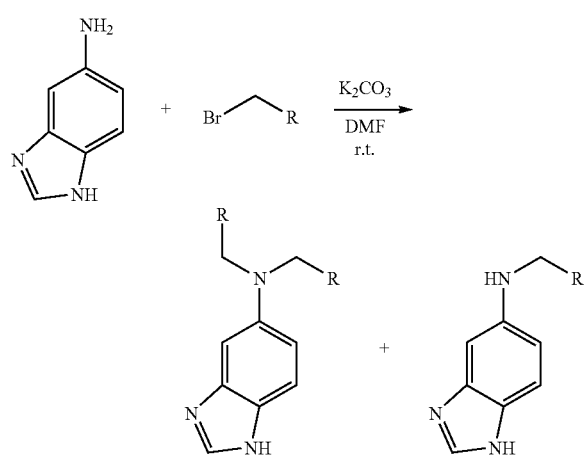

A solution of benzimidazol-5-amine (1 eq.) in DMF (5 ml) was treated with $K_2CO_3$ (2.2 eq.) and the respective alkylhalide (2.2 eq.) and stirred at room temperature for 24 h. The mixture was diluted with water and extracted by means of ethyl acetate (3×25 ml). The combined organic layers were dried over $Na_2SO_4$, evaporated and the residue was purified by flash chromatography on silica using a $CHCl_3$/MeOH gradient.

Method 6

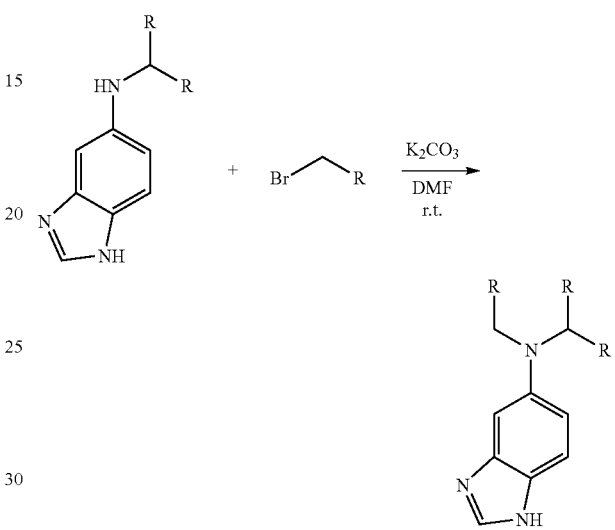

The corresponding N-monosubstituted benzimidazol-5-amine derivative (1 eq.) was dissolved in DMF (5 ml), treated with $K_2CO_3$ (1.1 eq.) and the respective alkylhalide (1.1 eq.) and stirred at room temperature for 24 h. The mixture was diluted with water and extracted by means of ethyl acetate (3×25 ml). The combined organic layers were dried over $Na_2SO_4$, evaporated and the residue was purified by flash chromatography on silica using a $CHCl_3$/MeOH gradient.

Method 7

1H-Benzo[d]imidazol-5-yl-methylamines

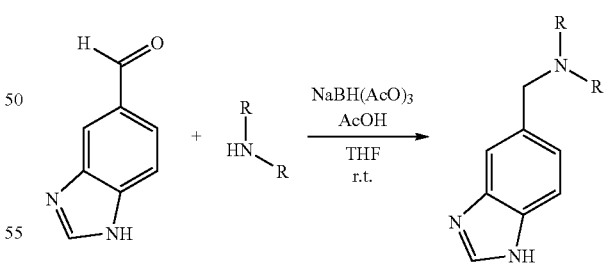

Benzimidazol-5-carbaldehyde (1 eq.) was dissolved in THF (10 ml). The respective amine (1 eq.), $NaBH(AcO)_3$ (1.5 eq.) and AcOH (1.5 eq.) were added and the mixture was stirred at room temperature overnight. The mixture was basified by means of 1 M aqueous NaOH and extracted with ethyl acetate (3×25 ml). The combined organic layers were dried over $Na_2SO_4$ and evaporated. The residue was purified by flash chromatography on silica using a $CHCl_3$/MeOH gradient.

SYNTHESIS OF THE EXAMPLES

Example 1

N-Phenyl-1H-benzo[d]imidazol-5-amine

The compound was synthesized starting from 5-bromobenzimidazole (1.0 g; 5 mmol; 1 eq.), aniline (559 mg; 0.547 ml; 6 mmol; 1.2 eq.), lithiumbis(trimethylsilyl)amide 1M in THF (11 ml; 11 mmol; 2.2 eq.), 2-dicyclohexylphosphino-2''-(N,N-dimethylamino)biphenyl) (45 mg; 0.12 mmol; 0.024 eq.; 2.4 mol %), $Pd_2$ $dba_3$ (45 mg; 0.05 mmol; 0.01 eq.; 1 mol %) and THF (5 ml) according to method 1; Yield: 0.565 g (54.1%); MS m/z: 210.2 $[M+H]^+$; $^1$H-NMR (500 MHz, DMSO d6): δ 6.72-6.75 (m, 1H); 6.94-6.96 (m, 1H); 7.00-7.02 (m, 2H); 7.16-7.19 (m, 2H); 7.25 (br s, 1H); 7.47 (d, 1H, $^3$J=8.5 Hz); 7.98 (br s, 1H); 8.04 (s, 1H); 12.13 (br s, 1H); HPLC (METHOD [A]): rt 10.62 min (87.0%)

Example 2

N-Benzyl-1H-benzo[d]imidazol-5-amine

The compound was synthesized starting from 5-bromobenzimidazole (200 mg; 1 mmol; 1 eq.), benzylamine (128 mg; 0.127 ml; 1.2 mmol; 1.2 eq.), 2-dicyclohexylphosphino-2'-(N,N-dimethylamino)biphenyl (9 mg; 0.024 mmol; 0.024 eq.; 2.4 mol %), $Pd_2$ $dba_3$ (9 mg; 0.01 mmol; 0.01 eq.; 1 mol %) and lithiumbis(trimethylsilyl)amide 1 M in THF (2.2 ml; 2.2 mmol; 2.2 eq.) according to method 1; Yield: 0.150 g (67.3%); MS m/z: 224.5 $[M+H]^+$; $^1$H-NMR (500 MHz, DMSO d6): δ 4.33 (s, 2H); 6.64 (d, 1H, $^4$J=2.1 Hz); 6.98 (dd, 1H; $^4$J=2.1 Hz, $^3$J=8.9 Hz); 7.23-7.38 (m, 5H); 7.51 (d, 1H, $^3$J=8.9 Hz); 8.07 (s, 1H); HPLC (METHOD [A]): rt 22.19 min (80.6%)

Example 2

(Alternative Procedure):
N-Benzyl-1H-benzo[d]imidazol-5-amine

Benzimidazol-5-carbaldehyde (146 mg; 1 mmol; 1 eq.) was dissolved in MeOH (10 ml). Benzylamine (0.109 ml; 1 mmol; 1 eq.) was added and the mixture was stirred overnight. $NaBH_4$ (57 mg; 1.5 mmol; 1.5 eq.) was added and stirring was continued overnight. The reaction was quenched by addition of water and extracted with ethyl acetate (3×25 ml). The combined organic layers were dried over $Na_2SO_4$ and evaporated. The residue was purified by flashchromatography on silica using a $CHCl_3$/MeOH gradient. Yield: 0.045 g (19%); MS m/z: 238.4 $[M+H]^+$; $^1$H-NMR (400 MHz, DMSO d6): δ 3.65 (s, 2H); 3.74 (s, 2H); 7.10-7.20 (m, 2H); 7.25-7.32 (m, 4H); 7.40-7.55 (m, 2H); 8.11 (s, 1H); 12.28 (br s, 1H); HPLC (METHOD [A]): rt 4.98 min (95.0%)

Example 3

N-Phenethyl-1H-benzo[d]imidazol-5-amine

The compound was synthesized starting from 5-bromobenzimidazole (200 mg; 1 mmol; 1 eq.), phenylethylamine (146 mg; 0.152 ml; 1.2 mmol; 1.2 eq.), 2-dicyclohexylphosphino-2'-(N,N-dimethylamino)biphenyl (9 mg; 0.024 mmol; 0.024 eq.; 2.4 mol %), $Pd_2$ $dba_3$ (9 mg; 0.01 mmol; 0.01 eq.; 1 mol %) and lithiumbis(trimethylsilyl)amide 1 M in THF (2.2 ml; 2.2 mmol; 2.2 eq.) according to method 1; Yield: 0.051 g (21.5%); MS m/z: 238.3 $[M+H]^+$; $^1$H-NMR (500 MHz, DMSO d6): δ 2.86 (t, 2H, $^3$J=7.6 Hz); 3.25 (t, 2H, $^3$J=7.6 Hz); 6.59 (dd, 1H, $^4$J=2.1 Hz, $^3$J=8.5 Hz); 6.62 (br s, 1H); 7.18-7.22 (m, 1H); 7.27-7.31 (m, 5H); 7.92 (s, 1H); HPLC (METHOD [A]): rt 11.20 min (84.4%)

Example 4

N-(4-Methoxybenzyl)-3H-benzo[d]imidazol-5-amine

The compound was synthesized starting from 5-bromobenzimidazole (200 mg; 1 mmol; 1 eq.), 4-methoxybenzylamine (165 mg; 0.156 ml; 1.2 mmol; 1.2 eq.), 2-dicyclohexylphosphino-2'-(N,N-dimethylamino)biphenyl (9 mg; 0.024 mmol; 0.024 eq.; 2.4 mol %), $Pd_2$ $dba_3$ (9 mg; 0.01 mmol; 0.01 eq.; 1 mol %) and lithiumbis(trimethylsilyl)amide 1 M in THF (2.2 ml; 2.2 mmol; 2.2 eq.) according to method 1; Yield: 0.058 g (22.9%); MS m/z: 254.3 $[M+H]^+$; $^1$H-NMR (500 MHz, DMSO d6): δ 3.69 (s, 3H); 4.19 (d, 2H, $^3$J=5.8 Hz); 5.97-5.99 (br m, 1H); 6.46 (br s, 1H); 6.57-6.59 (m, 1H); 6.64 (br s, 1H); 6.85-6.86 (m, 2H); 7.27-7.29 (m, 2H); 7.79 (s, 1H); 11.77 (br s, 1H); HPLC METHOD [A]: rt 10.12 min (95.6%)

Alternatively the compound was synthesized starting from benzimidazol-5-amine (2.66 g; 20 mmol; 1 eq.), 4-methoxybenzaldehyde (3.26 g; 2.9 ml; 24 mmol; 1.2 eq.), $NaBH_4$ (1.14 g; 30 mmol; 1.5 eq.) and 5 N NaOH (20 ml; 100 mmol; 5 eq.) according to method 2; Yield: 4.53 g (89.5%); MS m/z: 254.3 $[M+H]^+$

Example 5

N-(3,4-Dimethoxybenzyl)-3H-benzo[d]imidazol-5-amine

The compound was synthesized starting from 5-bromobenzimidazole (200 mg; 1 mmol; 1 eq.), 3,4-dimethoxybenzylamine (201 mg; 0.181 ml; 1.2 mmol; 1.2 eq.), 2-dicyclohexylphosphino-2'-(N,N-dimethylamino)biphenyl (9 mg; 0.024 mmol; 0.024 eq.; 2.4 mol %), $Pd_2$ $dba_3$ (9 mg; 0.01 mmol; 0.01 eq.; 1 mol %) and lithiumbis(trimethylsilyl)amide 1 M in THF (2.2 ml; 2.2 mmol; 2.2 eq.) according to method 1; Yield: 0.064 g (22.6%); MS m/z: 284.1 $[M+H]^+$; $^1$H-NMR (500 MHz, DMSO d6): δ 3.69 (s, 3H); 3.71 (s, 3H); 4.17 (d, 2H, $^3$J=5.8 Hz); 5.96 (br s, 1H); 6.48 (br s, 1H); 6.58-6.60 (m, 1H); 6.85-6.89 (m, 2H); 6.99 (s, 1H); 7.27-7.29 (m, 1H); 7.80 (s, 1H); 11.78 (br s, 1H); HPLC (METHOD [A]): rt 8.92 min (100%)

Example 6

N-(4-Chlorobenzyl)-3H-benzo[d]imidazol-5-amine

The compound was synthesized starting from 5-bromobenzimidazole (200 mg; 1 mmol; 1 eq.), 4-chlorobenzylamine (170 mg; 0.146 ml; 1.2 mmol; 1.2 eq.), 2-dicyclohexylphosphino-2'-(N,N-dimethylamino)biphenyl (9 mg; 0.024 mmol; 0.024 eq.; 2.4 mol %), $Pd_2$ $dba_3$ (9 mg; 0.01 mmol; 0.01 eq.; 1 mol %) and lithiumbis(trimethylsilyl)amide 1 M in THF (2.2 ml; 2.2 mmol; 2.2 eq.) according to method 1; Yield: 0.064 g (24.9%); MS m/z: 258.3 $[M+H]^+$; $^1$H-NMR (500 MHz, DMSO d6): δ 4.26 (d, 2H, $^3$J=5.8 Hz); 6.13 (br s, 1H); 6.43 (br s, 1H); 6.58-6.59 (m, 1H); 7.16-7.17 (m, 1H); 7.33-7.35 (m, 2H); 7.37-7.39 (m, 2H); 7.81 (br s, 1H); 11.78 (br s, 1H); HPLC (METHOD [A]): rt 11.80 min (92.7%)

Alternatively the compound was synthesized starting from benzimidazol-5-amine (2.66 g; 20 mmol; 1 eq.), 4-chlorobenzaldehyde (3.09 g; 22 mmol; 1.1 eq.), $NaBH_4$ (1.14 g; 30 mmol; 1.5 eq.) and 5 N NaOH (20 ml; 100 mmol; 5 eq.) according to method 2; Yield: 3.94 g (76.7%); MS m/z: 258.3/260.3 [M+H]$^+$

Example 7

N-(1-Phenylethyl)-3H-benzo[d]imidazol-5-amine

The compound was synthesized starting from 5-bromobenzimidazole (200 mg; 1 mmol; 1 eq.), 1-phenylethylamine (145 mg; 0.154 ml; 1.2 mmol; 1.2 eq.), 2-dicyclohexylphosphino-2'-(N,N-dimethylamino)biphenyl (9 mg; 0.024 mmol; 0.024 eq.; 2.4 mol %), Pd$_2$ dba$_3$ (9 mg; 0.01 mmol; 0.01 eq.; 1 mol %) and lithiumbis(trimethylsilyl)amide 1 M in THF (2.2 ml; 2.2 mmol; 2.2 eq.) according to method 1; Yield: 0.069 mg (29.1%); MS m/z: 238.1 [M+H]$^+$; $^1$H-NMR (500 MHz, DMSO d6): δ 1.42 (d, 3H, $^3$J=7.0 Hz); 4.44 (quin, 1H, $^3$J=6.7 Hz); 5.97 (br s, 1H); 6.34 (br s, 1H); 6.59-6.60 (m, 1H); 7.13-7.16 (m, 1H); 7.24-7.28 (m, 3H); 7.38-7.39 (m, 2H); 7.77 (s, 1H); 11.74 (br s, 1H); HPLC (METHOD [A]): rt 11.42 min (90.3%)

Example 8

N-(4-Methylbenzyl)-3H-benzo[d]imidazol-5-amine

The compound was synthesized starting from 5-bromobenzimidazole (200 mg; 1 mmol; 1 eq.), 4-methylbenzylamine (145 mg; 1.2 mmol; 1.2 eq.), 2-dicyclohexylphosphino-2'-(N,N-dimethylamino)biphenyl (9 mg; 0.024 mmol; 0.024 eq.; 2.4 mol %), Pd$_2$ dba$_3$ (9 mg; 0.01 mmol; 0.01 eq.; 1 mol %) and lithiumbis(trimethylsilyl)amide 1 M in THF (2.2 ml; 2.2 mmol; 2.2 eq.) according to method 1; Yield: 0.058 g (24.5%); MS m/z: 238.3 [M+H]$^+$; $^1$H-NMR (500 MHz, DMSO d6): δ 2.24 (s, 3H); 4.21 (s, 2H); 5.97 (br s, 1H); 6.49 (s, 1H); 6.59 (dd, 1H, $^4$J=1.8 Hz, $^3$J=8.5 Hz); 7.08-7.10 (m, 2H); 7.24-7.26 (m, 3H); 7.82 (s, 1H); 11.82 (br s, 1H); HPLC (METHOD [A]): rt 11.87 min (96.2%)

Example 9

N-(4-Fluorobenzyl)-3H-benzo[d]imidazol-5-amine

The compound was synthesized starting from 5-bromobenzimidazole (200 mg; 1 mmol; 1 eq.), 4-fluorobenzylamine (150 mg; 0.137 ml; 1.2 mmol; 1.2 eq.), 2-dicyclohexylphosphino-2'-(N,N-dimethylamino)biphenyl (9 mg; 0.024 mmol; 0.024 eq.; 2.4 mol %), Pd$_2$ dba$_3$ (9 mg; 0.01 mmol; 0.01 eq.; 1 mol %) and lithiumbis(trimethylsilyl)amide 1 M in THF (2.2 ml; 2.2 mmol; 2.2 eq.) according to method 1; Yield: 0.096 mg (39.8%); MS m/z: 242.4 [M+H]$^+$; $^1$H-NMR (500 MHz, DMSO d6): δ 4.25 (s, 2H); 6.04 (br s, 1H); 6.50 (s, 1H); 6.59 (dd, 1H, $^4$J=1.2 Hz, $^3$J=8.5 Hz); 7.09-7.13 (m, 2H); 7.26 (d, 1H, $^3$J=8.5 Hz); 7.38-7.41 (m, 2H); 7.83 (s, 1H); 11.88 (br s, 1H); HPLC (METHOD [A]): rt 11.21 min (99.2%)

Example 10

N,N-Dibenzyl-1H-benzo[d]imidazol-5-amine

The compound was synthesized starting from 5-bromobenzimidazole (200 mg; 1 mmol; 1 eq.), dibenzylamine (0.231 ml; 1.2 mmol; 1.2 eq.), 2-dicyclohexylphosphino-2'-(N,N-dimethylamino)biphenyl (9 mg; 0.024 mmol; 0.024 eq.; 2.4 mol %), Pd$_2$ dba$_3$ (9 mg; 0.01 mmol; 0.01 eq.; 1 mol %) and lithiumbis(trimethylsilyl)amide 1 M in THF (2.2 ml; 2.2 mmol; 2.2 eq.) according to method 1 but purified by flash chromatography on silica using a CHCl$_3$/MeOH gradient; Yield: 0.127 g (41%); 314.1 MS m/z: [M+H]$^+$; $^1$H-NMR (500 MHz, DMSO d6): δ 4.67 (s, 4H); 6.70 (br s, 1H); 6.73 (dd, 1H, $^4$J=2.4 Hz, $^3$J=8.9 Hz); 7.19-7.23 (m, 2H); 7.28-7.33 (m, 9H); 7.90 (s, 1H); 11.91 (br s, 1H); HPLC (METHOD [A]): rt 14.79 min (99.2%)

Example 11

N-(4-(Methylthio)benzyl)-1H-benzo[d]imidazol-5-amine

The compound was synthesized starting from benzimidazol-5-amine (2.66 g; 20 mmol; 1 eq.), 4-methylthiobenzaldehyde (3.35 g; 2.9 ml; 22 mmol; 1.1 eq.), NaBH$_4$ (1.14 g; 30 mmol; 1.5 eq.) and 5 N NaOH (20 ml; 100 mmol; 5 eq.) according to method 2; Yield: 3.79 g (70.5%); MS m/z: 270.5 [M+H]$^+$

Example 11

(Alternative Procedure): N-(4-(Methylthio)benzyl)-1H-benzo[d]imidazol-5-amine

The product was isolated from the synthesis of example 26 according to method 5. Yield: 0.055 (20.4%); MS m/z: 270.5 [M+H]$^+$; $^1$H-NMR (500 MHz, DMSO d6): δ 2.41 (s, 3H); 4.22 (s, 2H); 6.02 (br s, 1H); 6.48 (d, 1H, $^4$J=2.0 Hz); 6.59 (dd, 1H, $^4$J=2.2 Hz, $^3$J=8.6 Hz); 7.18-7.20 (m, 2H); 7.26 (d, 1H, $^3$J=8.6 Hz); 7.29-7.31 (m, 2H); 7.83 (s, 1H); 11.87 (br s, 1H); HPLC (METHOD [A]): rt 11.97 min (94.2%)

Example 12

N-(4-Ethylbenzyl)-1H-benzo[d]imidazol-5-amine

The compound was synthesized starting from benzimidazol-5-amine (2.66 g; 20 mmol; 1 eq.), 4-ethylbenzaldehyde (2.95 g; 3.02 ml; 22 mmol; 1.1 eq.), NaBH$_4$ (1.14 g; 30 mmol; 1.5 eq.) and 5 N NaOH (20 ml; 100 mmol; 5 eq.) according to method 2; Yield: 3.31 g (65.9%); MS m/z: 252.4 [M+H]$^+$; $^1$H-NMR (500 MHz, DMSO d6): δ 1.14 (t, 3H, $^3$J=7.6 Hz); 2.56 (q, 2H, $^3$J=7.6 Hz); 4.22 (s, 2H); 5.98 (br s, 1H); 6.51 (br s); 6.61 (dd, 1H, $^4$J=2.2 Hz, $^3$J=8.6 Hz); 7.13-7.14 (m, 2H); 7.26-7.29 (m, 3H); 7.83 (s, 1H); 11.84 (br s, 1H)

Example 13

N-(4-(Dimethylamino)benzyl)-1H-benzo[d]imidazol-5-amine

The compound was synthesized starting from benzimidazol-5-amine (2.66 g; 20 mmol; 1 eq.), 4-dimethylaminobenzaldehyd (3.28 g; 22 mmol; 1.1 eq.), NaBH$_4$ (1.14 g; 30 mmol; 1.5 eq.) and 5 N NaOH (20 ml; 100 mmol; 5 eq.) according to method 2; Yield: 3.24 g (61.0%); MS m/z: 166.3; $^1$H-NMR (500 MHz, DMSO d6): δ 2.83 (s, 6H); 4.13 (s, 2H); 5.83 (br s, 1H); 6.53 (br s, 1H); 6.60 (dd, 1H, $^4$J=2.1 Hz, $^3$J=8.5 Hz); 6.66-6.68 (m, 2H); 7.17-7.20 (m, 2H); 7.25-7.26 (m, 1H); 7.83 (s, 1H); 11.86 (br s, 1H)

Example 14

N-(Cyclohexylmethyl)-1H-benzo[d]imidazol-5-amine

The compound was synthesized starting from benzimidazol-5-amine (399 mg; 3 mmol; 1 eq.), cyclohexylmethylaldehyde (370 mg; 0.400 ml; 3.3 mmol; 1.1 eq.) and NaBH$_4$ (228 mg; 6 mmol; 2 eq.) as described in method 3; Yield: 0.389 g (56.6%); MS m/z: 230.4 [M+H]$^+$; $^1$H-NMR (400 MHz, DMSO d6): δ 0.90-0.99 (m, 2H); 1.13-1.25 (m, 3H); 1.52-1.70 (m, 4H); 1.79-1.83 (m, 2H); 2.84 (d, 2H, $^3$J=6.6 Hz); 5.37 (br s, 1H); 6.53 (br s, 1H); 6.55 (dd, 1H, $^4$J=2.1 Hz, $^3$J=8.7 Hz); 7.25 (d, 1H, $^3$J=8.7 Hz); 7.83 (s, 1H); 11.83 (br s, 1H); HPLC (METHOD [A]): rt 12.20 min (98.9%)

Example 15

N-Butyl-1H-benzo[d]imidazol-5-amine

The compound was synthesized starting from benzimidazol-5-amine (399 mg; 3 mmol; 1 eq.), n-butanal (238 mg; 0.291 ml; 3.3 mmol; 1.1 eq.) and NaBH$_4$ (228 mg; 6 mmol; 2 eq.) as described in method 3; Yield: 0.311 (54.9%); MS m/z: 190.4 [M+H]$^+$; $^1$H-NMR (400 MHz, DMSO d6): δ 0.91 (t, 3H, $^3$J=7.5 Hz); 1.35-1.44 (m, 2H); 1.52-1.59 (m, 2H); 2.99 (t, 2H, $^3$J=7.1 Hz); 5.27 (br s, 1H); 6.53-6.55 (m, 2H); 7.25-7.27 (m, 1H); 7.84 (s, 1H); 11.83 (br s, 1H); HPLC (METHOD [A]): rt 7.51 min (95.9%)

Example 16

N-(Pentan-2-yl)-1H-benzo[d]imidazol-5-amine

The compound was synthesized starting from benzimidazol-5-amine (399 mg; 3 mmol; 1 eq.), 2-pentanal (284 mg; 0.351 ml; 3.3 mmol; 1.1 eq) and NaBH$_4$ (228 mg; 6 mmol; 2 eq.) as described in method 3; Yield: 0.264 g (43.3%); MS m/z: 204.4 [M+H]$^+$; $^1$H-NMR (400 MHz, DMSO d6): δ 0.88 (t, 3H, $^3$J=7.5 Hz); 1.10 (d, 3H, $^3$J=6.2 Hz); 1.32-1.42 (m, 3H); 1.49-1.56 (m, 1H); 3.35-3.37 (m, 1H); 5.02 (br s, 1H); 6.52-6.55 (m, 2H); 7.25 (d, 1H, $^3$J=8.7 Hz); 7.83 (s, 1H); 11.81 (br s, 1H); HPLC (METHOD [A]): rt 7.79 min (80.5%)

Example 17

N-Isobutyl-1H-benzo[d]imidazol-5-amine

The compound was synthesized starting from benzimidazol-5-amine (399 mg; 3 mmol; 1 eq.), isobutylaldehyde (238 mg; 0.301 ml; 3.3 mmol; 1.1 eq.) and NaBH$_4$ (228 mg; 6 mmol; 2 eq.) as described in method 3; Yield: 0.246 g (43.4%); MS m/z: 190.4 [M+H]$^+$; $^1$H-NMR (400 MHz, DMSO d6): δ 0.94 (d, 6H, $^3$J=6.6 Hz); 1.86 (hept, 1H, $^3$J=6.6 Hz); 2.81 (d, 2H, $^3$J=7.1 Hz); 5.35 (br s, 1H); 6.54-6.58 (m, 2H); 7.26 (d, 1H, $^3$J=8.7 Hz); 7.84 (s, 1H); 11.82 (br s, 1H); HPLC (METHOD [A]): rt 8.10 min (87.0%)

Example 18

N,N-Bis(2,4,5-trifluorobenzyl)-1H-benzo[d]imidazol-5-amine

The compound was synthesized starting from N$_1$-Boc-benzimidazol-5-amine (233 mg; 1 mmol; 1 eq.), 2,4,5-trifluorbenzylbromide (563 mg; 2.5 mmol; 2.5 eq.) and K$_2$CO$_3$ (345 mg; 2.5 mmol; 2.5 eq.) according to method 4; Yield: 0.172 (40.9%); MS m/z: 422.2 [M+H]$^+$; $^1$H-NMR (500 MHz, DMSO d6): δ 4.68 (s, 4H); 6.74 (dd, 1H, $^4$J=2.1 Hz, $^3$J=8.9 Hz); 6.78 (br s, 1H); 7.23-7.29 (m, 2H); 7.39 (d, 1H, $^3$J=8.9 Hz); 7.51-7.56 (m, 2H); 7.97 (s, 1H); 12.03 (br s, 1H); HPLC (METHOD [A]): rt 16.46 min (100%)

Example 19

N,N-Bis(4-cyanobenzyl)-1H-benzo[d]imidazol-5-amine

The compound was synthesized starting from N$_1$-Boc-benzimidazol-5-amine (233 mg; 1 mmol; 1 eq.), 4-bromomethylbenzonitrile (490 mg; 2.5 mmol; 2.5 eq.) and K$_2$CO$_3$ (345 mg; 2.5 mmol; 2.5 eq.) according to method 4; Yield: 0.176 g (48.4%); MS m/z: 364.2 [M+H]$^+$; $^1$H-NMR (500 MHz, DMSO d6): δ 4.80 (s, 4H); 6.66-6.68 (m, 2H); 7.34 (d, 1H, $^3$J=8.7 Hz); 7.47 (d, 4H, $^3$J=8.3 Hz); 7.78 (d, 4H, $^3$J=8.3 Hz); 7.92 (s, 1H); 11.95 (br s, 1H); HPLC (METHOD [A]): rt 13.50 min (100%)

Example 20

N,N-Bis((4-methylbenzyl)-1H-benzo[d]imidazol-5-amine

The compound was synthesized starting from benzimidazol-5-amine (133 mg; 1 mmol; 1 eq.), 4-methylbenzylbromide (407 mg; 2.2 mmol; 2.2 eq.) and K$_2$CO$_3$ (304 mg; 2.2 mmol; 2.2 eq.) according to method 5; Yield: 0.109 g (32.0%); MS m/z: 342.1 [M+H]$^+$; $^1$H-NMR (500 MHz, DMSO d6): δ 2.23 (s, 6H); 4.57 (s, 4H); 6.66 (br s, 1H); 6.71 (dd, 1H, $^4$J=2.1 Hz, $^3$J=8.9 Hz); 7.09 (d, 4H, $^3$J=7.9 Hz); 7.14 (d, 4H, $^3$J=7.9 Hz); 7.30 (d, 1H, $^3$J=8.5 Hz); 7.88 (s, 1H); 11.88 (br s, 1H); HPLC (METHOD [A]): rt 17.36 min (98.1%)

Example 21

N,N-Bis(4-isopropylbenzyl)-1H-benzo[d]imidazol-5-amine

The compound was synthesized starting from benzimidazol-5-amine (133 mg; 1 mmol; 1 eq.), 4-isopropylbenzylbromide (469 mg; 0.376 ml; 2.2 mmol; 2.2 eq.) and K$_2$CO$_3$ (304 mg; 2.2 mmol; 2.2 eq.) according to method 5; Yield: 0.147 g (36.9%); MS m/z: 398.4 [M+H]$^+$; 1H-NMR (500 MHz, DMSO d6): δ 1.16 (d, 12H, $^3$J=7.0 Hz); 2.83 (hept, 2H, $^3$J=7.0 Hz); 4.62 (s, 4H); 6.69 (br s, 1H); 6.73 (dd, 1H, $^4$J=2.4 Hz, $^3$J=8.9 Hz); 7.16-7.20 (m, 8H); 7.32 (d, 1H, $^3$J=8.9 Hz); 7.89 (s, 1H); 11.90 (br s, 1H); HPLC (METHOD [A]): rt 19.95 min (94.4%)

Example 22

N,N-Bis(4-tert-butylbenzyl)-1H-benzo[d]imidazol-5-amine

The compound was synthesized starting from benzimidazol-5-amine (133 mg; 1 mmol; 1 eq.), 4-tert-butylbenzylbromide (500 mg; 2.2 mmol; 2.2 eq.) and K$_2$CO$_3$ (304 mg; 2.2 mmol; 2.2 eq.) according to method 5; Yield: 0.250 g (58.7%); MS m/z: 426.3 [M+H]$^+$; $^1$H-NMR (500 MHz, DMSO d6): δ 1.24 (s, 18H); 4.62 (s, 4H); 6.69 (br s, 1H); 6.74 (dd, 1H, $^4$J=2.1 Hz, $^3$J=8.9 Hz); 7.17-7.22 (m, 4H); 7.31-7.33 (m, 5H); 7.94 (s, 1H); 11.89 (br s, 1H); HPLC (METHOD [A]): rt 20.49 min (86.5%)

Example 23

N,N-Bis(4-methoxybenzyl)-1H-benzo[d]imidazol-5-amine

The compound was synthesized starting from benzimidazol-5-amine (133 mg; 1 mmol; 1 eq.), 4-methoxybenzylbromide (442 mg; 0.317 ml; 2.2 mmol; 2.2 eq.) and K₂CO₃ (304 mg; 2.2 mmol; 2.2 eq.) according to method 5; Yield: 0.137 mg (36.7%); MS m/z: 374.1 [M+H]⁺; ¹H-NMR (500 MHz, DMSO d6): δ 3.70 (s, 6H), 4.54 (s, 4H); 6.71 (d, 1H, $^4J$=2.2 Hz); 6.78 (dd, 1H, $^4J$=2.4 Hz, $^3J$=8.9 Hz); 6.84-6.87 (m, 4H); 7.17-7.20 (m, 4H); 7.33 (d, 1H, $^3J$=8.9 Hz); 7.93 (s, 1H); 12.03 (br s, 1H); HPLC (METHOD [A]): rt 15.56 min (99.5%)

Example 24

N,N-Bis(3-methoxybenzyl)-1H-benzo[d]imidazol-5-amine

The compound was synthesized starting from benzimidazol-5-amine (133 mg; 1 mmol; 1 eq.), 3-methoxybenzylbromide (442 mg; 0.308 ml; 2.2 mmol; 2.2 eq.) and K₂CO₃ (304 mg; 2.2 mmol; 2.2 eq.) according to method 5; Yield: 0.143 g (38.3%); MS m/z: 374.1 [M+H]⁺; ¹H-NMR (500 MHz, DMSO d6): δ 3.68 (s, 6H); 4.64 (s, 4H); 6.69 (br s, 1H); 6.72 (dd, 1H, $^4J$=2.1 Hz, $^3J$=8.9 Hz); 6.78 (dd, 2H, $^4J$=2.4 Hz, $^3J$=7.9 Hz); 6.83-6.87 (m, 4H); 7.22 (t, 2H, $^3J$=7.9 Hz); 7.33 (d, 1H, $^3J$=8.9 Hz); 7.90 (s, 1H); 11.92 (br s, 1H); HPLC (METHOD [A]): rt 15.00 min (92.7%)

Example 25

N,N-Bis((3,4-dihydro-2H-benzo[b][1,4]dioxepin-9-yl)methyl)-1H-benzo[d]imidazol-5-amine The compound was synthesized starting from benzimidazol-5-amine (133 mg; 1 mmol; 1 eq.), 6-(bromomethyl)-3,4-dihydro-1,5-benzodioxepin (535 mg; 2.2 mmol; 2.2 eq.) and K₂CO₃ (304 mg; 2.2 mmol; 2.2 eq.) according to method 5; Yield: 0.098 g (21.4%); MS m/z: 458.5 [M+H]⁺; ¹H-NMR (500 MHz, DMSO d6): δ 2.10 (quin, 4H, $^3J$=5.5 Hz); 4.10 (t, 4H, $^3J$=5.5 Hz); 4.15 (t, 4H, $^3J$=5.5 Hz); 4.61 (s, 4H); 6.58-6.60 (m, 2H); 6.76-6.85 (m, 6H); 7.31 (d, 1H, $^3J$=9.8 Hz); 7.88 (s, 1H); 11.89 (br s, 1H); HPLC (METHOD [A]): rt 16.11 min (92.3%)

Example 26

N,N-Bis(4-(methylthio)benzyl)-1H-benzo[d]imidazol-5-amine

The compound was synthesized starting from benzimidazol-5-amine (133 mg; 1 mmol; 1 eq.), 4-methylthiobenzylbromide (478 mg; 2.2 mmol; 2.2 eq.) and K₂CO₃ (304 mg; 2.2 mmol; 2.2 eq.) according to method 5; Yield: 0.182 g (44.9%); MS m/z: 406.4 [M+H]⁺; ¹H-NMR (500 MHz, DMSO d6): δ 2.48 (s, 6H); 4.58 (s, 4H); 6.67 (br s, 1H); 6.72 (dd, 1H, $^4J$=2.3 Hz, $^3J$=8.8 Hz); 7.17-7.21 (m, 8H); 7.31 (d, 1H, $^3J$=8.8 Hz); 7.89 (s, 1H); 11.90 (br s, 1H); HPLC (METHOD [A]): rt 17.86 min (96.3%)

Example 27

N,N-Bis(4-bromobenzyl)-1H-benzo[d]imidazol-5-amine

The compound was synthesized starting from benzimidazol-5-amine (133 mg; 1 mmol; 1 eq.), 4-bromobenzylbromide (550 mg; 2.2 mmol; 2.2 eq.) and K₂CO₃ (304 mg; 2.2 mmol; 2.2 eq.) according to method 5; Yield: 0.153 g (32.5%); MS m/z: 472.3 [M+H]⁺; ¹H-NMR (500 MHz, DMSO d6): δ 4.63 (s, 4H); 6.66-6.67 (m, 1H); 6.71 (dd, 1H, $^4J$=2.4 Hz, $^3J$=8.9 Hz); 7.22-7.24 (m, 4H); 7.34 (d, 1H, $^3J$=8.9 Hz); 7.48-7.50 (m, 4H); 7.93 (s, 1H); 11.99 (br s, 1H); HPLC (METHOD [A]): rt 18.49 min (98.4%)

Example 28

N,N-Bis(3-bromobenzyl)-1H-benzo[d]imidazol-5-amine

The compound was synthesized starting from benzimidazol-5-amine (133 mg; 1 mmol; 1 eq.), 3-bromobenzylbromide (550 mg; 2.2 mmol; 2.2 eq.) and K₂CO₃ (304 mg; 2.2 mmol; 2.2 eq.) according to method 5; Yield: 0.227 g (48.2%); MS m/z: 470.1/472.2/474.1 [M+H]⁺; ¹H-NMR (500 MHz, DMSO d6): δ 4.70 (s, 4H); 6.68-6.70 (m, 2H); 7.26-7.27 (m, 4H); 7.34 (d, 1H, $^3J$=8.6 Hz); 7.39-7.41 (m, 2H); 7.43 (s, 2H); 7.91 (s, 1H); 11.93 (br s, 1H); HPLC (METHOD [A]): rt 17.81 min (98.3%)

Example 29

N,N-Bis(2-fluorobenzyl)-1H-benzo[d]imidazol-5-amine

The compound was synthesized starting from benzimidazol-5-amine (133 mg; 1 mmol; 1 eq.), 2-fluorobenzylbromide (416 mg; 0.265 ml; 2.2 mmol; 2.2 eq.) and K₂CO₃ (304 mg; 2.2 mmol; 2.2 eq.) according to method 5; Yield: 0.063 g (18.1%); MS m/z: 350.2 [M+H]⁺; ¹H-NMR (500 MHz, DMSO d6): δ 4.73 (s, 4H); 6.71-6.72 (m, 2H); 7.08-7.11 (m, 2H); 7.17-7.19 (m, 2H); 7.20-7.28 (m, 4H); 7.32 (d, 1H, $^3J$=9.4 Hz); 7.92 (s, 1H); 11.94 (br s, 1H); HPLC (METHOD [A]): rt 15.61 min (100%)

Example 30

N,N-Bis(3,5-difluorobenzyl)-1H-benzo[d]imidazol-5-amine

The compound was synthesized starting from benzimidazol-5-amine (133 mg; 1 mmol; 1 eq.), 3,5-difluorobenzylbromide (455 mg; 0.285 ml; 2.2 mmol; 2.2 eq.) and K₂CO₃ (304 mg; 2.2 mmol; 2.2 eq.) according to method 5; Yield: 0.065 g (16.7%); MS m/z: 386.3 [M+H]⁺; ¹H-NMR (500 MHz, DMSO d6): δ 4.75 (s, 4H); 6.67-6.70 (m, 2H); 6.97-6.99 (m, 4H); 7.07 (tt, 2H, $^4J$=2.3 Hz, $^3J_{H,F}$=9.3 Hz); 7.36-7.37 (m, 1H); 7.94 (s, 1H); 11.96 (br s, 1H); HPLC (METHOD [A]): rt 16.26 min (100%)

Example 31

N,N-Bis(2-fluoro-3-methylbenzyl)-1H-benzo[d]imidazol-5-amine

The compound was synthesized starting from benzimidazol-5-amine (133 mg; 1 mmol; 1 eq.), 2-fluoro-3-methylbenzylbromide (447 mg; 2.2 mmol; 2.2 eq.) and K₂CO₃ (304 mg; 2.2 mmol; 2.2 eq.) according to method 5; Yield: 0.072 g (19.1%); MS m/z: 378.1 [M+H]⁺; ¹H-NMR (500 MHz, DMSO d6): δ 2.24 (d, 6H, $^4J_{H,F}$=1.5 Hz); 4.71 (s, 4H); 6.67-6.69 (m, 2H); 6.98 (t, 2H, $^3J$=7.5 Hz); 7.03-7.06 (m, 2H); 7.13-7.15 (m, 2H), 7.33-7.35 (m, 1H); 7.92 (s, 1H); 11.95 (br s, 1H); HPLC (METHOD [A]): rt 17.77 min (83.5%)

Example 32

N,N-Bis(4-(thiophen-2-yl)benzyl)-1H-benzo[d]imidazol-5-amine

The compound was synthesized starting from benzimidazol-5-amine (133 mg; 1 mmol; 1 eq.), 4-(thiophen-2-yl)benzylbromide (557 mg; 2.2 mmol; 2.2 eq.) and K$_2$CO$_3$ (304 mg; 2.2 mmol; 2.2 eq.) according to method 5; Yield: 0.09 g (18.9%); MS m/z: 478.4 [M+H]$^+$; $^1$H-NMR (500 MHz, DMSO d6): δ 4.70 (s, 4H); 6.73 (br s, 1H); 6.78 (dd, 1H, $^4$J=2.1 Hz, $^3$J=8.9 Hz); 7.10-7.11 (m, 2H); 7.33-7.36 (m, 5H); 7.45 (dd, 2H); 7.49 (dd, 2H); 7.59-7.60 (m, 4H); 7.91 (s, 1H); 11.99 (br s, 1H); HPLC (METHOD [A]): rt 19.76 min (100%)

Example 33

N,N-Bis((naphthalen-2-yl)methyl))-1H-benzo[d]imidazol-5-amine

The compound was synthesized starting from benzimidazol-5-amine (133 mg; 1 mmol; 1 eq.), naphthalen-2-yl-methylbromide (486 mg; 2.2 mmol; 2.2 eq.) and K$_2$CO$_3$ (304 mg; 2.2 mmol; 2.2 eq.) according to method 5; Yield: 0.12 g (29.1%); MS m/z: 414.5 [M+H]$^+$; $^1$H-NMR (500 MHz, DMSO d6): δ 4.93 (s, 4H); 6.81 (br s, 1H); 6.84 (dd, 1H, $^4$J=2.1 Hz, $^3$J=8.9 Hz); 7.34 (d, 1H, $^3$J=8.9 Hz); 7.43-7.48 (m, 4H); 7.51 (dd, 2H); 7.80-7.83 (m, 4H); 7.83-7.87 (m, 4H); 7.89 (s, 1H); 11.90 (br s, 1H); HPLC (METHOD [A]): rt 19.13 min (96.98%)

Example 34

N,N-Bis((benzo[d]thiazol-2-yl)methyl)-1H-benzo[d]imidazol-5-amine

The compound was synthesized starting from benzimidazol-5-amine (133 mg; 1 mmol; 1 eq.), (benzo[d]thiazol-2-yl)methylbromide (502 mg; 2.2 mmol; 2.2 eq.) and K$_2$CO$_3$ (304 mg; 2.2 mmol; 2.2 eq.) according to method 5; Yield: 0.037 g (8.7%); 428.1 MS m/z: [M+H]$^+$; $^1$H-NMR (500 MHz, DMSO d6): δ 5.22 (s, 4H); 6.96 (dd, 1H, $^4$J=2.4 Hz, $^3$J=8.9 Hz); 7.02 (br s, 1H); 7.38-7.43 (m, 3H); 7.47-7.51 (m, 2H); 7.96-7.98 (m, 2H); 8.02-8.03 (m, 3H); 12.35 (br s, 1H); HPLC (METHOD [A]): rt 14.45 min (92.1%)

Example 35

N,N-Bis-((benzo[c][1,2,5]thiadiazol-5-yl)methyl)-1H-benzo[d]imidazol-5-amine

The compound was synthesized starting from benzimidazol-5-amine (133 mg; 1 mmol; 1 eq.), benzo[c][1,2,5]thiadiazol-5-yl-methylbromide (504 mg; 2.2 mmol; 2.2 eq.) and K$_2$CO$_3$ (304 mg; 2.2 mmol; 2.2 eq.) according to method 5; Yield: 0.128 mg (29.8%); MS m/z: 430.4 [M+H]$^+$; $^1$H-NMR (500 MHz, DMSO d6): δ 5.01 (s, 4H); 6.78 (br s, 1H); 6.82-6.84 (m, 1H); 7.39-7.41 (m, 1H); 7.71-7.73 (m, 2H); 7.88 (s, 1H); 7.90 (s, 2H); 8.06-8.08 (m, 2H); 11.85 (br s, 1H); HPLC (METHOD [A]): rt 14.11 min (98.9%)

Example 36

N,N-Bis((5-chlorobenzo[b]thiophen-3-yl)methyl)-1H-benzo[d]imidazol-5-amine

The compound was synthesized starting from benzimidazol-5-amine (133 mg; 1 mmol; 1 eq.), (5-chlorobenzo[b]thiophen-3-yl)methylbromide (576 mg; 2.2 mmol; 2.2 eq.) and K$_2$CO$_3$ (304 mg; 2.2 mmol; 2.2 eq.) according to method 5; Yield: 0.187 g (37.9%); MS m/z: 494.4/496.5 [M+H]$^+$; $^1$H-NMR (500 MHz, DMSO d6): δ 4.84 (s, 4H); 6.90-6.92 (m, 2H); 7.37-7.39 (m, 3H); 7.51 (s, 2H); 7.88 (d, 2H); 7.94-7.96 (m, 2H); 7.98 (s, 1H); 12.00 (br s, 1H); HPLC (METHOD [A]): rt 19.77 min (100%)

Example 37

N,N-Bis((2-methylquinolin-6-yl)methyl)-1H-benzo[d]imidazol-5-amine

The compound was synthesized starting from benzimidazol-5-amine (133 mg; 1 mmol; 1 eq.), (2-methylquinolin-6-yl)methylbromide (519 mg; 2.2 mmol; 2.2 eq.) and K$_2$CO$_3$ (304 mg; 2.2 mmol; 2.2 eq.) according to method 5; Yield: 0.067 g (15.1%); MS m/z: 444.5 [M+H]$^+$, 222.8 [M+2H]$^{2+}$; $^1$H-NMR (500 MHz, DMSO d6): δ 2.60 (s, 6H); 4.92 (s, 4H); 6.77-6.82 (m, 2H); 7.33-7.35 (m, 3H); 7.67 (dd, 2H, $^4$J=2.1 Hz, $^3$J=8.5 Hz); 7.77 (br s, 2H); 7.85-7.87 (m, 3H); 8.14 (d, 2H, $^3$J=8.5 Hz); 11.81 (br s, 1H); HPLC (METHOD [A]): doublepeak rt 6.61 min (61.2%), 6.84 min (38.8%)

Example 38

N-((3,4-Dihydro-2H-benzo[b][1,4]dioxepin-9-yl)methyl)-1H-benzo[d]imidazol-5-amine The product was isolated from the synthesis of example 25 according to method 5. Yield: 0.052 g (17.6%); MS m/z: 296.5 [M+H]$^+$; $^1$H-NMR (500 MHz, DMSO d6): δ 2.10-2.14 (m, 2H); 4.09-4.12 (m, 2H); 4.17-4.19 (m, 2H); 4.25 (s, 2H,); 5.86 (br s, 1H); 6.51 (d, 1H, $^4$J=2.1 Hz); 6.61 (dd, 1H, $^4$J=2.1 Hz, $^3$J=8.5 Hz); 6.83-6.84 (m, 2H); 6.97-6.99 (m, 1H); 7.27 (d, 1H, $^3$J=8.5 Hz); 7.86 (s, 1H); 11.92 (br s, 1H); HPLC (METHOD [A]): rt 10.70 min (86.8%)

Example 39

N-(3-Bromobenzyl)-1H-benzo[d]imidazol-5-amine

The product was isolated from the synthesis of example 28 according to method 5. Yield: 0.075 g (24.8%); MS m/z: 302.3/304.5 [M+H]$^+$; $^1$H-NMR (500 MHz, DMSO d6): δ 4.28 (s, 2H); 6.13 (br s, 1H); 6.481-6.485 (m, 1H); 6.59 (dd, 1H, $^4$J=2.2 Hz, $^3$J=8.6 Hz); 7.24-7.28 (m, 2H); 7.36-7.39 (m, 2H); 7.54-7.55 (m, 1H); 7.84 (s, 1H); 11.90 (br s, 1H); HPLC (METHOD [A]): rt 12.23 min (81.4%)

Example 40

N-(2,5-Dichlorobenzyl)-1H-benzo[d]imidazol-5-amine

The compound was synthesized starting from benzimidazol-5-amine (133 mg; 1 mmol; 1 eq.), 2,5-dichlorobenzylbromide (528 mg; 2.2 mmol; 2.2 eq.) and K$_2$CO$_3$ (304 mg; 2.2 mmol; 2.2 eq.) according to method 5. Yield: 0.045 g (15.4%); MS m/z: 292.2/294.3 [M+H]$^+$; $^1$H-NMR (500 MHz, DMSO d6): δ 4.32 (d, 2H, $^3$J=6.1 Hz); 6.20 (br s, 1H); 6.43 (br s, 1H); 6.60 (dd, 1H, $^4$J=1.6 Hz, $^3$J=8.8 Hz); 7.30-7.33 (m, 2H); 7.40 (d, 1H, $^4$J=2.6 Hz); 7.49 (d, 1H, $^3$J=8.5 Hz); 7.86 (s, 1H), 11.83 (br s, 1H); HPLC (METHOD [A]): rt 12.97 min (100%)

Example 41

N-(2-Fluorobenzyl)-1H-benzo[d]imidazol-5-amine

The product was isolated from the synthesis of example 29 according to method 5. Yield: 0.042 g (17.4%); MS m/z: 242.3 [M+H]$^+$; $^1$H-NMR (500 MHz, DMSO d6): δ 4.32 (d, 2H, $^3$J=5.8 Hz); 6.02 (br s, 1H); 6.53 (br s, 1H), 6.62 (dd, 1H, $^4J$=1.8 Hz, $^3J$=8.9 Hz); 7.10-7.13 (m, 1H); 7.15-7.19 (m, 1H); 7.25-7.30 (m, 2H); 7.40-7.43 (m, 1H); 7.85 (s, 1H); 11.84 (br s, 1H); HPLC (METHOD [A]): rt 10.27 min (93.4%)

Example 42

N-(3,5-Difluorobenzyl)-1H-benzo[d]imidazol-5-amine

The product was isolated from the synthesis of example 30 according to method 5. Yield: 0.053 g (20.5%); MS m/z: 260.3 [M+H]$^+$; $^1$H-NMR (500 MHz, DMSO d6): δ 4.32 (s, 2H); 6.21 (br s, 1H); 6.50 (d, 1H, $^4J$=1.9 Hz); 6.62 (dd, 1H, $^4J$=2.2 Hz, $^3J$=8.6 Hz); 7.01-7.10 (m, 3H); 7.30 (d, 1H, $^3J$=8.7 Hz); 7.92 (s, 1H); 12.06 (br s, 1H); HPLC (METHOD [A]): rt 11.11 min (99.3%)

Example 43

N-(2-Fluoro-3-methylbenzyl)-1H-benzo[d]imidazol-5-amine

The product was isolated from the synthesis of example 31 according to method 5. Yield: 0.061 g (23.9%); MS m/z: 256.5 [M+H]$^+$; $^1$H-NMR (500 MHz, DMSO d6): δ 2.24 (d, 3H, $^4J_{(H,F)}$=1.8 Hz); 4.30 (s, 2H); 5.97 (br s, 1H); 6.53 (d, 1H, $^4J$=1.7 Hz); 6.62 (dd, 1H, $^4J$=2.2 Hz, $^3J$=8.6 Hz); 6.99 (t, 1H, $^3J$=7.5 Hz); 7.12-7.14 (m, 1H); 7.20-7.23 (m, 1H); 7.29 (d, 1H, $^3J$=8.6 Hz); 7.85 (s, 1H); 11.87 (br s, 1H); HPLC (METHOD [A]): rt 11.47 min (99.6%)

Example 44

N-(2,3,5,6-Tetrafluoro-4-methylbenzyl)-1H-benzo[d]imidazol-5-amine

The compound was synthesized starting from benzimidazol-5-amine (133 mg; 1 mmol; 1 eq.), 2,3,5,6-tetrafluoro-4-methylbenzylbromide (566 mg; 2.2 mmol; 2.2 eq.) and K$_2$CO$_3$ (304 mg; 2.2 mmol; 2.2 eq.) according to method 5. Yield: 0.034 g (11.0%); MS m/z: 310.2 [M+H]$^+$; $^1$H-NMR (500 MHz, DMSO d6): δ 2.20 (t, 3H, $^3J_{(H,F)}$=1.9 Hz); 4.35 (d, 2H); 5.85 (br s, 1H); 6.60 (dd, 1H, $^4J$=1.8 Hz, $^3J$=8.5 Hz); 6.69 (br s, 1H); 7.28 (d, 1H, $^3J$=8.5 Hz); 7.87 (s, 1H); 11.95 (br s, 1H); HPLC (METHOD [A]): rt 13.04 min (100%)

Example 45

N-(4-(Thiophen-2-yl)benzyl)-1H-benzo[d]imidazol-5-amine

The product was isolated from the synthesis of example 32 according to method 5. Yield: 0.097 g (31.8%); MS m/z: 306.0 [M+H]$^+$; $^1$H-NMR (500 MHz, DMSO d6): δ 4.29 (d, 2H, $^3J$=5.2 Hz); 6.08 (br s, 1H); 6.52 (br s, 1H); 6.62 (dd, 1H, $^4J$=2.1 Hz, $^3J$=8.5 Hz); 7.09-7.11 (m, 1H); 7.28 (d, 1H, $^3J$=8.9 Hz); 7.40-7.42 (m, 2H); 7.44-7.45 (m, 1H); 7.48-7.50 (m, 1H); 7.58-7.60 (m, 2H); 7.83 (s, 1H); 11.83 (br s, 1H); HPLC (METHOD [A]): rt 13.99 min (95.1%)

Example 46

N-((Naphthalen-2-yl)methyl)-1H-benzo[d]imidazol-5-amine

The product was isolated from the synthesis of example 33 according to method 5. Yield: 0.072 g (26.4%); MS m/z: 274.2 [M+H]$^+$; $^1$H-NMR (500 MHz, DMSO d6): δ 4.44 (s, 2H); 6.17 (br s, 1H); 6.54 (d, 1H, $^4J$=2.0 Hz); 6.65 (dd, 1H, $^4J$=2.2 Hz, $^3J$=8.7 Hz); 7.27 (d, 1H, $^3J$=8.6 Hz); 7.41-7.47 (m, 2H); 7.53-7.55 (m, 1H); 7.81-7.86 (m, 5H); HPLC (METHOD [A]): rt 13.30 min (75.1%)

Example 47

N-((Benzo[d]thiazol-2-yl)methyl)-1H-benzo[d]imidazol-5-amine

The product was isolated from the synthesis of example 34 according to method 5. Yield: 0.043 g (15.4%); MS m/z: 281.3 [M+H]$^+$; $^1$H-NMR (500 MHz, DMSO d6): δ 4.70 (d, 2H, $^3J$=5.8 Hz); 6.60-6.62 (m, 2H); 6.67 (dd, 1H, $^4J$=2.1 Hz, $^3J$=8.9 Hz); 7.33 (d, 1H, $^3J$=8.9 Hz); 7.35-7.39 (m, 1H); 7.46-7.49 (m, 1H); 7.90 (s, 1H); 7.94-7.95 (m, 1H); 7.97-7.99 (m, 1H); 12.03 (br s, 1H); HPLC (METHOD [A]): rt 10.43 min (94.2%)

Example 48

N4(Benzo[c][1,2,5]thiadiazol-6-yl)methyl)-1H-benzo[d]imidazol-5-amine

The product was isolated from the synthesis of example 35 according to method 5. Yield: 0.044 g (15.7%); MS m/z: 282.4 [M+H]$^+$; $^1$H-NMR (500 MHz, DMSO d6): δ 4.51 (d, 2H, $^3J$=5.2 Hz); 6.30 (br s, 1H); 6.57 (br s, 1H); 6.66 (dd, 1H, $^4J$=2.1 Hz, $^3J$=8.5 Hz); 7.29 (d, 1H, $^3J$=8.5 Hz); 7.77 (dd, 1H, $^4J$=1.5 Hz, $^3J$=8.9 Hz); 7.83 (s, 1H); 8.00 (br s, 1H); 8.04 (d, 1H, $^3J$=8.9 Hz); 11.85 (br s, 1H); HPLC (METHOD [A]): rt 9.47 min (98.9%)

Example 49

N4(5-Chlorobenzo[b]thiophen-3-yl)methyl)-1H-benzo[d]imidazol-5-amine

The product was isolated from the synthesis of example 36 according to method 5. Yield: 0.064 g (20.4%); MS m/z: 314.3 [M+H]$^+$; $^1$H-NMR (500 MHz, DMSO d6): δ 4.50 (s, 2H); 6.05 (br s, 1H); 6.66-6.68 (m, 2H); 7.29-7.30 (m, 1H); 7.40 (dd, 1H, $^4J$=2.1 Hz, $^3J$=8.5 Hz); 7.69 (s, 1H); 7.86 (s, 1H); 8.01 (d, 1H, $^3J$=8.5 Hz); 8.06 (d, 1H, $^4J$=1.8 Hz); 11.90 (br s, 1H); HPLC (METHOD [A]): rt 13.89 min (97.9%)

Example 50

N((2-Methylquinolin-6-yl)methyl)-1H-benzo[d]imidazol-5-amine

The product was isolated from the synthesis of example 37 according to method 5. Yield: 0.011 g (3.8%); MS m/z: 289.1 [M+H]$^+$ 145.2 [M+2H]$^{2+}$; $^1$H-NMR (500 MHz, DMSO d6): δ 2.60 (s, 3H); 4.44 (s, 2H); 6.18 (br s, 1H); 6.54 (br s, 1H); 6.65 (dd, 1H, $^4J$=2.1 Hz, $^3J$=8.5 Hz); 7.28-7.31 (m, 1H); 7.35 (d, 1H, $^3J$=8.5 Hz); 7.72 (dd, 1H, $^4J$=2.1 Hz, $^3J$=8.5 Hz); 7.84-7.86 (m, 2H); 7.93 (s, 1H); 8.15 (d, 1H, $^3J$=8.2 Hz); 11.90 (br s, 1H); HPLC (METHOD [A]): rt 5.63 min (87.9%)

Example 51

N-(4-(Methylthio)benzyl)-N-benzyl-1H-benzo[d]imidazol-5-amine

The compound was synthesized starting from N-(4-methylthio)benzyl-benzimidazol-5-amine (270 mg; 1 mmol; 1 eq.), benzylbromide (188 mg; 0.131 ml; 1.1 mmol; 1.1 eq.) and K$_2$CO$_3$ (152 mg; 1.1 mmol; 1.1 eq.) according to method 6; Yield: 0.119 g (33.1%); MS m/z: 360.4 [M+H]$^+$; $^1$H-NMR (500 MHz, DMSO d6): δ 2.41 (s, 3H); 4.61 (s, 2H); 4.64 (s, 2H); 6.68 (br s, 1H); 6.72 (dd, 1H, $^4$J=2.4 Hz, $^3$J=8.9 Hz); 7.18-7.22 (m, 5H); 7.26-7.32 (m, 5H); 7.89 (s, 1H); 11.93 (br s, 1H); HPLC (METHOD [A]): rt 16.25 min (94.0%)

Example 52

N-(4-(Methylthio)benzyl)-N-(4-methylbenzyl)-1H-benzo[d]imidazol-5-amine

The compound was synthesized starting from N-(4-methylthio)benzyl-benzimidazol-5-amine (270 mg; 1 mmol; 1 eq.), 4-methyl-benzylbromide (204 mg; 1.1 mmol; 1.1 eq.) and K$_2$CO$_3$ (152 mg; 1.1 mmol; 1.1 eq.) according to method 6; Yield: 0.144 g (38.6%); MS m/z: 374.1 [M+H]$^+$; $^1$H-NMR (500 MHz, DMSO d6): δ 2.24 (s, 3H); 2.41 (s, 3H); 4.58 (s, 4H); 6.67 (br s, 1H); 6.72 (dd, 1H, $^4$J=2.4 Hz, $^3$J=8.9 Hz); 7.92 (d, 2H, $^3$J=8.2 Hz); 7.15 (d, 2H, $^3$J=8.2 Hz); 7.17-7.21 (m, 4H); 7.31 (d, 1H, $^3$J=8.9 Hz); 7.89 (s, 1H); 11.92 (br s, 1H); HPLC (METHOD [A]): rt 17.49 min (99.3%)

Example 53

N-(4-(Methylthio)benzyl)-N-(4-isopropylbenzyl)-1H-benzo[d]imidazol-5-amine

The compound was synthesized starting from N-(4-methylthio)benzyl-benzimidazol-5-amine (270 mg; 1 mmol; 1 eq.), 4-isopropyl-benzylbromide (234 mg; 0.188 ml; 1.1 mmol; 1.1 eq.) and K$_2$CO$_3$ (152 mg; 1.1 mmol; 1.1 eq.) according to method 6; Yield: 0.197 g (49.1%); MS m/z: 402.4 [M+H]$^+$; $^1$H-NMR (400 MHz, DMSO d6): δ 1.16 (d, 6H, $^3$J=7.1 Hz); 2.42 (s, 3H); 2.83 (hept, 1H, $^3$J=7.1 Hz); 4.61 (s, 4H); 6.68 (br s, 1H); 6.73 (dd, 1H, $^4$J=2.5 Hz, $^3$J=8.7 Hz); 7.16-7.22 (m, 8H); 7.32 (d, 1H, $^3$J=8.7 Hz); 7.89 (s, 1H); 11.90 (br s, 1H); HPLC (METHOD [A]): rt 19.29 min (84.2%)

Example 54

N-(4-(Methylthio)benzyl)-N-(4-methoxybenzyl)-1H-benzo[d]imidazol-5-amine

The compound was synthesized starting from N-(4-methylthio)benzyl-benzimidazol-5-amine (270 mg; 1 mmol; 1 eq.), 4-methoxybenzylbromide (221 mg; 0.158 ml; 1.1 mmol; 1.1 eq.) and K$_2$CO$_3$ (152 mg; 1.1 mmol; 1.1 eq.) according to method 6; Yield: 0.144 g (37.0%); MS m/z: 390.2 [M+H]$^+$; $^1$H-NMR (400 MHz, DMSO d6): δ 2.39 (s, 3H); 3.67 (s, 3H); 4.53 (s, 2H); 4.54 (s, 2H); 6.67 (br s, 1H); 6.72 (dd, 1H, $^4$J=2.5 Hz, $^3$J=8.7 Hz); 6.81-6.85 (m, 2H); 7.15-7.20 (m, 6H); 7.30 (d, 1H, $^3$J=8.7 Hz); 7.87 (s, 1H); 11.87 (br s, 1H); HPLC (METHOD [A]): rt 16.97 min (99.8%)

Example 55

N-(3-Methoxybenzyl)-N-(4-(methylthio)benzyl)-1H-benzo[d]imidazol-5-amine

The compound was synthesized starting from N-(4-methylthio)benzyl-benzimidazol-5-amine (270 mg; 1 mmol; 1 eq.), 3-methoxy-benzylbromide (221 mg; 1.1 mmol; 1.1 eq.) and K$_2$CO$_3$ (152 mg; 1.1 mmol; 1.1 eq.) according to method 6; Yield: 0.126 g (32.4%); MS m/z: 390.1 [M+H]$^+$; $^1$H-NMR (500 MHz, DMSO d6): δ 2.41 (s, 3H); 3.67 (s, 3H); 4.61 (s, 4H); 6.68 (br s, 1H); 6.71 (dd, 1H, $^4$J=1.8 Hz, $^3$J=8.9 Hz); 6.76 (dd, 1H, $^4$J=2.4 Hz, $^3$J=8.2 Hz); 6.81 (br s, 1H); 6.84 (d, 1H, $^3$J=7.6 Hz); 7.18-7.22 (m, 5H); 7.32 (d, 1H, $^3$J=8.5 Hz); 7.89 (s, 1H); 11.91 (br s, 1H); HPLC (METHOD [A]): rt 16.52 min (99.1%)

Example 56

N-(3,5-Dimethoxybenzyl)-N-(4-(methylthio)benzyl)-1H-benzo[d]imidazol-5-amine

The compound was synthesized starting from N-(4-methylthio)benzyl-benzimidazol-5-amine (270 mg; 1 mmol; 1 eq.), 3,5-dimethoxybenzylchloride (205 mg; 1.1 mmol; 1.1 eq.) and K$_2$CO$_3$ (152 mg; 1.1 mmol; 1.1 eq.) according to method 6; Yield: 0.019 g (4.5%); MS m/z: 420.5 [M+H]$^+$; $^1$H-NMR (400 MHz, DMSO d6): δ 2.40 (s, 3H); 3.64 (s, 6H); 4.54 (s, 2H); 4.59 (s, 2H); 6.31 (t, 1H, $^4$J=2.1 Hz); 6.40 (d, 2H, $^4$J=2.1 Hz); 6.66 (br s, 1H); 6.69 (dd, 1H, $^4$J=2.1 Hz, $^3$J=8.7 Hz); 7.16-7.21 (m, 4H); 7.30 (d, 1H, $^3$J=8.7 Hz); 7.88 (s, 1H); 11.89 (br s, 1H); HPLC (METHOD [A]): rt 17.28 min (97.1%)

Example 57

N-(2-Fluoro-4,5-dimethoxybenzyl)-N-(4-(methylthio)benzyl)-1H-benzo[d]imidazol-5-amine The compound was synthesized starting from N-(4-methylthio)benzyl-benzimidazol-5-amine (270 mg; 1 mmol; 1 eq.), 2-fluoro-4,5-dimethoxybenzylchloride (225 mg; 1.1 mmol; 1.1 eq.) and K$_2$CO$_3$ (152 mg; 1.1 mmol; 1.1 eq.) according to method 6; Yield: 0.022 g (5.0%); MS m/z: 438.5 [M+H]$^+$; $^1$H-NMR (500 MHz, DMSO d6): δ 2.42 (s, 3H); 3.54 (s, 3H); 3.72 (s, 3H); 4.55 (s, 2H); 4.57 (s, 2H); 6.74-6.76 (m, 1H); 6.80-6.81 (m, 2H); 6.86-6.88 (m, 1H); 7.17-7.21 (m, 4H); 7.36 (br s, 1H); 7.92 (s, 1H); 11.93 (br s, 1H); HPLC (METHOD [A]): rt 16.69 min (95.0%)

Example 58

N-(2-Fluoro-3-methylbenzyl)-N-(4-(methylthio)benzyl)-1H-benzo[d]imidazol-5-amine The compound was synthesized starting from N-(4-methylthio)benzyl-benzimidazol-5-amine (270 mg; 1 mmol; 1 eq.), 2-fluoro-3-methylbenzylbromide (223 mg; 1.1 mmol; 1.1 eq.) and K$_2$CO$_3$ (152 mg; 1.1 mmol; 1.1 eq.) according to method 6; Yield: 0.119 g (30.4%); MS m/z: 392.2 [M+H]$^+$; $^1$H-NMR (500 MHz, DMSO d6): δ 2.22 (s, 3H); 2.41 (s, 3H); 4.62 (s, 2H); 4.67 (s, 2H); 6.68-6.71 (m, 2H); 6.97 (t, 1H, $^3$J=7.6 Hz); 7.01-7.04 (m, 1H); 7.11-7.14 (m, 1H); 7.17-7.22 (m, 4H); 7.32 (d, 1H, $^3$J=8.9 Hz); 7.90 (s, 1H); 11.91 (br s, 1H); HPLC (METHOD [A]): rt 17.77 min (100%)

Example 59

N-(3,5-Difluorobenzyl)-N-(4-(methylthio)benzyl)-1H-benzo[d]imidazol-5-amine

The compound was synthesized starting from N-(4-methylthio)benzyl-benzimidazol-5-amine (270 mg; 1 mmol; 1 eq.), 3,5-difluoro-benzylbromide (228 mg; 0.143 ml; 1.1 mmol; 1.1 eq.) and K$_2$CO$_3$ (152 mg; 1.1 mmol; 1.1 eq.) according to method 6; Yield: 0.149 g (37.7%); MS m/z: 396.2 [M+H]$^+$; $^1$H-NMR (400 MHz, DMSO d6): δ 2.42 (s, 3H); 4.66 (s, 2H); 4.68 (s, 2H); 6.70-6.72 (m, 2H); 6.96-6.99 (m, 2H); 7.05 (tt, 1H, $^4J$=2.1 Hz, $^3J_{H,F}$=9.1 Hz); 7.21 (s, 4H); 7.34 (d, 1H, $^3J$=8.7 Hz); 7.92 (s, 1H); 11.94 (br s, 1H); HPLC (METHOD [A]): rt 17.35 min (99.7%)

Example 60

N-(3,4,5-Trifluorobenzyl)-N-(4-(methylthio)benzyl)-1H-benzo[d]imidazol-5-amine

The compound was synthesized starting from N-(4-methylthio)benzyl-benzimidazol-5-amine (270 mg; 1 mmol; 1 eq.), 3,4,5-trifluorobenzylbromide (248 mg; 1.1 mmol; 1.1 eq.) and K$_2$CO$_3$ (152 mg; 1.1 mmol; 1.1 eq.) according to method 6; Yield: 0.161 g (39.0%); MS m/z: 414.3 [M+H]$^+$; $^1$H-NMR (400 MHz, DMSO d6): δ 2.42 (s, 3H); 4.63 (s, 2H); 4.65 (s, 2H); 6.71-6.73 (m, 2H); 7.17-7.20 (m, 6H); 7.35 (d, 1H, $^3J$=8.5 Hz); 7.92 (s, 1H); 11.93 (br s, 1H); HPLC (METHOD [A]): rt 18.51 min (100%)

Example 61

N-(2,4,5-Trifluorobenzyl)-N-(4-(methylthio)benzyl)-1H-benzo[d]imidazol-5-amine

The compound was synthesized starting from N-(4-methylthio)benzyl-benzimidazol-5-amine (270 mg; 1 mmol; 1 eq.), 2,4,5-trifluorobenzylbromide (248 mg; 1.1 mmol; 1.1 eq.) and K$_2$CO$_3$ (152 mg; 1.1 mmol; 1.1 eq.) according to method 6; Yield: 0.134 g (31.3%); MS m/z: 414.2 [M+H]$^+$; $^1$H-NMR (400 MHz, DMSO d6): δ 2.41 (s, 3H); 4.62 (s, 2H); 4.63 (s, 2H); 6.72-6.74 (m, 2H); 7.17-7.21 (m, 5H); 7.34-7.35 (m, 1H); 7.50-7.56 (m, 1H); 7.92 (s, 1H); 11.94 (br s, 1H); HPLC (METHOD [A]): rt 17.22 min (100%)

Example 62

N-(2,3,5,6-Tetrafluoro-4-methylbenzyl)-N-(4-(methylthio)benzyl)-1H-benzo[d]imidazol-5-amine The compound was synthesized starting from N-(4-methylthio)benzyl-benzimidazol-5-amine (270 mg; 1 mmol; 1 eq.), 2,3,5,6-tetra-fluoro-4-methylbenzylbromide (283 mg; 1.1 mmol; 1.1 eq.) and K$_2$CO$_3$ (152 mg; 1.1 mmol; 1.1 eq.) according to method 6; Yield: 0.094 g (21.1%); MS m/z: 446.4 [M+H]$^+$; $^1$H-NMR (500 MHz, DMSO d6): δ 2.19 (s, 3H); 2.40 (s, 3H); 4.47 (s, 2H); 4.70 (s, 2H); 6.87-6.88 (m, 2H); 7.13-7.15 (m, 2H); 7.18-7.19 (m, 2H); 7.36 (br s, 1H); 7.96 (s, 1H); 12.03 (br s, 1H); HPLC (METHOD [A]): rt 18.71 min (100%)

Example 63

N-(2,5-Dichlorobenzyl)-N-(4-(methylthio)benzyl)-1H-benzo[d]imidazol-5-amine

The compound was synthesized starting from N-(4-methylthio)benzyl-benzimidazol-5-amine (270 mg; 1 mmol; 1 eq.), 2,5-dichlorobenzylbromide (264 mg; 1.1 mmol; 1.1 eq.) and K$_2$CO$_3$ (152 mg; 1.1 mmol; 1.1 eq.) according to method 6; Yield: 0.088 g (20.6%); MS m/z: 428.1/429.3/430.3/431.4 [M+H]$^+$ (Cl-Isotope); $^1$H-NMR (500 MHz, DMSO d6): δ 2.41 (s, 3H); 4.67 (s, 2H); 4.71 (s, 2H); 6.62-6.64 (m, 2H); 7.16 (d, 1H, $^4J$=2.7 Hz); 7.19-7.23 (m, 4H); 7.33-7.36 (m, 2H); 7.51 (d, 1H, $^3J$=8.5 Hz); 7.93 (s, 1H); 11.95 (br s, 1H); HPLC (METHOD [A]): rt 18.35 min (100%)

Example 64

N-(4-(Methylthio)benzyl)-N-(4-bromobenzyl)-1H-benzo[d]imidazol-5-amine

The compound was synthesized starting from N-(4-methylthio)benzyl-benzimidazol-5-amine (270 mg; 1 mmol; 1 eq.), 4-bromobenzylbromide (275 mg; 1.1 mmol; 1.1 eq.) and K$_2$CO$_3$ (152 mg; 1.1 mmol; 1.1 eq.) according to method 6; Yield: 0.251 g (57.3%); MS m/z: 438.3/440.3 [M+H]$^+$; $^1$H-NMR (400 MHz, DMSO d6): δ 2.42 (s, 3H); 4.61 (s, 4H); 6.67 (br s, 1H); 6.72 (dd, 1H, $^4J$=2.5 Hz, $^3J$=8.7 Hz); 7.20-7.21 (m, 4H); 7.22-7.24 (m, 2H); 7.33 (d, 1H, $^3J$=8.7 Hz); 7.48-7.50 (m, 2H); 7.91 (s, 1H); 11.93 (br s, 1H); HPLC (METHOD [A]): rt 18.13 min (99.5%)

Example 65

N-(4-(Methylthio)benzyl)-N-((5-chlorobenzo[b]thiophen-3-yl)methyl)-1H-benzo[d]imidazol-5-amine The compound was synthesized starting from N-(4-methylthio)benzyl-benzimidazol-5-amine (270 mg; 1 mmol; 1 eq.), (5-chlorobenzo[b]thiophen-3-yl)methylbromide (288 mg; 1.1 mmol; 1.1 eq.) and K$_2$CO$_3$ (152 mg; 1.1 mmol; 1.1 eq.) according to method 6; Yield: 0.173 g (38.4%); MS m/z: 450.3/452.3[M+H]$^+$; $^1$H-NMR (400 MHz, DMSO d6): δ 2.42 (s, 3H, 4.62 (s, 2H); 4.84 (s, 2H); 6.79-6.83 (m, 2H); 7.17-7.25 (m, 4H); 7.35 (d, 1H, $^3J$=8.7 Hz); 7.39 (dd, 1H, $^4J$=2.1 Hz, $^3J$=8.7 Hz); 7.47 (s, 1H); 7.91-7.92 (m, 2H); 8.00 (d, 1H, $^3J$=8.7 Hz); 11.93 (br s, 1H); HPLC (METHOD [A]): rt 19.46 min (99.6%)

Example 66

N-(4-(Methylthio)benzyl)-N-((benzo[d]thiazol-2-yl)methyl)-1H-benzo[d]imidazol-5-amine The compound was synthesized starting from N-(4-methylthio)benzyl-benzimidazol-5-amine (270 mg; 1 mmol; 1 eq.), (benzo[d]-thiazol-2-yl)methylbromide (251 mg; 1.1 mmol; 1.1 eq.) and K$_2$CO$_3$ (152 mg; 1.1 mmol; 1.1 eq.) according to method 6; Yield: 0.155 g (37.3%); MS m/z: 417.2 [M+H]$^+$; $^1$H-NMR (500 MHz, DMSO d6): δ 2.43 (s, 3H); 4.73 (s, 2H); 5.03 (s, 2H); 6.85-6.87 (m, 2H); 7.21-7.23 (m, 2H); 7.29-7.31 (m, 2H); 7.36-7.39 (m, 2H); 7.46-7.49 (m, 1H); 7.94-7.95 (m, 2H); 12.07 (br s, 1H); HPLC (METHOD [A]): rt 15.74 min (98.5%)

Example 67

N-(4-(Methylthio)benzyl)-N-((benzo[c][1,2,5]thiadiazol-6-yl)methyl)-1H-benzo[d]imidazol-5-amine The compound was synthesized starting from N-(4-methylthio)benzyl-benzimidazol-5-amine (270 mg; 1 mmol; 1 eq.), benzo[c]-[1,2,5]thiadiazol-6-yl)methylbromide (252 mg; 1.1 mmol; 1.1 eq.) and K$_2$CO$_3$ (152 mg; 1.1 mmol; 1.1 eq.) according to method 6; Yield: 0.181 g (43.4%); MS m/z: 418.5 [M+H]$^+$; $^1$H-NMR (400 MHz, DMSO d6): δ 2.43 (s, 3H); 4.73 (s, 2H); 4.86 (s, 2H); 6.78-6.80 (m, 2H); 7.20-7.27 (m, 4H); 7.34 (d, 1H, $^3J$=8.7 Hz); 7.68 (d, 1H, $^4J$=1.7 Hz, $^3J$=9.1 Hz); 7.86 (s, 1H); 7.90 (s, 1H); 8.05 (d, 1H, $^3J$=9.1 Hz) 11.91 (br s, 1H); HPLC (METHOD [A]): rt 15.54 min (100%)

Example 68

N-(4-Ethylbenzyl)-N-(4-methylbenzyl)-1H-benzo[d]imidazol-5-amine

The compound was synthesized starting from N-(4-ethylbenzyl)benzimidazol-5-amine (251 mg; 1 mmol; 1 eq.), 4-methylbenzylbromide (204 mg; 1.1 mmol; 1.1 eq.) and $K_2CO_3$ (152 mg; 1.1 mmol; 1.1 eq.) according to method 6; Yield: 0.131 g (36.9%); MS m/z: 356.5 [M+H]$^+$; $^1$H-NMR (500 MHz, DMSO d6): δ 1.14 (t, 3H, $^3$J=7.6 Hz); 2.25 (s, 3H); 2.55 (q, 2H, $^3$J=7.6 Hz); 4.60 (s, 4H); 6.68 (br s, 1H); 6.72 (dd, 1H, $^4$J=1.8 Hz, $^3$J=8.9 Hz); 7.09-7.19 (m, 8H); 7.32 (d, 1H, $^3$J=8.9 Hz); 7.89 (s, 1H); 11.88 (br s, 1H); HPLC (METHOD [A]): rt 18.62 min (100%)

Example 69

N-(4-(Methylthio)benzyl)-N-(4-ethylbenzyl)-1H-benzo[d]imidazol-5-amine

The compound was synthesized starting from N-(4-ethylbenzyl)benzimidazol-5-amine (251 mg; 1 mmol; 1 eq.), 4-methylthiobenzylbromide (239 mg; 1.1 mmol; 1.1 eq.) and $K_2CO_3$ (152 mg; 1.1 mmol; 1.1 eq.) according to method 6; Yield: 0.166 g (42.9%); MS m/z: 388.4 [M+H]$^+$; $^1$H-NMR (500 MHz, DMSO d6): δ 1.14 (t, 3H, $^3$J=7.6 Hz); 2.42 (s, 3H); 2.55 (q, 2H, $^3$J=7.7 Hz); 4.60 (s, 4H); 6.69 (br s, 1H); 6.73 (dd, 1H, $^4$J=1.8 Hz, $^3$J=8.9 Hz); 7.12-7.23 (m, 8H); 7.32 (d, 1H, $^3$J=8.9 Hz); 7.89 (s, 1H); 11.89 (br s, 1H); HPLC (METHOD [A]): rt 19.04 min (92.3%)

Example 70

N-(2,3,5,6-Tetrafluoro-4-methylbenzyl)-N-(4-ethylbenzyl)-1H-benzo[d]imidazol-5-amine The compound was synthesized starting from N-(4-ethylbenzyl)benzimidazol-5-amine (251 mg; 1 mmol; 1 eq.), 2,3,5,6-tetrafluoro-4-methylbenzylbromide (283 mg; 1.1 mmol; 1.1 eq.) and $K_2CO_3$ (152 mg; 1.1 mmol; 1.1 eq.) according to method 6; Yield: 0.051 g (11.9%); MS m/z: 428.4 [M+H]$^+$; $^1$H-NMR (500 MHz, DMSO d6): δ 1.11 (t, 3H, $^3$J=7.6 Hz); 2.18 (s, 3H); 2.50-2.54 (m, 2H); 4.47 (s, 2H); 4.70 (s, 2H); 6.87-6.91 (m, 2H); 7.07 (d, 2H, $^3$J=7.9 Hz); 7.14 (d, 2H, $^3$J=7.9 Hz); 7.37 (d, 1H, $^3$J=8.9 Hz), 7.96 (s, 1H); 12.05 (br s, 1H); HPLC (METHOD [A]): rt 19.03 min (93.3%)

Example 71

N-(3,4,5-Trifluorobenzyl)-N-(4-ethylbenzyl)-1H-benzo[d]imidazol-5-amine

The compound was synthesized starting from N-(4-ethylbenzyl)benzimidazol-5-amine (251 mg; 1 mmol; 1 eq.), 3,4,5-trifluorobenzylbromide (248 mg; 1.1 mmol; 1.1 eq.) and $K_2CO_3$ (152 mg; 1.1 mmol; 1.1 eq.) according to method 6; Yield: 0.078 g (19.7%); MS m/z: 396.2 [M+H]$^+$; $^1$H-NMR (500 MHz, DMSO d6): δ 1.14 (t, 3H, $^3$J=7.6 Hz); 2.55 (q, 2H, $^3$J=7.6 Hz); 4.64 (s, 2H); 4.66 (s, 2H); 6.71-6.74 (m, 2H); 7.13-7.20 (m, 6H); 7.35 (d, 1H, $^3$J=8.2 Hz); 7.94 (s, 1H); 12.03 (br s, 1H); HPLC (METHOD [A]): rt 18.63 min (92.1%)

Example 72

N-(4-Cyanobenzyl)-N-(4-ethylbenzyl)-1H-benzo[d]imidazol-5-amine

The compound was synthesized starting from N-(4-ethylbenzyl)benzimidazol-5-amine (251 mg; 1 mmol; 1 eq.), 4-cyanobenzylbromide (216 mg; 1.1 mmol; 1.1 eq.) and $K_2CO_3$ (152 mg; 1.1 mmol; 1.1 eq.) according to method 6; Yield: 0.127 g (34.7%); MS m/z: 367.2 [M+H]$^+$; $^1$H-NMR (500 MHz, DMSO d6): (Rotamers) δ 1.14 (t, 3H, $^3$J=7.6 Hz); 2.55 (q, 2H, $^3$J=7.6 Hz); 4.63 (s, 0.7H); 4.66 (s, 1.3H); 4.72 (s, 0.7H); 4.76 (s, 1.3H); 6.61 (br s, 0.7H); 6.67-6.68 (m, 0.7H); 6.75-6.77 (m, 0.3H); 6.81 (br s, 0.3H); 7.14 (d, 2H, $^3$J=7.9 Hz); 7.19 (d, 2H, $^3$J=7.9 Hz); 7.25-7.27 (m, 0.3H); 7.36 (d, 0.7H, $^3$J=8.9 Hz); 7.46 (d, 2H, $^3$J=8.2 Hz); 7.77 (d, 2H, 3J=8.2 Hz); 7.87 (s, 0.7H); 7.97 (s, 0.3H); 11.85 (s, 0.7H); 12.04 (s, 0.3H); HPLC (METHOD [A]): rt 17.49 min (98.4%)

Example 73

N-(4-Ethylbenzyl)-N-((5-chlorobenzo[b]thiophen-3-yl)methyl)-1H-benzo[d]imidazol-5-amine The compound was synthesized starting from N-(4-ethylbenzyl)benzimidazol-5-amine (251 mg; 1 mmol; 1 eq.), (5-chlorobenzo[b]-thiophen-3-yl)methylbromide (288 mg; 1.1 mmol; 1.1 eq.) and $K_2CO_3$ (152 mg; 1.1 mmol; 1.1 eq.) according to method 6; Yield: 0.125 g (29.0%); MS m/z: 432.6 [M+H]$^+$; $^1$H-NMR (500 MHz, DMSO d6): δ 1.14 (t, 3H, $^3$J=7.6 Hz); 2.55 (q, 2H, $^3$J=7.6 Hz); 4.64 (s, 2H); 4.85 (s, 2H); 6.79 (d, 1H, $^4$J=2.1 Hz); 6.84 (dd, 1H, $^4$J=2.1 Hz, $^3$J=8.9 Hz); 7.12-7.14 (m, 2H); 7.20-7.21 (m, 2H); 7.37 (d, 1H, $^3$J=8.9 Hz); 7.40 (dd, 1H, $^4$J=1.8 Hz, $^3$J=8.5 Hz); 7.47 (s, 1H); 7.93 (d, 1H, $^4$J=1.8 Hz); 7.94 (s, 1H); 8.00 (d, 1H, $^3$J=8.5 Hz); 12.18 (br s, 1H); HPLC (METHOD [A]): rt 19.69 min (100%)

Example 74

N-(4-Ethylbenzyl)-N-((benzo[d]thiazol-2-yl)methyl)-1H-benzo[d]imidazol-5-amine The compound was synthesized starting from N-(4-ethylbenzyl)benzimidazol-5-amine (251 mg; 1 mmol; 1 eq.), (benzo[d]-thiazol-2-yl)methylbromide (251 mg; 1.1 mmol; 1.1 eq.) and $K_2CO_3$ (152 mg; 1.1 mmol; 1.1 eq.) according to method 6; Yield: 0.118 g (29.6%);; MS m/z: 399.4 [M+H]$^+$; $^1$H-NMR (500 MHz, DMSO d6): δ 1.14 (t, 3H, $^3$J=7.6 Hz); 2.56 (q, 2H, $^3$J=7.6 Hz); 4.74 (s, 2H); 5.02 (s, 2H); 6.85-6.86 (m, 2H); 7.15-7.17 (m, 2H); 7.26-7.27 (m, 2H); 7.36-7.39 (m, 2H); 7.46-7.49 (m, 1H); 7.94-7.95 (m, 2H); 7.98-8.00 (m, 1H); 11.98 (br s, 1H); HPLC (METHOD [A]): rt 17.02 min (97.8%)

Example 75

N-(4-Ethylbenzyl)-N-((benzo[c][1,2,5]thiadiazol-6-yl)methyl)-1H-benzo[d]imidazol-5-amine The compound was synthesized starting from N-(4-ethylbenzyl)benzimidazol-5-amine (251 mg; 1 mmol; 1 eq.), (benzo-[c][1,2,5]-thiadiazol-6-yl)methylbromide (252 mg; 1.1 mmol; 1.1 eq.) and $K_2CO_3$ (152 mg; 1.1 mmol; 1.1 eq.) according to method 6; Yield: 0.115 g (28.8%); MS m/z: 400.2 [M+H]$^+$; $^1$H-NMR (500 MHz, DMSO d6): δ 1.14 (t, 3H, $^3$J=7.6 Hz); 2.55 (q, 2H, $^3$J=7.6 Hz); 4.73 (s, 2H); 4.87 (s, 2H); 6.77-6.81 (m, 2H); 7.15 (d, 2H, $^3$J=7.9 Hz); 7.22 (d, 2H, ³J=7.9 Hz), 7.34 (d, 1H, ³J=8.5 Hz); 7.69 (dd, 1H, ⁴J=1.5 Hz, ³J=9.2 Hz); 7.85 (s, 1H); 7.90 (s, 1H); 8.05 (d, 1H, ³J=8.9 Hz), 11.93 (br s, 1H); HPLC (METHOD [A]): rt 17.72 min (96.4%)

Example 76

N-(4-Methoxybenzyl)-N-(benzo[c][1,2,5]thiadiazol-6-yl)methyl)-1H-benzo[d]imidazol-5-amine The compound was synthesized starting from N-(4-methoxybenzyl)benzimidazol-5-amine (253 mg; 1 mmol; 1 eq.), (benzo-[c][1,2,5]thiadiazol-6-yl)methylbromide (252 mg; 1.1 mmol; 1.1 eq.) and $K_2CO_3$ (152 mg; 1.1 mmol; 1.1 eq.) according to method 6; Yield: 0.173 g (43.1%); MS m/z: 402.3 [M+H]⁺; ¹H-NMR (500 MHz, DMSO d6): δ 3.70 (s, 3H); 4.70 (s, 2H); 4.85 (s, 2H); 6.71 (br s, 1H); 6.78-6.80 (m, 1H); 6.87-6.88 (m, 2H); 7.22-7.24 (m, 2H); 7.37-7.39 (m, 1H); 7.67-7.69 (m, 1H); 7.85 (s, 1H); 7.87 (s, 1H); 8.04-8.05 (m, 1H); 11.85 (br s, 1H); HPLC (METHOD [A]): rt 14.79 min (89.2%)

Example 77

N-(4-Chlorobenzyl)-N-((benzo[c][1,2,5]thiadiazol-6-yl)methyl)-1H-benzo[d]imidazol-5-amine The compound was synthesized starting from N-(4-chlorobenzyl)benzimidazol-5-amine (258 mg; 1 mmol; 1 eq.), (benzo-[c][1,2,5]-thiadiazol-6-yl)methylbromide (252 mg; 1.1 mmol; 1.1 eq.) and $K_2CO_3$ (152 mg; 1.1 mmol; 1.1 eq.) according to method 6; Yield: 0.151 g (37.2%); MS m/z: 406.4/408.3 [M+H]⁺; ¹H-NMR (500 MHz, DMSO d6): δ 4.77 (s, 2H); 4.88 (s, 2H); 6.73-6.79 (m, 2H); 7.32-7.38 (m, 5H); 7.69 (dd, 1H, ⁴J=1.5 Hz, ³J=9.2 Hz); 7.86 (s, 1H); 7.92 (s, 1H); 8.05 (d, 1H, ³J=9.2 Hz); 11.87 (br s, 1H); HPLC (METHOD [A]): rt 15.88 min (95.9%)

Example 78

N-(4-(Dimethylamino)benzyl)-N-(4-methylbenzyl)-1H-benzo[d]imidazol-5-amine

The compound was synthesized starting from N-(4-dimethylamino)benzyl-benzimidazol-5-amine (266 mg; 1 mmol; 1 eq.), 4-methylbenzylbromide (204 mg; 1.1 mmol; 1.1 eq.) and $K_2CO_3$ (152 mg; 1.1 mmol; 1.1 eq.) according to method 6; Yield: 0.112 g (30.3%); MS m/z: 250.2 [M-$C_9H_{12}N$.]⁺; ¹H-NMR (500 MHz, DMSO d6): δ 2.24 (s, 3H); 2.83 (s, 6H); 4.50 (s, 2H); 4.54 (s, 2H); 6.64-6.67 (m, 2H); 6.70 (d, 1H, ⁴J=2.4 Hz); 6.76 (dd, 1H, ⁴J=2.4 Hz, ³J=8.9 Hz); 7.07-7.10 (m, 4H); 7.14-7.16 (m, 2H); 7.32 (d, 1H, ³J=8.9 Hz); 7.91 (s, 1H); 11.98 (br s, 1H); HPLC (METHOD [A]): rt 11.13 min (96.2%)

Example 79

N-(4-(Dimethylamino)benzyl)-N-(4-methoxybenzyl)-1H-benzo[d]imidazol-5-amine

The compound was synthesized starting from N-(4-dimethylamino)benzyl-benzimidazol-5-amine (266 mg; 1 mmol; 1 eq.), 4-methoxybenzylbromide (221 mg; 0.158 ml; 1.1 mmol; 1.1 eq.) and $K_2CO_3$ (152 mg; 1.1 mmol; 1.1 eq.) according to method 6; Yield: 0.120 g (31.1%); MS m/z: 254.4 [M-$C_9H_{12}N$.]⁺; 166.3; ¹H-NMR (500 MHz, DMSO d6): δ 2.83 (s, 6H); 3.70 (s, 3H); 4.48 (s, 2H); 4.51 (s, 2H); 6.65-6.67 (m, 2H); 6.71 (br s, 1H); 6.77 (dd, 1H, ⁴J=2.3 Hz, ³J=8.9 Hz); 6.84-6.87 (m, 2H); 7.07-7.09 (m, 2H); 7.16-7.18 (m, 2H); 7.32 (d, 1H, ³J=8.9 Hz); 7.90 (s, 1H); 11.92 (br s, 1H); HPLC (METHOD [A]): rt 10.13 min (87.3%)

Example 80

N-(4-(Dimethylamino)benzyl)-N-(4-(methylthio)benzyl)-1H-benzo[d]imidazol-5-amine The compound was synthesized starting from N-(4-dimethylamino)benzyl-benzimidazol-5-amine (266 mg; 1 mmol; 1 eq.), 4-methylthiobenzylbromide (239 mg; 1.1 mmol; 1.1 eq.) and $K_2CO_3$ (152 mg; 1.1 mmol; 1.1 eq.) according to method 6; Yield: 0.087 g (21.6%); MS m/z: 166.3; ¹H-NMR (500 MHz, DMSO d6): δ 2.83 (s, 6H); 2.41 (s, 3H); 4.48 (s, 2H); 4.51 (s, 2H); 6.65-6.67 (m, 2H); 6.71 (br s, 1H); 6.77 (dd, 1H, ⁴J=2.3 Hz, ³J=8.9 Hz); 6.84-6.87 (m, 2H); 7.07-7.09 (m, 2H); 7.16-7.18 (m, 2H); 7.32 (d, 1H, ³J=8.9 Hz); 7.90 (s, 1H); 11.92 (br s, 1H); HPLC (METHOD [A]): rt 11.65 min (92.4%)

Example 81

N-(4-(Dimethylamino)benzyl)-N-((benzo[c][1,2,5]thiadiazol-5-yl)methyl)-1H-benzo[d]imidazol-5-amine The compound was synthesized starting from N-(4-dimethylamino)benzyl-benzimidazol-5-amine (266 mg; 1 mmol; 1 eq.), (benzo[c][1,2,5]thiadiazol-5-yl)methyl)bromide (252 mg; 1.1 mmol; 1.1 eq.) and $K_2CO_3$ (152 mg; 1.1 mmol; 1.1 eq.) according to method 6; Yield: 0.167 g (40.3%); MS m/z: 282.4 [M-$C_9H_{12}N$.]⁺; ¹H-NMR (500 MHz, DMSO d6): δ 2.83 (s, 6H); 4.62 (s, 2H); 4.80 (s, 2H); 6.66-6.68 (m, 2H); 6.79 (br s, 1H); 6.83 (dd, 1H; ⁴J=2.1 Hz, ³J=8.9 Hz); 7.12-7.14 (m, 2H); 7.34 (d, 1H, ³J=8.8 Hz); 7.68 (dd, 1H, ⁴J=1.6 Hz, ³J=9.0 Hz); 7.84 (s, 1H); 7.90 (s, 1H); 8.04 (d, 1H, ³J=9.0 Hz), 11.91 (br s, 1H); HPLC (METHOD [A]): rt 11.59 min (94.1%)

Example 82

N-(4-(Methylthio)benzyl)-N-(cyclohexylmethyl)-1H-benzo[d]imidazol-5-amine

The compound was synthesized starting from N-cyclohexylmethyl-benzimidazol-5-amine (115 mg; 0.5 mmol; 1 eq.), 4-methylthiobenzylbromide (120 mg; 0.55 mmol; 1.1 eq.) and $K_2CO_3$ (76 mg; 0.55 mmol; 1.1 eq.) according to method 6; Yield: 0.068 g (37.3%); MS m/z: 366.4 [M+H]⁺; ¹H-NMR (400 MHz, DMSO d6): δ 0.90-1.00 (m, 2H); 1.13-1.23 (m, 3H); 1.61-1.76 (m, 6H); 2.41 (s, 3H); 3.24 (d, 2H, ³J=6.6 Hz); 4.52 (s, 2H); 6.67-6.69 (m, 2H); 7.12-7.18 (m, 4H); 7.32-7.34 (m, 1H); 7.89 (s, 1H); 11.84 (br s, 1H); HPLC (METHOD [A]): rt 18.51 min (97.8%)

Example 83

N-(4-(Methylthio)benzyl)-N-butyl-1H-benzo[d]imidazol-5-amine

The compound was synthesized starting from N-butyl-benzimidazol-5)₆)-amine (95 mg 0.5 mmol; 1 eq.), 4-methylthiobenzylbromide (120 mg; 0.55 mmol; 1.1 eq.) and $K_2CO_3$ (76 mg; 0.55 mmol; 1.1 eq.) according to method 6; Yield: 0.073 g (44.9%) MS m/z: 326.4 [M+H]⁺; ¹H-NMR (400 MHz, DMSO d6): δ 0.89 (t, 3H, $^3J$=7.5 Hz); 1.32 (sext, 2H, $^3J$=7.5 Hz); 1.52-1.60 (m, 2H); 2.42 (s, 3H); 3.37 (t, 2H, $^3J$=7.5 Hz); 4.47 (s, 2H); 6.68-6.71 (m, 2H); 7.15-7.20 (m, 4H); 7.34 (d, 1H, $^3J$=8.7 Hz); 7.90 (s, 1H); 11.90 (br s, 1H); HPLC (METHOD [A]): rt 16.31 min (99.7%)

Example 84

N-(4-(Methylthio)benzyl)-N-isobutyl-1H-benzo[d]imidazol-5-amine

The compound was synthesized starting from N-isobutyl-benzimidazol-5-amine (95 mg; 0.5 mmol; 1 eq.), 4-methylthiobenzylbromide (120 mg; 0.55 mmol; 1.1 eq.) and $K_2CO_3$ (76 mg; 0.55 mmol; 1.1 eq.) according to method 6; Yield: 0.066 g (40.6%); MS m/z: 326.4 [M+H]$^+$; $^1$H-NMR (400 MHz, DMSO d6): δ 0.92 (d, 6H, $^3J$=6.6 Hz); 2.01-2.08 (m, 1H); 2.41 (s, 3H); 3.21 (d, 2H, $^3J$=7.1 Hz); 4.53 (s, 2H); 6.68 (br s, 1H); 6.70 (dd, 1H, $^3J$=2.1 Hz, $^3J$=8.7 Hz); 7.13-7.18 (m, 4H); 7.34 (d, 1H, $^3J$=8.7 Hz); 7.90 (s, 1H); 11.91 (br s, 1H); HPLC (METHOD [A]): rt 16.40 min (99.5%)

Example 85

N-(4-(Methylthio)benzyl)-N-(pentan-2-yl)-1H-benzo[d]imidazol-5-amine

The compound was synthesized starting from N-(pentan-2-yl)benzimidazol-5-amine (102 mg; 0.5 mmol; 1 eq.), 4-methylthiobenzylbromide (120 mg; 0.55 mmol; 1.1 eq.) and $K_2CO_3$ (76 mg; 0.55 mmol; 1.1 eq.) according to method 6; Yield: 0.038 g (22.4%); MS m/z: 340.3 [M+H]$^+$; $^1$H-NMR (400 MHz, DMSO d6): δ 0.85-0.89 (m, 3H); 1.12 (d, 3H, $^3J$=6.6 Hz); 1.33-1.47 (m, 3H); 1.61-1.68 (m, 1H); 2.40 (s, 3H); 3.92-3.94 (m, 1H, $CH_3$—N—CH—$C_3H_7$); 4.30 (s, 2H); 6.77-6.79 (m, 2H); 7.13-7.15 (m, 2H); 7.23-7.25 (m, 2H); 7.31-7.33 (m, 1H); 7.90 (s, 1H); 11.90 (br s, 1H); HPLC (METHOD [A]): rt 16.75 min (85.6%)

Example 86

N-(4-Methoxybenzyl)-N-benzyl-3H-benzo[d]imidazol-5-amine $N_1$-Boc-N-(4-methoxybenzyl)benzimidazol-5-amine (353 mg; 1 mmol; 1 eq.) was dissolved in DMF (5 ml), treated with $K_2CO_3$ (166 mg; 1.2 mmol; 1.2 eq.) and benzylbromide (0.143 ml; 1.2 mmol; 1.2 eq.) and stirred at room temperature for 24 h. The mixture was diluted with water and extracted with ethyl acetate (3×25 ml). The combined organic layers were dried over $Na_2SO_4$ and evaporated. The remains were taken up with THF (5 ml), treated with 5 N $NaOCH_3$ and stirred for 2 h at room temperature. The mixture was diluted with water and extracted with ethyl acetate (3×25 ml). The combined organic layers were dried over $Na_2SO_4$ and evaporated. The residue was purified by flash chromatography on silica using a $CHCl_3$/MeOH gradient. Yield: 0.049 g (14.3%); MS m/z: 344.1 [M+H]$^+$; $^1$H-NMR (500 MHz, DMSO d6): δ 3.70 (s, 3H); 4.60 (s, 2H), 4.64 (s, 2H); 6.71 (d, 1H, $^4J$=2.1 Hz); 6.77 (dd, 1H, $^4J$=2.1 Hz, $^3J$=8.9 Hz); 6.85-6.88 (m, 2H); 7.19-7.22 (m, 3H); 7.26-7.32 (m, 4H); 7.34 (d, 1H, $^3J$=8.9 Hz); 7.99 (s, 1H); HPLC (METHOD [A]): rt 15.26 min (99.8%)

Example 87

N-(4-Methoxybenzyl)-N-((naphthalen-2-yl)methyl)-3H-benzo[d]imidazol-5-amine $N_1$-Boc-N-(4-methoxybenzyl)benzimidazol-5-amine (353 mg; 1 mmol; 1 eq.) was dissolved in DMF (5 ml), treated with $K_2CO_3$ (166 mg; 1.2 mmol; 1.2 eq.) and naphthalen-2-yl-methyl-bromide (265 mg; 1.2 mmol; 1.2 eq.) and stirred at room temperature for 24 h. The mixture was diluted with water and extracted with ethyl acetate (3×25 ml). The combined organic layers were dried over $Na_2SO_4$ and evaporated. The remains were taken up with THF (5 ml), treated with 5 N $NaOCH_3$ and stirred for 2 h at room temperature. The mixture was diluted with water and extracted with ethyl acetate (3×25 ml). The combined organic layers were dried over $Na_2SO_4$ and evaporated. The residue was purified by flash chromatography on silica using a $CHCl_3$/MeOH gradient. Yield: 0.058 mg (14.8%); MS m/z: 394.2 [M+H]$^+$; $^1$H-NMR (500 MHz, DMSO d6): δ 3.70 (s, 3H); 4.68 (s, 2H); 4.80 (s, 2H); 6.76 (d, 1H, $^4J$=2.1 Hz); 6.82 (dd, 1H, $^4J$=2.3 Hz, $^3J$=8.9 Hz); 6.87-6.89 (m, 2H); 7.22-7.24 (m, 2H); 7.34 (d, 1H, $^3J$=8.9 Hz); 7.43-7.47 (m, 5H); 7.75 (br s, 1H); 7.79-7.81 (m, 1H); 7.85-7.87 (m 2H); 7.94 (s, 1H); HPLC (METHOD [A]): rt 18.12 min (95.6%)

Example 88

N-(4-Methoxybenzyl)-N-phenethyl-1H-benzo[d]imidazol-5-amine $N_1$-Trityl-N-(4-methoxyphenyl)benzimidazol-5-amine (990 mg; 2 mmol; 1 eq.) was dissolved in THF (5 ml), cooled to 0° C. and treated with lithiumbis(trimethylsilyl)amide 1M in THF (2.4 ml; 2.4 mmol; 1.2 eq.). Phenylethylbromide (0.330 ml; 2.4 mmol; 2.4 eq.) was added and the mixture was stirred at room temperature for 24 h. The mixture was diluted with water and extracted with ethyl acetate (3×25 ml). The combined organic layers were dried over $Na_2SO_4$ and evaporated. The residue was dissolved in MeOH (5 ml) and treated with TFA (1 ml). After heating to reflux for 1 h the mixture was poured into saturated $NaHCO_3$-solution and extracted with ethyl acetate (3×25 ml). The combined organic layers were dried over $Na_2SO_4$ and evaporated. The residue was purified by flash chromatography on silica using a $CHCl_3$/MeOH gradient. Yield: 0.058 g (8.1%); MS m/z: 358.1 [M+H]$^+$; $^1$H-NMR (500 MHz, DMSO d6): δ 2.85 (t, 2H, $^3J$=7.9 Hz); 3.57 (t, 2H, $^3J$=7.9 Hz); 3.69 (s, 3H); 4.44 (s, 2H); 6.77-6.79 (m, 2H); 6.83-6.86 (m, 2H); 7.14-7.16 (m, 2H); 7.18-7.21 (m, 1H); 7.23-7.25 (m, 2H); 7.28-7.30 (m, 2H); 7.38-7.39 (m, 1H); 7.92 (s, 1H); 11.92 (br s, 1H); HPLC (METHOD [A]): rt 16.74 min (96.3%)

Example 89

N-(4-Methoxybenzyl)-N-(3-phenylpropyl)-3H-benzo[d]imidazol-5-amine $N_1$-Boc-N-(4-Methoxybenzyl)benzimidazol-5-amine (353 mg; 1 mmol; 1 eq.) was dissolved in DMF (5 ml), treated with $K_2CO_3$ (166 mg; 1.2 mmol; 1.2 eq.) and phenylpropyl-bromide (0.183 ml; 1.2 mmol; 1.2 eq.) and stirred at room temperature for 24 h. The mixture was diluted with water and extracted with ethyl acetate (3×25 ml). The combined organic layers were dried over $Na_2SO_4$ and evaporated. The remains were taken up with THF (5 ml), treated with 5 N $NaOCH_3$ and stirred for 2 h at room temperature. The mixture was diluted with water and extracted with ethyl acetate (3×25 ml). The combined organic layers were dried over $Na_2SO_4$ and evaporated. The residue was purified by flash chromatography on silica using a $CHCl_3$/MeOH gradient. Yield: 0.015 g (4.0%); MS m/z: 372.1 [M+H]$^+$; $^1$H-NMR (500 MHz, DMSO d6): δ 1.84-1.90 (m, 2H); 2.62 (t, 2H, $^3$J=7.6 Hz); 3.39 (t, 2H, $^3$J=7.6 Hz); 3.39 (s, 3H); 4.45 (s, 2H); 6.71 (br s, 1H); 6.73 (dd, 1H, $^4$J=2.1 Hz, $^3$J=8.9 Hz); 6.83-6.85 (m, 2H); 7.12-7.14 (m, 2H); 7.16-7.19 (m, 3H); 7.24-7.27 (m, 2H); 7.36 (d, 1H, $^3$J=8.9 Hz); 8.08 (s, 1H); HPLC (METHOD [A]): rt 16.97 min (93.2%)

Example 90

N-Benzyl-N-phenyl-1H-benzo[d]imidazol-5-amine $N_1$-Trityl-N-phenyl-benzimidazol-5-amine (1.13 g; 2.5 mmol; 1 eq.) was dissolved in THF (5 ml), cooled to 0° C. and treated with lithiumbis(trimethylsilyl)amide 1M in THF (3 ml; 3 mmol; 1.2 eq.). Benzylbromide (3 mmol; 1.2 eq.) was added and stirred at room temperature for 24 h. The mixture was diluted with water and extracted with ethyl acetate (3×25 ml). The combined organic layers were dried over $Na_2SO_4$ and evaporated. The residue was dissolved in MeOH (5 ml) and treated with TFA (1 ml). After heating to reflux overnight the mixture was poured into saturated $NaHCO_3$-solution and extracted with ethyl acetate (3×25 ml). The combined organic layers were dried over $Na_2SO_4$ and evaporated. The residue was purified by flash chromatography on silica using a $CHCl_3$/MeOH gradient. Yield: 0.046 g (6.2%); MS m/z: 300.1 [M+H]$^+$; $^1$H-NMR, 500 MHz, $^1$H-NMR (500 MHz, DMSO d6): δ 5.00 (s, 2H); 6.70-6.73 (m, 1H); 6.78-6.79 (m, 2H); 7.06-7.08 (m, 1H); 7.10-7.13 (m, 2H); 7.18-7.21 (m, 1H); 7.29-7.31 (m, 2H); 7.36-7.37 (m, 3H); 7.54 (d, 1H, $^3$J=8.5 Hz); 8.30 (s, 1H); 12.32 (br s, 1H); HPLC (METHOD [A]): rt 15.47 min (95.1%)

Example 91

N-((1H-Benzo[d]imidazol-5-yl)methyl)benzenamine

The compound was synthesized starting from benzimidazol-5-carbaldehyde (146 mg; 1 mmol; 1 eq.), aniline (0.095 ml; 1 mmol; 1 eq.), NaBH(AcO)$_3$ (318 mg; 1.5 mmol; 1.5 eq.) and AcOH (0.095 ml; 1.5 mmol; 1.5 eq.) as described above. Yield: 0.160 g (71%); MS m/z: 224.3 [M+H]$^+$; $^1$H-NMR (400 MHz, DMSO d6): δ 4.34-4.35 (m, 2H); 6.20.6.21 (m, 1H); 6.45-6.49 (m, 1H); 6.57-6.59 (m, 1H); 6.98-7.02 (m, 1H); 7.17-7.26 (m, 2H); 7.39-7.43 (m, 1H); 7.49-7.52 (m, 2H); 12.34-12.39 (br m, 1H); HPLC (METHOD [A]): rt 8.16 min (97.3%)

Example 92

N-((1H-Benzo[d]imidazol-5-yl)methyl)-2-phenylethanamine

The compound was synthesized starting from benzimidazol-5-carbaldehyde (146 mg; 1 mmol; 1 eq.), phenylethylamine (0.126 ml; 1 mmol; 1 eq.); NaBH(AcO)$_3$ (318 mg; 1.5 mmol; 1.5 eq.) and AcOH (0.095 ml; 1.5 mmol; 1.5 eq.) as described above. Yield: 0.040 g (16%); MS m/z: 252.2 [M+H]$^+$; $^1$H-NMR (400 MHz, DMSO d6): δ 3.30 (br s, 4H); 3.81 (s, 2H); 7.12-7.27 (m, 9H); 8.13-8.14 (m, 1H); 12.30 (br s, 1H); HPLC (METHOD [A]): rt doublepeak 6.77/6.60 min (93.7%)

Example 93

N-((1H-Benzo[d]imidazol-5-yl)methyl)(4-methoxyphenyl)-N-methylmethanamine

The compound was synthesized starting from benzimidazol-5-carbaldehyde (146 mg; 1 mmol; 1 eq.), 4-methoxy-N-methylaniline (137 mg g; 1 mmol; 1 eq.); NaBH(AcO)$_3$ (318 mg; 1.5 mmol; 1.5 eq.) and AcOH (0.095 ml; 1.5 mmol; 1.5 eq.) as described above. Yield: 0.030 g (11%); MS m/z: 268.3 [M+H]$^+$; $^1$H-NMR (400 MHz, DMSO d6): δ 2.89 (s, 3H); 3.64 (s, 3H); 4.53 (s, 2H); 6.71-6.78 (m, 4H); 7.05-7.07 (m, 1H); 7.35 (br s, 1H); 7.49 (d, 1H, $^3$J=8.3 Hz); 8.13 (s, 1H); 12.35 (br s, 1H); HPLC (METHOD [A]): rt 6.28 min (90.3%)

Example 94

N-((1H-Benzo[d]imidazol-5-yl)methyl)(4-fluorophenyl)-N-methylmethanamine

The compound was synthesized starting from benzimidazol-5-carbaldehyde (146 mg; 1 mmol; 1 eq.), 4-fluoro-N-methylaniline (0.147 ml; 1 mmol; 1 eq.); NaBH(AcO)$_3$ (318 mg; 1.5 mmol; 1.5 eq.) and AcOH (0.095 ml; 1.5 mmol; 1.5 eq.) as described above. Yield: 0.035 g (13%); MS m/z: 270.1 [M+H]$^+$; $^1$H-NMR (400 MHz, DMSO d6): δ 2.05 (s, 3H); 3.47 (s, 2H); 3.57 (s, 2H); 7.11-7.16 (m, 3H); 7.35-7.36 (m, 2H); 7.44-7.56 (m, 2H); 8.14 (s, 1H); HPLC (METHOD [A]): rt 7.14 min (95.9%)

Analytical Methods

The analytical HPLC-system consisted of a Merck-Hitachi device (model LaChrom®) utilizing a Li-Chrospher® 100 RP 18 (5 μm). analytical column (length: 125 mm. diameter: 4 mm). and a diode array detector (DAD) with λ=214 nm as the reporting wavelength. The compounds were analyzed using a gradient at a flow rate of 1 mL/min; whereby eluent (A) was acetonitrile. eluent (B) was water. both containing 0.1% (v/v) trifluoro acetic acid applying the following gradient: Method [A]:0 min-5 min. 5% (A); 5 min-17 min, 5-15% (A); 17 min-29 min, 15-95% (A); 29 min-32 min, 95% (A); 32 min-33 min, 95-5% (A); 33 min-38 min, 5% (A); Method [B]: 0 min-25 min. 20-80% (A); 25 min-30 min. 80-95% (A); 30 min-31 min. 95-20% (A); 31 min-40 min 20% (A). The purities of all reported compounds were determined by the percentage of the peak area at 214 nm. ESI-Mass spectra were obtained with a SCIEX API 365 spectrometer (Perkin Elmer) utilizing the positive ionization mode.

Activity Screening

Fluorometric Assays

All measurements were performed with a BioAssay Reader HTS-7000Plus for microplates (Perkin Elmer) at 30° C. QC activity was evaluated fluorometrically using H-Gln-βNA. The samples consisted of 0.2 mM fluorogenic substrate, 0.25 U pyroglutamyl aminopeptidase (Unizyme, Høsholm, Denmark) in 0.2 M Tris/HCl, pH 8.0 containing 20 mM EDTA and an appropriately diluted aliquot of QC in a final volume of 250 μl. Excitation/emission wavelengths were 320/410 nm. The assay reactions were initiated by addition of glutaminyl cyclase. QC activity was determined from a standard curve of /3-naphthylamine under assay conditions. One unit is defined as the amount of QC catalyzing the formation of 1 μmol pGlu-βNA from H-Gln-/3NA per minute under the described conditions.

In a second fluorometric assay, QC was activity determined using H-Gln-AMC as substrate. Reactions were carried out at 30° C. utilizing the NOVOStar reader for microplates (BMG labtechnologies). The samples consisted of varying concentrations of the fluorogenic substrate, 0.1 U pyroglutamyl aminopeptidase (Qiagen) in 0.05 M Tris/HCl, pH 8.0 containing 5 mM EDTA and an appropriately diluted aliquot of QC in a final volume of 250 µl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit software.

Spectrophotometric Assay of QC

This novel assay was used to determine the kinetic parameters for most of the QC substrates. QC activity was analyzed spectrophotometrically using a continuous method, that was derived by adapting a previous discontinuous assay (Bateman, R. C. J. 1989 J Neurosci Methods 30, 23-28) utilizing glutamate dehydrogenase as auxiliary enzyme. Samples consisted of the respective QC substrate, 0.3 mM NADH, 14 mM a-Ketoglutaric acid and 30 U/ml glutamate dehydrogenase in a final volume of 250 µl. Reactions were started by addition of QC and persued by monitoring of the decrease in absorbance at 340 nm for 8-15 min.

The initial velocities were evaluated and the enzymatic activity was determined from a standard curve of ammonia under assay conditions. All samples were measured at 30° C., using either the SPECTRAFluor Plus or the Sunrise (both from TECAN) reader for microplates. Kinetic data was evaluated using GraFit software.

Inhibitor Assay

For inhibitor testing, the sample composition was the same as described above, except for the putative inhibitory compound added. For a rapid test of QC-inhibition, samples contained 4 mM of the respective inhibitor and a substrate concentration at 1 $K_M$. For detailed investigations of the inhibition and determination of $K_i$-values, influence of the inhibitor on the auxiliary enzymes was investigated first. In every case, there was no influence on either enzyme detected, thus enabling the reliable determination of the QC inhibition. The inhibitory constant was evaluated by fitting the set of progress curves to the general equation for competitive inhibition using GraFit software.

Results

Examples 10 to 11, 19-20, 23 to 27, 34, 37, 44 to 49, 51 to 52, 54 to 57, 59 to 60, 62, 66 to 69, 71 to 72, 74 to 76, 78, 80 to 81, 83, 86 to 87 and 89 were tested and gave hQC $IC_{50}$ values of less than 10 µM. Certain specific values are given in the table below:

| Example no. | hQC $K_i$ [µM] | hQC $IC_{50}$ [µM] |
|---|---|---|
| 20 | 0.346 | 3.99 |
| 23 | 0.473 | 3.65 |
| 51 | 0.313 | 3.16 |
| 52 | 0.305 | 3.06 |
| 54 | 0.194 | 2.65 |
| 55 | 0.228 | 3.71 |
| 56 | 0.271 | 4.12 |
| 57 | 0.519 | 3.41 |
| 80 | 1.08 | 4.08 |
| 87 | — | 3.14 |

Analytical Methods

HPLC:

Method [A]: The analytical HPLC-system consisted of a Merck-Hitachi device (model LaChrom®) utilizing a LUNA® RP 18 (5 µm), analytical column (length: 125 mm, diameter: 4 mm), and a diode array detector (DAD) with λ=214 nm as the reporting wavelength. The compounds were analyzed using a gradient at a flow rate of 1 mL/min; whereby eluent (A) was acetonitrile, eluent (B) was water, both containing 0.1% (v/v) trifluoro acetic acid applying the following gradient:: 0 min-5 min→5% (A), 5 min-17 min→5-15% (A), 15 min-27 min→15-95% (A) 27 min-30 min→95% (A), Method [B]: 0 min-15 min→5-60% (A), 15 min-20 min→60-95% (A), 20 min-23 min→95% (A), Method [C]: 0 min-20 min→5-60% (A), 20 min-25 min→60-95% (A). 25 min-30 min→95% (A).

Method [B]: The analytical HPLC-system consisted of a Agilent MSD 1100 utilizing a Waters SunFire RP 18 (2.5 µm), analytical column (length: 50 mm, diameter: 2.1 mm), and a diode array detector (DAD) with λ=254 nm as the reporting wavelength. The compounds were analyzed using a gradient at a flow rate of 0.6 mL/min; whereby eluent (A) was acetonitrile, eluent (B) was water and eluent (C) 2% formic acid in acetonitrile applying the following gradient:

| Time min | % Solvent B | % Solvent C |
|---|---|---|
| 0 | 90 | 5 |
| 2.5 | 10 | 5 |
| 4 | 10 | 5 |
| 4.5 | 90 | 5 |
| 6 | 90 | 5 |

The purities of all reported compounds were determined by the percentage of the peak area at 214 nm.

Mass-spectrometry, NMR-spectroscopy:

ESI-Mass spectra were obtained with a SCIEX API 365 spectrometer (Perkin Elmer) utilizing the positive ionization mode.

The $^1H$ NMR-Spectra (500 MHz) were recorded at a BRUKER AC 500. The solvent was DMSO-$D_6$, unless otherwise specified. Chemial shifts are expressed as parts per million (ppm) downfiled from tetramethylsilan. Splitting patterns have been designated as follows: s (singulet), d (doublet), dd (doublet of doublet), t (triplet), m (multiplet) and br (broad signal).

MALDI-TOF Mass Spectrometry

Matrix-assisted laser desorption/ionization mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals are recorded and filtered using LeCroy 9350M digital storage oscilloscope linked to a personal computer. Samples (5 µl) were mixed with equal volumes of the matrix solution. For matrix solution DHAP/DAHC was used, prepared by solving 30 mg 2',6'-dihydroxyacetophenone (Aldrich) and 44 mg diammonium hydrogen citrate (Fluka) in 1 ml acetonitrile/0.1% TFA in water (1/1, v/v). A small volume (≈1 µl) of the matrix-analyte-mixture was transferred to a probe tip and immediately evaporated in a vacuum chamber (Hewlett-Packard G2024A sample prep accessory) to ensure rapid and homogeneous sample crystallization.

For long-term testing of Glu$^1$-cyclization, An-derived peptides were incubated in 100 µl 0.1 M sodium acetate buffer, pH 5.2 or 0.1 M Bis-Tris buffer, pH 6.5 at 30° C. Peptides were applied in 0.5 mM [Aβ(3-11)a] or 0.15 mM [Aβ(3-21)a] concentrations, and 0.2 U QC is added all 24 hours. In case of Aβ(3-21)a, the assays contained 1% DMSO. At different times, samples are removed from the assay tube, peptides extracted using ZipTips (Millipore) according to the manufacturer's recommendations, mixed with matrix solution (1:1 v/v) and subsequently the mass spectra recorded. Negative controls either contain no QC or heat deactivated enzyme. For the inhibitor studies the sample composition was the same as described above, with exception of the inhibitory compound added (5 mM or 2 mM of a test compound of the invention).

Compounds and combinations of the invention may have the advantage that they are, for example, more potent, more selective, have fewer side-effects, have better formulation and stability properties, have better pharmacokinetic properties, be more bioavailable, be able to cross blood brain barrier and are more effective in the brain of mammals, are more compatible or effective in combination with other drugs or be more readily synthesized than other compounds of the prior art.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention embraces all combinations of preferred and more preferred groups and embodiments of groups recited above.

| Abbreviations | |
|---|---|
| (DHQ)$_2$PHAL | hydroquinine 1,4-phthalazinediyl diether |
| AcOH | acetic acid |
| DAD | diode array detector |
| DCC | dicyclohexyl carbodiimide |
| DEA | Diethylamine |
| DHAP/DAHC | dihydroxyacetone phosphate/dihydro-5-azacytidine |
| DMF | dimethylformamide |
| DMSO | dimethylsulfoxide |
| EDTA | ethylenediamine-N,N,N',N'-tetraacetic acid |
| EtOAc | ethyl acetate |
| EtOH | ethanol |
| FPLC | fast performance liquid chromatography |
| HPLC | high performance liquid chromatography |
| IPA | isopropanole |
| LD-TOF | laser-desorption time-of-flight mass spectrometry |
| ML | mother lye |
| MS | mass spectrometry |
| NMR | nuclear magnetic resonance |
| Pd$_2$dba$_3$ | tris(dibenzylideneacetone)dipalladium |
| TEA | triethyl amine |
| TFA | trifluoroacetic acid |
| THF | tetrahydrofuran |
| TLC | thin layer chromatography |
| TMSCN | trimethylsilyl cyanide |

What is claimed is:
1. A compound of formula (I):

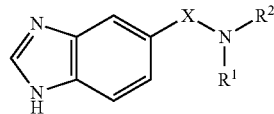

or a pharmaceutically acceptable salt, tautomer, or stereoisomers thereof wherein:
X represents a bond or a —$(CH_2)_m$-group;
m represents an integer selected from 1 to 3;
$R^1$ represents -aryl, —$C_{1-6}$alkylaryl, -cycloalkyl, —$C_{1-6}$alkylcycloalkyl, —$C_{1-6}$alkyl-Het, -aryl fused to heterocyclyl, —$C_{1-6}$alkylaryl fused to heterocyclyl, -aryl substituted by heteroaryl, —$C_{1-6}$alkylaryl substituted by heteroaryl, -aryl substituted by phenyl, —$C_{1-6}$alkylaryl substituted by phenyl, -aryl substituted by phenoxy or —$C_{1-6}$alkylaryl substituted by phenoxy;
and in which any of aforesaid aryl, heterocyclyl, heteroaryl, phenyl or phenoxy groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl)($C_{1-4}$alkyl), —$C(O)N(C_{1-4}$alkyl)($C_{1-4}$alkyl), —$C(O)NH_2$, —$C(O)NH(C_{1-4}$alkyl) and —$C(O)NH(C_{3-10}$cycloalkyl);
$R^2$ represents -aryl, —$C_{1-6}$alkylaryl, -cycloalkyl, —$C_{1-6}$alkylcycloalkyl, —$C_{1-6}$alkyl- Het, -aryl fused to heterocyclyl, —$C_{1-6}$alkylaryl fused to heterocyclyl, -aryl substituted by heteroaryl, —$C_{1-6}$alkylaryl substituted by heteroaryl, -aryl substituted by phenyl, —$C_{1-6}$alkylaryl substituted by phenyl, -aryl substituted by phenoxy or —$C_{1-6}$alkylaryl substituted by phenoxy;
and in which any of aforesaid aryl, heterocyclyl, heteroaryl, phenyl or phenoxy groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$S0_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl)($C_{1-4}$alkyl), —$C(O)N(C_{1-4}$alkyl)($C_{1-4}$alkyl), —$C(O)NH_2$, —$C(O)NH(C_{1-4}$alkyl) and —$C(O)NH(C_{3-10}$cycloalkyl);
Het represents a bicyclic heteroaryl group;
in which said bicyclic heteroaryl group may be optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)OC_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl)($C_{1-4}$alkyl), —$C(O)N(C_{1-4}$alkyl)($C_{1-4}$alkyl), —$C(O)NH_2$, —$C(O)NH(C_{1-4}$alkyl) and —$C(O)NH(C_{3-10}$cycloalkyl).

2. A compound as defined in claim 1, wherein $R^1$ represents $C_{1-6}$alkylaryl, —$C_{1-6}$alkyl-Het, —$C_{1-6}$alkylaryl fused to heterocyclyl or —$C_{1-6}$alkylaryl substituted by heteroaryl.

3. A compound as defined in claim 1, wherein $R^2$ represents -aryl, —$C_{1-6}$alkylaryl, —$C_{1-6}$alkylcycloalkyl, —$C_{1-6}$alkyl-Het, —$C_{1-6}$alkylaryl fused to heterocyclyl or —$C_{1-6}$alkylaryl substituted by heteroaryl.

4. A compound as defined in claim 1, wherein $R^1$ represents —$C_{1-6}$alkylaryl and $R^2$ represents —$C_{1-6}$alkylaryl or —$C_{1-6}$alkylcycloalkyl; wherein said aryl groups are optionally substituted by one or more halogen, cyano, $C_{1-6}$alkyl, $C_{1-6}$alkoxy, —$C_{1-6}$thioalkyl or —$N(C_{1-4}$alkyl)($C_{1-4}$alkyl) groups.

5. A compound as defined in claim 1, wherein $R^1$ and $R^2$ both represent —$C_{1-6}$alkylaryl; wherein said phenyl groups are optionally substituted by one or more halogen, cyano, $C_{1-6}$alkyl, $C_{1-6}$alkoxy, —$C_{1-6}$thioalkyl or —$N(C_{1-4}$alkyl)($C_{1-4}$alkyl) groups.

6. A compound as defined in claim 1, wherein $R^1$ and $R^2$ both represent —$C_{1-6}$alkylaryl substituted by to heteroaryl.

7. A compound as defined in claim 1, wherein $R^1$ and $R^2$ both represent —$C_{1-6}$alkylaryl substituted by heteroaryl.

8. A compound as defined in claim 1, wherein $R^1$ represents —$C_{1-6}$alkyl-Het and $R^2$ represents —$C_{1-6}$alkyl-Het, $C_{1-6}$alkylaryl, or —$C_{1-6}$alkyl cycloalkyl; wherein said Het groups are optionally substituted by one or more halogen or $C_{1-6}$alkyl groups; and wherein said aryl group is optionally substituted by one or more —$C_{1-6}$thioalkyl, $C_{1-6}$alkyl, $C_{1-6}$alkoxy, halogen or —$N(C_{1-4}$alkyl)($C_{1-4}$alkyl) groups.

9. A compound as defined in claim 1, wherein $R^1$ and $R^2$ bothrepresent —$C_{1-6}$alkyl-Het; wherein said Het groups are optionally substituted by one ormore halogen or $C_{1-6}$alky groups.

10. A compound as defined in claim 1, wherein $R^1$ represents aryl and $R^2$ represents —$C_{1-6}$alkylaryl.

11. A compound as defined in claim 1, wherein X represents a bondor a —$CH_2$-group.

12. A compound as defined in claim 11, wherein X representsa bond.

13. A compound according to claim 1, wherein saidcompound is selected from the group consisting of

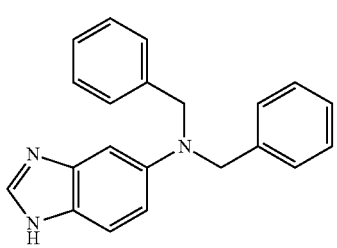 [SMILES: c1ccc(CN(Cc2ccccc2)c2ccc3[nH]cnc3c2)cc1]

N,N-Dibenzyl-1H-benzo[d]imidazol-5-amine;

-continued
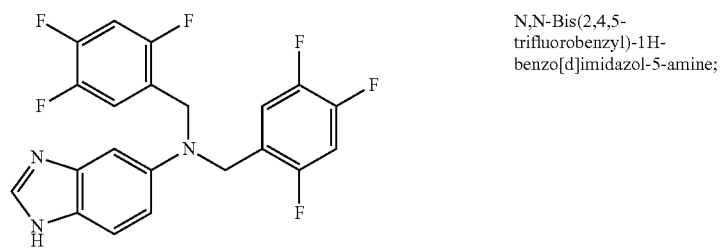
N,N-Bis(2,4,5-trifluorobenzyl)-1H-benzo[d]imidazol-5-amine;
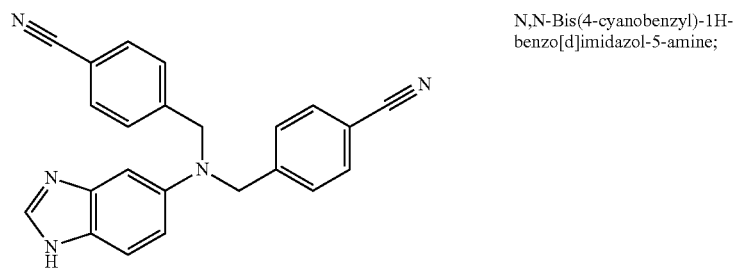
N,N-Bis(4-cyanobenzyl)-1H-benzo[d]imidazol-5-amine;
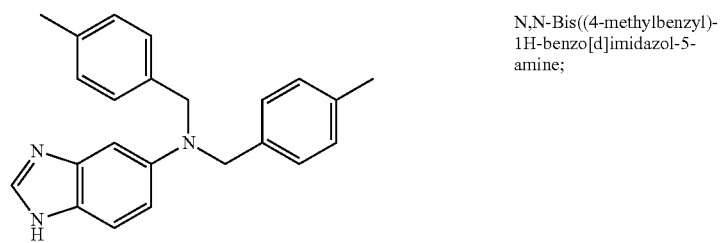
N,N-Bis((4-methylbenzyl)-1H-benzo[d]imidazol-5-amine;
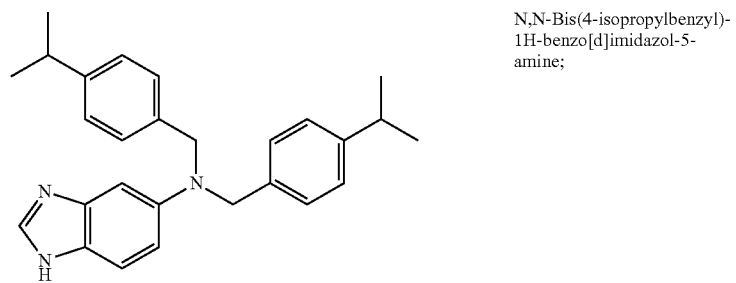
N,N-Bis(4-isopropylbenzyl)-1H-benzo[d]imidazol-5-amine;
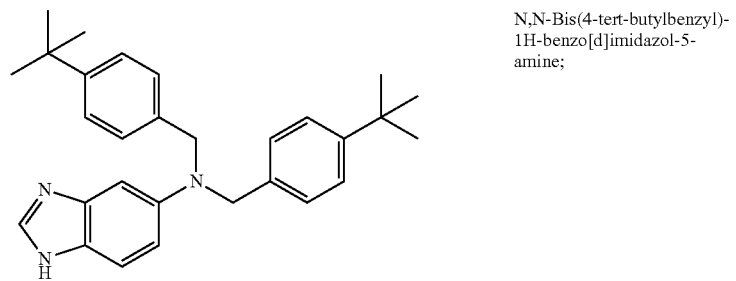
N,N-Bis(4-tert-butylbenzyl)-1H-benzo[d]imidazol-5-amine;
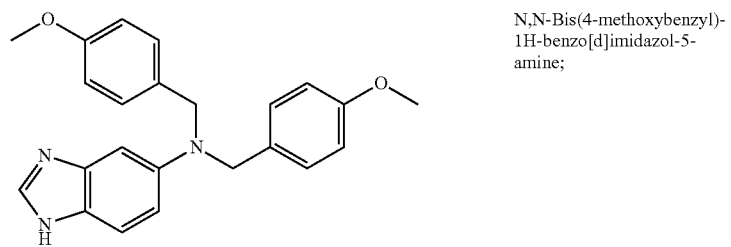
N,N-Bis(4-methoxybenzyl)-1H-benzo[d]imidazol-5-amine;

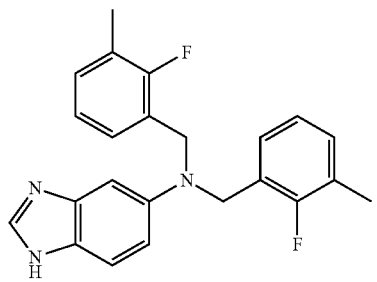 [SMILES: Cc1cccc(CN(Cc2cccc(C)c2F)c2ccc3[nH]cnc3c2)c1F] N,N-Bis(2-fluoro-3-methylbenzyl)-1H-benzo[d]imidazol-5-amine;
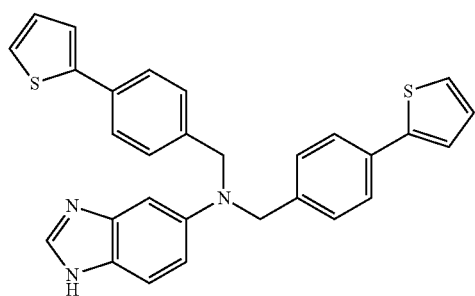 [SMILES: c1csc(-c2ccc(CN(Cc3ccc(-c4cccs4)cc3)c3ccc4[nH]cnc4c3)cc2)c1] N,N-Bis(4-(thiophen-2-yl)benzyl)-1H-benzo[d]imidazol-5-amine;
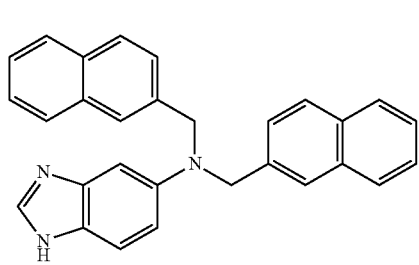 [SMILES: c1ccc2cc(CN(Cc3ccc4ccccc4c3)c3ccc4[nH]cnc4c3)ccc2c1] N,N-Bis((naphthalen-2-yl)methyl))-1H-benzo[d]imidazol-5-amine;
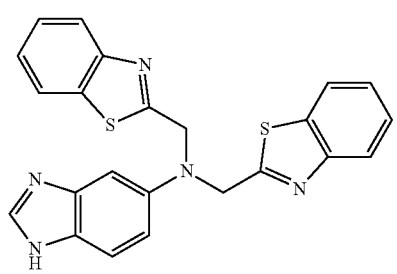 [SMILES: c1ccc2sc(CN(Cc3nc4ccccc4s3)c3ccc4[nH]cnc4c3)nc2c1] N,N-Bis((benzo[d]thiazol-2-yl)methyl)-1H-benzo[d]imidazol-5-amine;
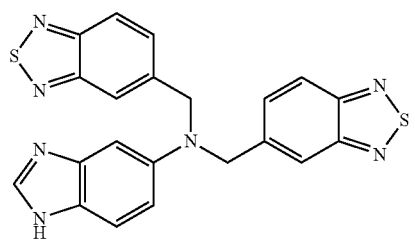 [SMILES: c1nc2cc(N(Cc3ccc4nsnc4c3)Cc3ccc4nsnc4c3)ccc2[nH]1] N,N-Bis-((benzo[c][1,2,5]thiadiazol-5-yl)methyl)-1H-benzo[d]imidazol-5-amine;

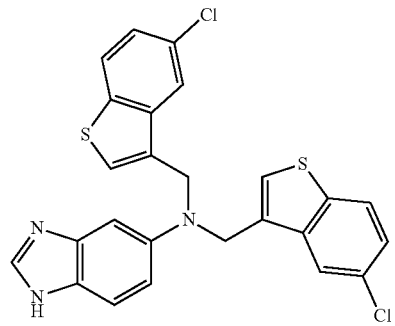 [SMILES: Clc1ccc2scc(CN(Cc3csc4ccc(Cl)cc34)c3ccc4[nH]cnc4c3)c2c1]
N,N-Bis((5-chlorobenzo[b]thiophen-3-yl)methyl)-1H-benzo[d]imidazol-5-amine;
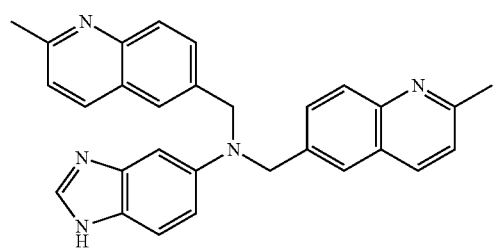
N,N-Bis((2-methylquinolin-6-yl)methyl)-1H-benzo[d]imidazol-5-amine;
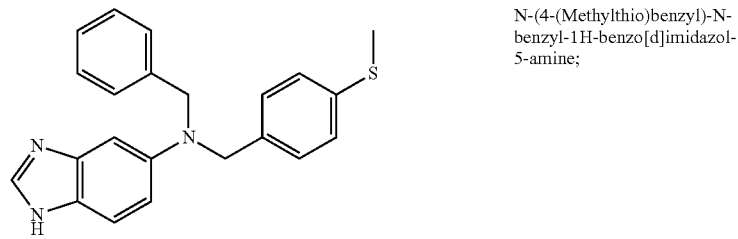
N-(4-(Methylthio)benzyl)-N-benzyl-1H-benzo[d]imidazol-5-amine;
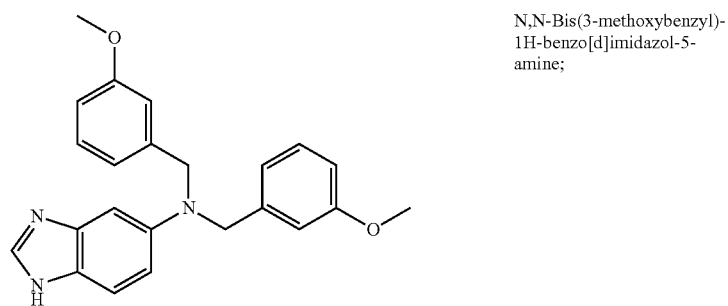
N,N-Bis(3-methoxybenzyl)-1H-benzo[d]imidazol-5-amine;
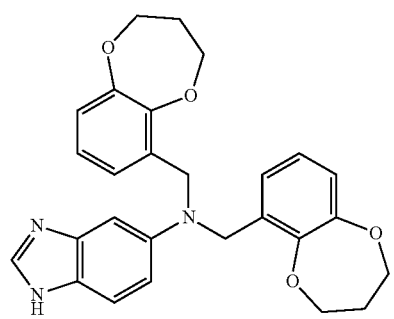 [SMILES: c1cc(CN(Cc2cccc3c2OCCCO3)c2ccc3[nH]cnc3c2)c2c(c1)OCCCO2]
N,N-Bis((3,4-dihydro-2H-benzo[b][1,4]dioxepin-9-yl)methyl)-1H-benzo[d]imidazol-5-amine;

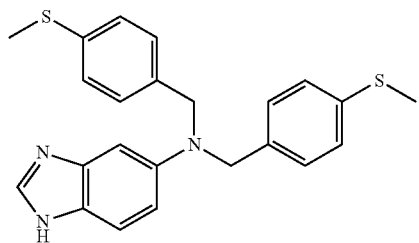 N,N-Bis(4-(methylthio)benzyl)-1H-benzo[d]imidazol-5-amine;
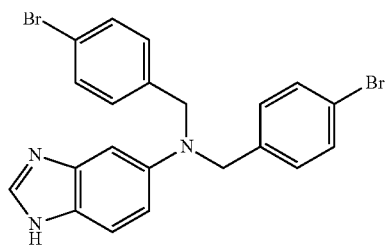 [SMILES: Brc1ccc(CN(Cc2ccc(Br)cc2)c2ccc3[nH]cnc3c2)cc1] N,N-Bis(4-bromobenzyl)-1H-benzo[d]imidazol-5-amine;
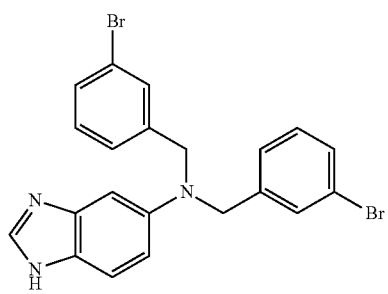 [SMILES: Brc1cccc(CN(Cc2cccc(Br)c2)c2ccc3[nH]cnc3c2)c1] N,N-Bis(3-bromobenzyl)-1H-benzo[d]imidazol-5-amine;
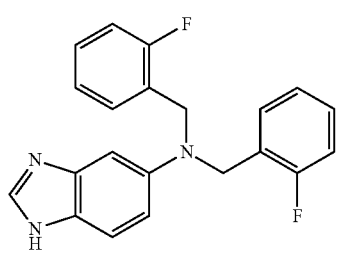 [SMILES: Fc1ccccc1CN(Cc1ccccc1F)c1ccc2[nH]cnc2c1] N,N-Bis(2-fluorobenzyl)-1H-benzo[d]imidazol-5-amine;
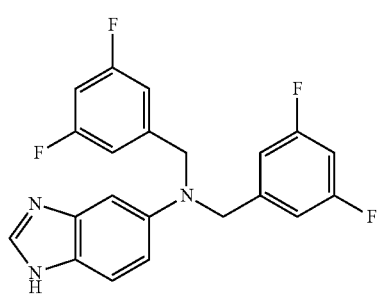 [SMILES: Fc1cc(F)cc(CN(Cc2cc(F)cc(F)c2)c2ccc3[nH]cnc3c2)c1] N,N-Bis(3,5-difluorobenzyl)-1H-benzo[d]imidazol-5-amine;
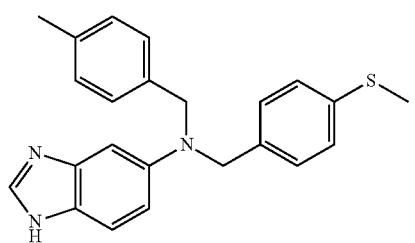 [SMILES: CSc1ccc(CN(Cc2ccc(C)cc2)c2ccc3[nH]cnc3c2)cc1] N-(4-(Methylthio)benzyl)-N-(4-methylbenzyl)-1H-benzo[d]imidazol-5-amine;

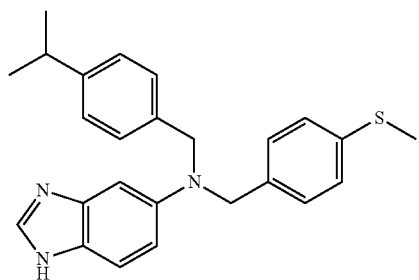 [SMILES: CSc1ccc(CN(Cc2ccc(C(C)C)cc2)c2ccc3[nH]cnc3c2)cc1]
N-(4-(Methylthio)benzyl)-N-(4-isopropylbenzyl)-1H-benzo[d]imidazol-5-amine;
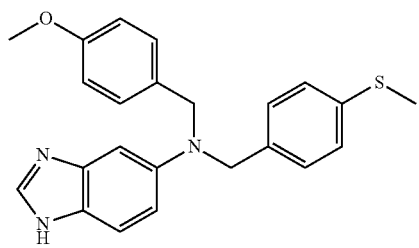
N-(4-(Methylthio)benzyl)-N-(4-methoxybenzyl)-1H-benzo[d]imidazol-5-amine;
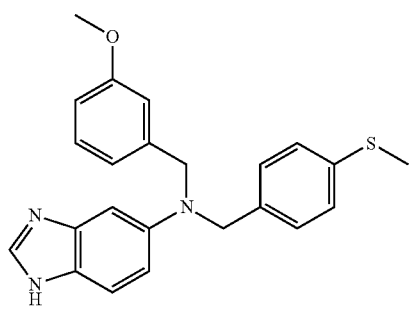 [SMILES: COc1cccc(CN(Cc2ccc(SC)cc2)c2ccc3[nH]cnc3c2)c1]
N-(3-Methoxybenzyl)-N-(4-(methylthio)benzyl)-1H-benzo[d]imidazol-5-amine;
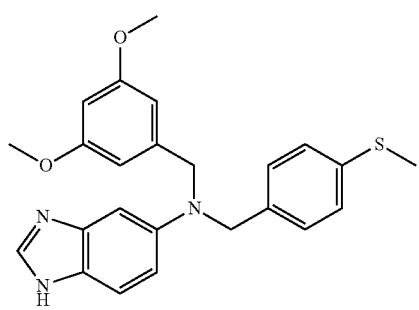
N-(3,5-Dimethoxybenzyl)-N-(4-(methylthio)benzyl)-1H-benzo[d]imidazol-5-amine;
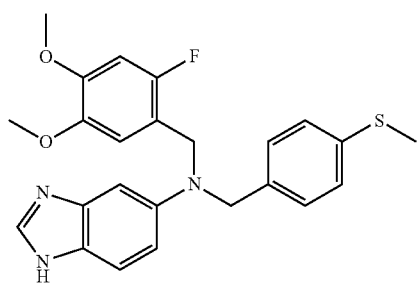
N-(2-Fluoro-4,5-dimethoxybenzyl)-N-(4-(methylthio)benzyl)-1H-benzo[d]imidazol-5-amine;

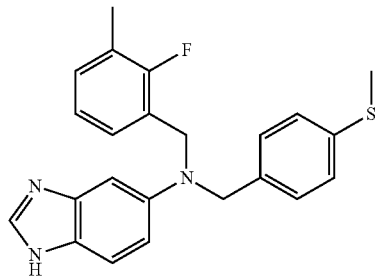 [SMILES: CSc1ccc(CN(Cc2cccc(C)c2F)c2ccc3[nH]cnc3c2)cc1]
N-(2-Fluoro-3-methylbenzyl)-N-(4-(methylthio)benzyl)-1H-benzo[d]imidazol-5-amine;
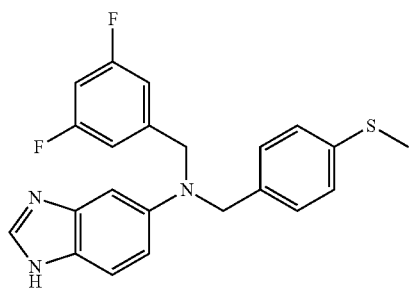 [SMILES: CSc1ccc(CN(Cc2cc(F)cc(F)c2)c2ccc3[nH]cnc3c2)cc1]
N-(3,5-Difluorobenzyl)-N-(4-(methylthio)benzyl)-1H-benzo[d]imidazol-5-amine;
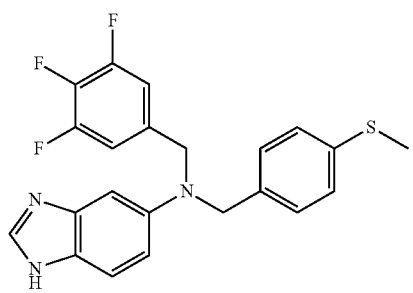 [SMILES: CSc1ccc(CN(Cc2cc(F)c(F)c(F)c2)c2ccc3[nH]cnc3c2)cc1]
N-(3,4,5-Trifluorobenzyl)-N-(4-(methylthio)benzyl)-1H-benzo[d]imidazol-5-amine;
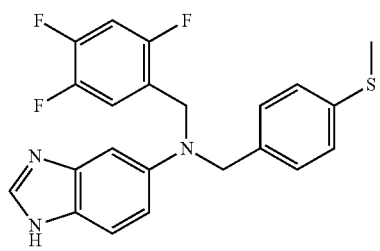 [SMILES: CSc1ccc(CN(Cc2cc(F)c(F)cc2F)c2ccc3[nH]cnc3c2)cc1]
N-(2,4,5-Trifluorobenzyl)-N-(4-(methylthio)benzyl)-1H-benzo[d]imidazol-5-amine;
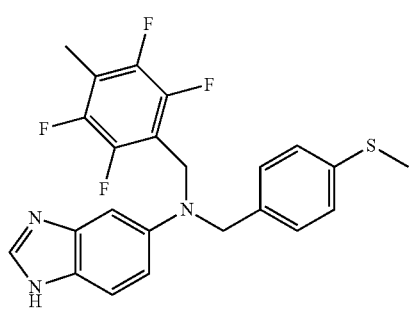 [SMILES: CSc1ccc(CN(Cc2c(F)c(F)c(C)c(F)c2F)c2ccc3[nH]cnc3c2)cc1]
N-(2,3,5,6-Tetrafluoro-4-methylbenzyl)-N-(4-(methylthio)benzyl)-1H-benzo[d]imidazol-5-amine;

-continued

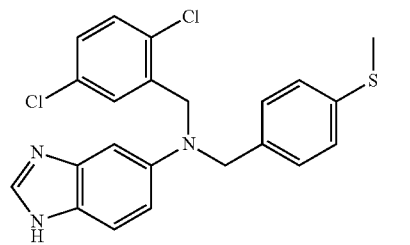 [SMILES: CSc1ccc(CN(Cc2cc(Cl)ccc2Cl)c2ccc3[nH]cnc3c2)cc1]
N-(2,5-Dichlorobenzyl)-N-(4-(methylthio)benzyl)-1H-benzo[d]imidazol-5-amine;

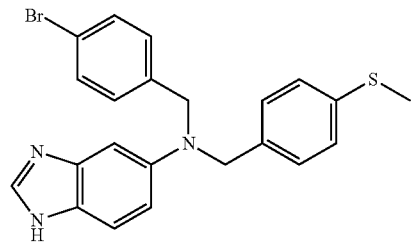 [SMILES: CSc1ccc(CN(Cc2ccc(Br)cc2)c2ccc3[nH]cnc3c2)cc1]
N-(4-(Methylthio)benzyl)-N-(4-bromobenzyl)-1H-benzo[d]imidazol-5-amine;

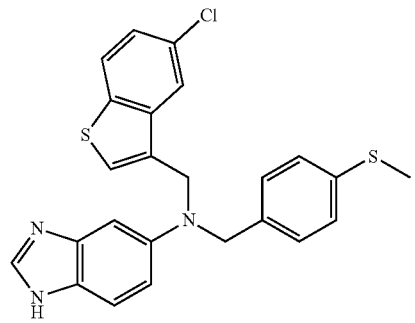 [SMILES: CSc1ccc(CN(Cc2csc3ccc(Cl)cc23)c2ccc3[nH]cnc3c2)cc1]
N-(4-(Methylthio)benzyl)-N-((5-chlorobenzo[b]thiophen-3-yl)methyl)-1H-benzo[d]imidazol-5-amine;

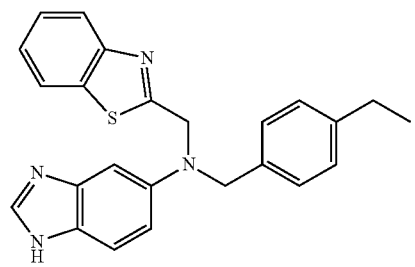
N-(4-(Methylthio)benzyl)-N-((benzo[d]thiazol-2-yl)methyl)-1H-benzo[d]imidazol-5-amine;

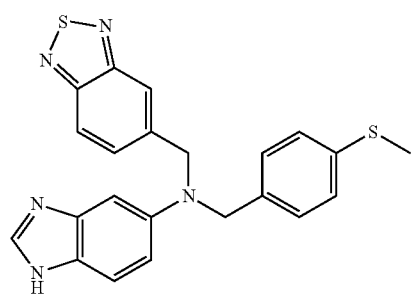 [SMILES: CSc1ccc(CN(Cc2ccc3nsnc3c2)c2ccc3[nH]cnc3c2)cc1]
N-(4-(Methylthio)benzyl)-N-((benzo[c][1,2,5]thiadiazol-6-yl)methyl)-1H-benzo[d]imidazol-5-amine;

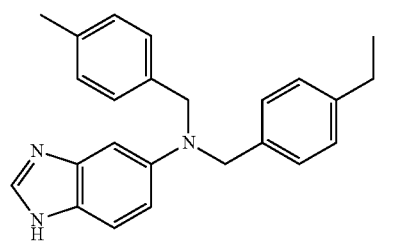 [SMILES: CCc1ccc(CN(Cc2ccc(C)cc2)c2ccc3[nH]cnc3c2)cc1]
N-(4-Ethylbenzyl)-N-(4-methylbenzyl)-1H-benzo[d]imidazol-5-amine;

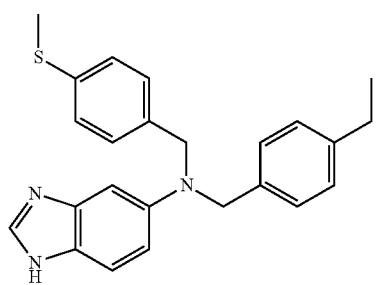 [SMILES: CCc1ccc(CN(Cc2ccc(SC)cc2)c2ccc3[nH]cnc3c2)cc1] N-(4-(Methylthio)benzyl)-N-(4-ethylbenzyl)-1H-benzo[d]imidazol-5-amine;
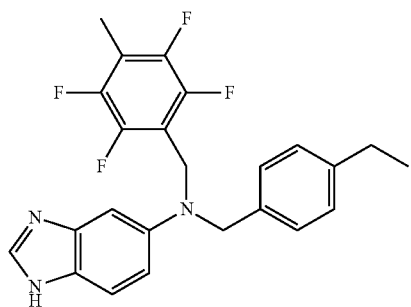 [SMILES: CCc1ccc(CN(Cc2c(F)c(F)c(C)c(F)c2F)c2ccc3[nH]cnc3c2)cc1] N-(2,3,5,6-Tetrafluoro-4-methylbenzyl)-N-(4-ethylbenzyl)-1H-benzo[d]imidazol-5-amine;
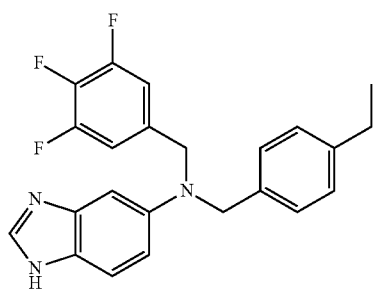 [SMILES: CCc1ccc(CN(Cc2cc(F)c(F)c(F)c2)c2ccc3[nH]cnc3c2)cc1] N-(3,4,5-Trifluorobenzyl)-N-(4-ethylbenzyl)-1H-benzo[d]imidazol-5-amine;
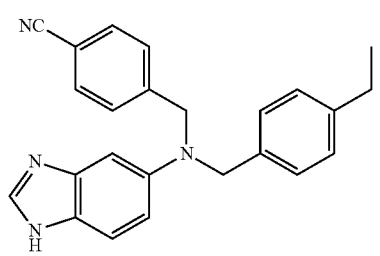 [SMILES: CCc1ccc(CN(Cc2ccc(C#N)cc2)c2ccc3[nH]cnc3c2)cc1] N-(4-Cyanobenzyl)-N-(4-ethylbenzyl)-1H-benzo[d]imidazol-5-amine;
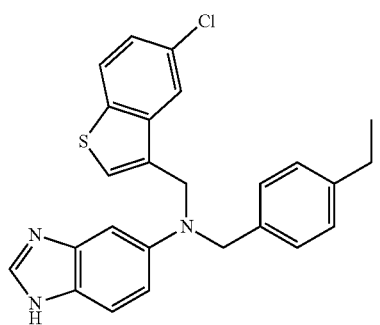 [SMILES: CCc1ccc(CN(Cc2csc3ccc(Cl)cc23)c2ccc3[nH]cnc3c2)cc1] N-(4-Ethylbenzyl)-N-((5-chlorobenzo[b]thiophen-3-yl)methyl)-1H-benzo[d]imidazol-5-amine;

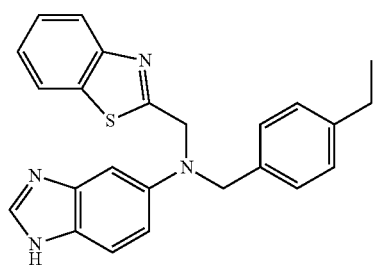 [SMILES: CCc1ccc(CN(Cc2nc3ccccc3s2)c2ccc3[nH]cnc3c2)cc1]
N-(4-Ethylbenzyl)-N-((benzo[d]thiazol-2-yl)methyl)-1H-benzo[d]imidazol-5-amine;
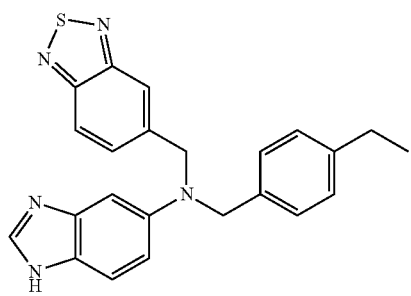 [SMILES: CCc1ccc(CN(Cc2ccc3nsnc3c2)c2ccc3[nH]cnc3c2)cc1]
N-(4-Ethylbenzyl)-N-((benzo[c][1,2,5]thiadiazol-6-yl)methyl)-1H-benzo[d]imidazol-5-amine;
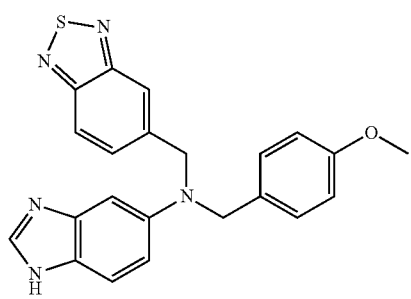 [SMILES: COc1ccc(CN(Cc2ccc3nsnc3c2)c2ccc3[nH]cnc3c2)cc1]
N-(4-Methoxybenzyl)-N-((benzo[c][1,2,5]thiadiazol-6-yl)methyl)-1H-benzo[d]imidazol-5-amine;
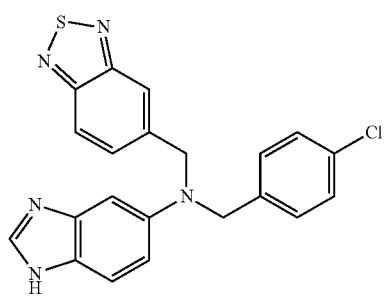 [SMILES: Clc1ccc(CN(Cc2ccc3nsnc3c2)c2ccc3[nH]cnc3c2)cc1]
N-(4-Chlorobenzyl)-N-((benzo[c][1,2,5]thiadiazol-6-yl)methyl)-1H-benzo[d]imidazol-5-amine;
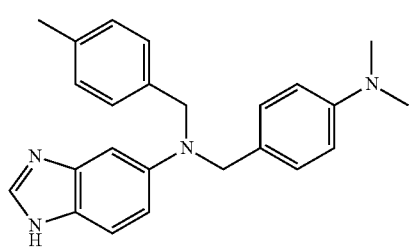 [SMILES: Cc1ccc(CN(Cc2ccc(N(C)C)cc2)c2ccc3[nH]cnc3c2)cc1]
N-(4-(Dimethylamino)benzyl)-N-(4-methylbenzyl)-1H-benzo[d]imidazol-5-amine;

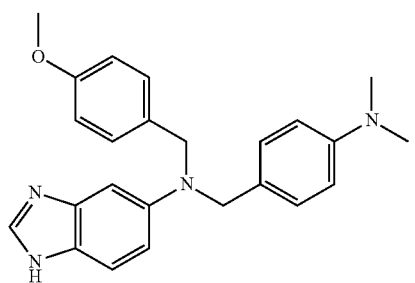 [SMILES: COc1ccc(CN(Cc2ccc(N(C)C)cc2)c2ccc3[nH]cnc3c2)cc1] N-(4-(Dimethylamino)benzyl)-N-(4-methoxybenzyl)-1H-benzo[d]imidazol-5-amine;

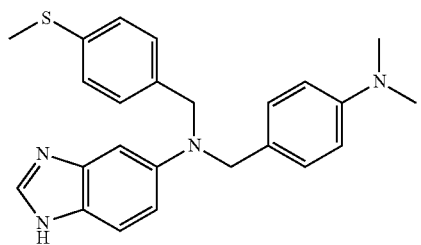 N-(4-(Dimethylamino)benzyl)-N-(4-(methylthio)benzyl)-1H-benzo[d]imidazol-5-amine;

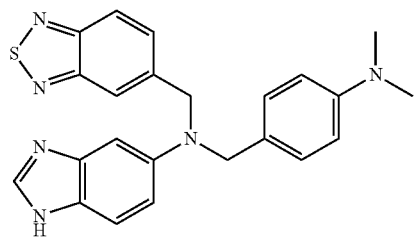 [SMILES: CN(C)c1ccc(CN(Cc2ccc3nsnc3c2)c2ccc3[nH]cnc3c2)cc1] N-(4-(Dimethylamino)benzyl)-N-((benzo[c][1,2,5]thiadiazol-5-yl)methyl)-1H-benzo[d]imidazol-5-amine;

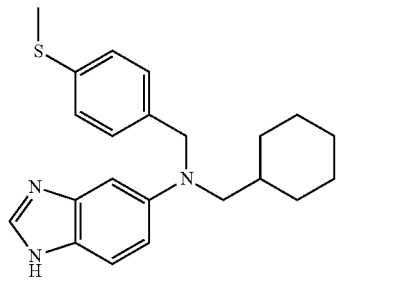 [SMILES: CSc1ccc(CN(CC2CCCCC2)c2ccc3[nH]cnc3c2)cc1] N-(4-(Methylthio)benzyl)-N-(cyclohexylmethyl)-1H-benzo[d]imidazol-5-amine;

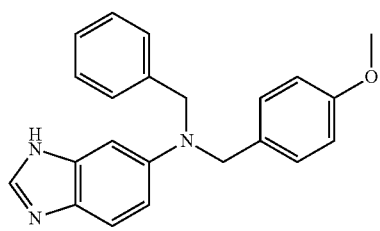 [SMILES: COc1ccc(CN(Cc2ccccc2)c2ccc3nc[nH]c3c2)cc1] N-(4-Methoxybenzyl)-N-benzyl-3H-benzo[d]imidazol-5-amine;

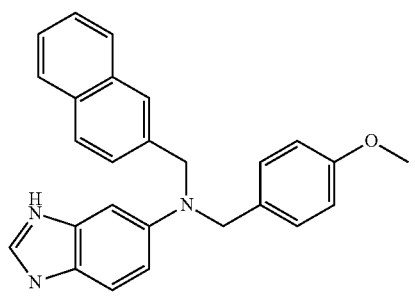 N-(4-Methoxybenzyl)-N-((naphthalen-2-yl)methyl)-3H-benzo[d]imidazol-5-amine;

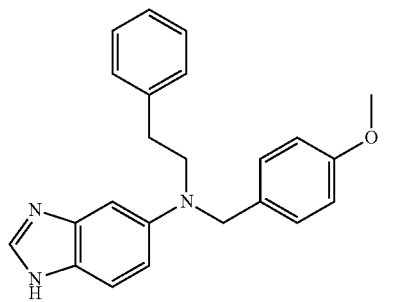 [SMILES: COc1ccc(CN(CCc2ccccc2)c2ccc3[nH]cnc3c2)cc1]

N-(4-Methoxybenzyl)-N-phenethyl-1H-benzo[d]imidazol-5-amine;

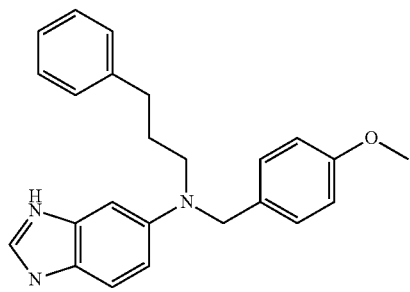

N-(4-Methoxybenzyl)-N-(3-phenylpropyl)-3H-benzo[d]imidazol-5-amine; and

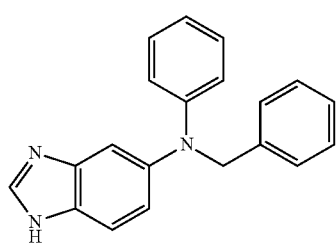 [SMILES: c1ccc(CN(c2ccccc2)c2ccc3[nH]cnc3c2)cc1]

N-Benzyl-N-phenyl-1H-benzo[d]imidazol-5-amine;

or a pharmaceutically accepted salt thereof, including all tautomers and stereoisomers.

14. A pharmaceutical composition comprising a compound according to claim 1, optionally in combination with one or more therapeutically acceptable diluents or carriers.

15. The pharmaceutical composition of claim 14, which comprises additionally at least one compound, selected from the group consisting of neuroprotectants, antiparkinsonian drugs, amyloid protein deposition inhibitors, betaamyloid synthesis inhibitors, antidepressants, anxiolytic drugs, antipsychotic drugs and anti-multiple sclerosis drugs.

16. The pharmaceutical composition of claim 14, which comprises additionally at least one compound, selected from the group consisting of PEP-inhibitors, LiCl, inhibitors of inhibitors of DP IV or DP IV-like enzymes, acetylcholinesterase (ACE) inhibitors, PIMT enhancers, inhibitors of beta secretases, inhibitors of gamma secretases, inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors, interferon-tau (trophoblastin) and SAIK-MS.

17. A process for preparation of a compound of formula(I) according to claim 1, which comprises:

(a) preparing a compound of formula (I) wherein X represents a bond by reacting a compound of formula (II)

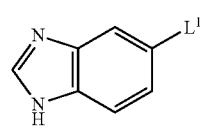

(II)

with a compound of formula $NHR^1R^2$, wherein $l^1$ represents a suitable leaving group and $R^1$ and $R^2$ are as defined in claim 1;

(b) preparing a compound of formula (I) wherein X represents a bond, $R^1$ is as defined in claim 1 and $R^2$ represents —$C_{1-6}$alkylaryl, —$C_{1-6}$alkyl-Het, —$C_{1-6}$alkylaryl fused to heterocyclyl, —$C_{1-6}$alkylaryl substituted by heteroaryl, —$C_{1-6}$alkylaryl substituted by phenyl or —$C_{1-6}$alkylaryl substituted by phenoxy, by alkylating a compound of formula (III):

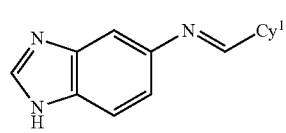

(III)

wherein $Cy^1$ represents the aryl or Het group of $R^2$;

(c) preparing a compound of formula (I) wherein X represents a bond, $R^1$ is as defined in claim 1 and $R^2$ represents —$C_{1-6}$alkyl, —$C_{1-6}$alkylaryl, —$C_{1-6}$alkylcycloalkyl, —$C_{1-6}$alkyl-Het, —$C_{1-6}$alkylaryl fused to heterocyclyl, —$C_{1-6}$alkylaryl substituted by heteroaryl, —$C_{1-6}$alkylaryl substituted by phenyl or —$C_{1-6}$alkylaryl substituted by phenoxy, by reacting a compound of formula (IV):

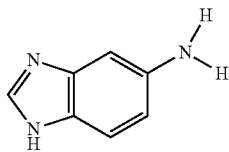

(IV)

with a compound of formula H—CO—$R^2$, wherein $R^2$ is as defined in claim 1;

(d) preparing a compound of formula (I) wherein: X represents a bond, $R^1$ is as defined in claim 1 and $R^2$ is as defined in claim 1; or X represents a bond and $R^1$ and $R^2$ represent identical groups, by reacting a compound of formula (IV):

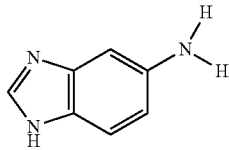

(IV)

or an optionally protecting derivative thereof with a compound of formula $L^2$-$R^2$, wherein $L^2$ represents a suitable leaving group and $R^2$ is as defined in claim 1;

(e) preparing a compound of formula (I) wherein X represents a —$(CH_2)_m$-group, by reacting a compound of formula (VI):

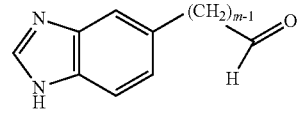

(VI)

with a compound of formula $HNR^1R^2$, wherein $R^1$ and $R^2$ are as defined in claim 1;

(f) interconversion of compounds of formula (I), such as preparing a compound of formula (I) wherein $R^1$ is as defined in claim 1 by reacting a compound of formula (V):

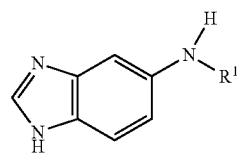

(V)

with a compound of formula $L^4$—$R^{1a}$, wherein $R^2$ is as defined in claim 1, $L^4$ represents a suitable leaving group such as bromine and $R^{1a}$ represents an $R^1$ group as defined in claim 1; and/or (g) deprotecting a compound of formula (I) which is protected.

18. The process of claim 17, wherein $L^1$ is bromine, $L^2$ is bromine, or $L^4$ bromine.

* * * * *

SEQUENCE LISTING

<160> NUMBER OF SEQ ID NOS: 20

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 40
<212> TYPE: PRT
<213> ORGANISM: Homo sapiens

```
<400> SEQUENCE: 3

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
            35                  40

<210> SEQ ID NO 4
<211> LENGTH: 38
<212> TYPE: PRT
<213> ORGANISM: Homo sapiens

<400> SEQUENCE: 4

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
            35

<210> SEQ ID NO 5
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

<400> SEQUENCE: 5

Gln Gly Pro Trp Leu Glu Glu Glu Glu Ala Tyr Gly Trp Met Asp
1               5                   10                  15

Phe

<210> SEQ ID NO 6
<211> LENGTH: 13
<212> TYPE: PRT
<213> ORGANISM: Homo sapiens

<400> SEQUENCE: 6

Gln Leu Tyr Glu Asn Lys Pro Arg Arg Pro Tyr Ile Leu
1               5                   10

<210> SEQ ID NO 7
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 7

Gln His Trp Ser Tyr Gly Leu Arg Pro Gly
1               5                   10

<210> SEQ ID NO 8
<211> LENGTH: 97
<212> TYPE: PRT
<213> ORGANISM: Homo sapiens
```

```
<400> SEQUENCE: 8

Gln Pro Lys Val Pro Glu Trp Val Asn Thr Pro Ser Thr Cys Cys Leu
1               5                   10                  15

Lys Tyr Tyr Glu Lys Val Leu Pro Arg Arg Leu Val Val Gly Tyr Arg
                20                  25                  30

Lys Ala Leu Asn Cys His Leu Pro Ala Ile Ile Phe Val Thr Lys Arg
            35                  40                  45

Asn Arg Glu Val Cys Thr Asn Pro Asn Asp Asp Trp Val Gln Glu Tyr
        50                  55                  60

Ile Lys Asp Pro Asn Leu Pro Leu Leu Pro Thr Arg Asn Leu Ser Thr
65                  70                  75                  80

Val Lys Ile Ile Thr Ala Lys Asn Gly Gln Pro Gln Leu Leu Asn Ser
                85                  90                  95

Gln

<210> SEQ ID NO 9
<211> LENGTH: 76
<212> TYPE: PRT
<213> ORGANISM: Homo sapiens

<400> SEQUENCE: 9

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
        50                  55                  60

Lys His Leu Asp Gln Ile Phe Gln Asn Leu Lys Pro
65                  70                  75

<210> SEQ ID NO 10
<211> LENGTH: 76
<212> TYPE: PRT
<213> ORGANISM: Homo sapiens

<400> SEQUENCE: 10

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
        50                  55                  60

Asp His Leu Asp Lys Gln Thr Gln Thr Pro Lys Thr
65                  70                  75

<210> SEQ ID NO 11
<211> LENGTH: 68
<212> TYPE: PRT
<213> ORGANISM: Homo sapiens
```

-continued

```
<400> SEQUENCE: 11

Gln Val Gly Thr Asn Lys Glu Leu Cys Cys Leu Val Tyr Thr Ser Trp
1               5                   10                  15

Gln Ile Pro Gln Lys Phe Ile Val Asp Tyr Ser Glu Thr Ser Pro Gln
            20                  25                  30

Cys Pro Lys Pro Gly Val Ile Leu Leu Thr Lys Arg Gly Arg Gln Ile
        35                  40                  45

Cys Ala Asp Pro Asn Lys Lys Trp Val Gln Lys Tyr Ile Ser Asp Leu
50                  55                  60

Lys Leu Asn Ala
65

<210> SEQ ID NO 12
<211> LENGTH: 373
<212> TYPE: PRT
<213> ORGANISM: Homo sapiens

<400> SEQUENCE: 12

Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
            20                  25                  30

Ser Cys Gly Lys Arg Ala Ile Ile Leu Glu Thr Arg Gln His Arg Leu
        35                  40                  45

Phe Cys Ala Asp Pro Lys Glu Gln Trp Val Lys Asp Ala Met Gln His
    50                  55                  60

Leu Asp Arg Gln Ala Ala Ala Leu Thr Arg Asn Gly Gly Thr Phe Glu
65                  70                  75                  80

Lys Gln Ile Gly Glu Val Lys Pro Arg Thr Thr Pro Ala Ala Gly Gly
                85                  90                  95

Met Asp Glu Ser Val Val Leu Glu Pro Glu Ala Thr Gly Glu Ser Ser
            100                 105                 110

Ser Leu Glu Pro Thr Pro Ser Ser Gln Glu Ala Gln Arg Ala Leu Gly
        115                 120                 125

Thr Ser Pro Glu Leu Pro Thr Gly Val Thr Gly Ser Ser Gly Thr Arg
    130                 135                 140

Leu Pro Pro Thr Pro Lys Ala Gln Asp Gly Gly Pro Val Gly Thr Glu
145                 150                 155                 160

Leu Phe Arg Val Pro Pro Val Ser Thr Ala Ala Thr Trp Gln Ser Ser
                165                 170                 175

Ala Pro His Gln Pro Gly Pro Ser Leu Trp Ala Glu Ala Lys Thr Ser
            180                 185                 190

Glu Ala Pro Ser Thr Gln Asp Pro Ser Thr Gln Ala Ser Thr Ala Ser
        195                 200                 205

Ser Pro Ala Pro Glu Glu Asn Ala Pro Ser Glu Gly Gln Arg Val Trp
    210                 215                 220

Gly Gln Gly Gln Ser Pro Arg Pro Glu Asn Ser Leu Glu Arg Glu Glu
225                 230                 235                 240

Met Gly Pro Val Pro Ala His Thr Asp Ala Phe Gln Asp Trp Gly Pro
                245                 250                 255

Gly Ser Met Ala His Val Ser Val Val Pro Val Ser Ser Glu Gly Thr
            260                 265                 270

Pro Ser Arg Glu Pro Val Ala Ser Gly Ser Trp Thr Pro Lys Ala Glu
        275                 280                 285
```

Glu Pro Ile His Ala Thr Met Asp Pro Gln Arg Leu Gly Val Leu Ile
            290                 295                 300

Thr Pro Val Pro Asp Ala Gln Ala Ala Thr Arg Arg Gln Ala Val Gly
305                 310                 315                 320

Leu Leu Ala Phe Leu Gly Leu Phe Cys Leu Gly Val Ala Met Phe
                325                 330                 335

Thr Tyr Gln Ser Leu Gln Gly Cys Pro Arg Lys Met Ala Gly Glu Met
                340                 345                 350

Ala Glu Gly Leu Arg Tyr Ile Pro Arg Ser Cys Gly Ser Asn Ser Tyr
                355                 360                 365

Val Leu Val Pro Val
    370

<210> SEQ ID NO 13
<211> LENGTH: 76
<212> TYPE: PRT
<213> ORGANISM: Homo sapiens

<400> SEQUENCE: 13

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
                20                  25                  30

Ser Ser His Cys Pro Arg Glu Ala Val Ile Phe Lys Thr Lys Leu Asp
            35                  40                  45

Lys Glu Ile Cys Ala Asp Pro Thr Gln Lys Trp Val Gln Asp Phe Met
50                  55                  60

Lys His Leu Asp Lys Lys Thr Gln Thr Pro Lys Leu
65                  70                  75

<210> SEQ ID NO 14
<211> LENGTH: 33
<212> TYPE: PRT
<213> ORGANISM: Homo sapiens

<400> SEQUENCE: 14

Gln Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
                20                  25                  30

Leu

<210> SEQ ID NO 15
<211> LENGTH: 11
<212> TYPE: PRT
<213> ORGANISM: Homo sapiens

<400> SEQUENCE: 15

Arg Pro Lys Pro Gln Gln Phe Phe Gly Leu Met
1               5                   10

<210> SEQ ID NO 16
<211> LENGTH: 32
<212> TYPE: PRT
<213> ORGANISM: Artificial sequence
<220> FEATURE:
<223> OTHER INFORMATION: Synthetic peptide

```
<400> SEQUENCE: 16

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val Ile Ala
            20                  25                  30

<210> SEQ ID NO 17
<211> LENGTH: 30
<212> TYPE: PRT
<213> ORGANISM: Artificial sequence
<220> FEATURE:
<223> OTHER INFORMATION: Synthetic peptide

<400> SEQUENCE: 17

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
            20                  25                  30

<210> SEQ ID NO 18
<211> LENGTH: 34
<212> TYPE: PRT
<213> ORGANISM: Artificial sequence
<220> FEATURE:
<223> OTHER INFORMATION: Synthetic peptide

<400> SEQUENCE: 18

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Asn

<210> SEQ ID NO 19
<211> LENGTH: 34
<212> TYPE: PRT
<213> ORGANISM: Artificial sequence
<220> FEATURE:
<223> OTHER INFORMATION: Synthetic peptide

<400> SEQUENCE: 19

Glu Ala Ser Asn Cys Phe Ala Ile Arg His Phe Glu Asn Lys Phe Ala
1               5                   10                  15

Val Glu Thr Leu Ile Cys Phe Asn Leu Phe Leu Asn Ser Gln Glu Lys
            20                  25                  30

His Tyr

<210> SEQ ID NO 20
<211> LENGTH: 5
<212> TYPE: PRT
<213> ORGANISM: Artificial sequence
<220> FEATURE:
<223> OTHER INFORMATION: Synthetic peptide

<400> SEQUENCE: 20

Gln Tyr Asn Ala Asp
1               5
```